(12) United States Patent
Serhan et al.

(10) Patent No.: US 8,273,792 B2
(45) Date of Patent: Sep. 25, 2012

(54) ANTI-INFLAMMATORY ACTIONS OF NEUROPROTECTIN D1/PROTECTIN D1 AND IT'S NATURAL STEREOISOMERS

(75) Inventors: Charles N. Serhan, Needham, MA (US); Nicos A. Petasis, Hacienda Heights, CA (US); Bruce D. Levy, West Roxbury, MA (US)

(73) Assignees: The Brigham and Women's Hospital, Inc., Boston, MA (US); The University of Southern California, Los Angeles, CA (US)

( * ) Notice: Subject to any disclaimer, the term of this patent is extended or adjusted under 35 U.S.C. 154(b) by 1087 days.

(21) Appl. No.: 12/089,141

(22) PCT Filed: Oct. 3, 2006

(86) PCT No.: PCT/US2006/038326
§ 371 (c)(1),
(2), (4) Date: Aug. 4, 2008

(87) PCT Pub. No.: WO2007/041440
PCT Pub. Date: Apr. 12, 2007

(65) Prior Publication Data
US 2009/0156673 A1  Jun. 18, 2009

Related U.S. Application Data

(60) Provisional application No. 60/723,052, filed on Oct. 3, 2005, provisional application No. 60/749,786, filed on Dec. 13, 2005.

(51) Int. Cl.
*A01N 37/06* (2006.01)
*C07C 57/00* (2006.01)
*C07C 69/73* (2006.01)
*C07C 59/00* (2006.01)

(52) U.S. Cl. ........ 514/549; 514/560; 554/224; 560/183; 562/587

(58) Field of Classification Search .......... 514/549, 514/560; 554/224; 560/183; 562/587
See application file for complete search history.

(56) References Cited

U.S. PATENT DOCUMENTS

| | | | |
|---|---|---|---|
| 4,201,211 A | 5/1980 | Chandrasekaran et al. |
| 4,442,099 A | 4/1984 | Nicolau et al. |
| 4,567,290 A | 1/1986 | Nicolau et al. |
| 4,576,758 A | 3/1986 | Morris et al. |
| 4,666,701 A | 5/1987 | Horrobin et al. |
| 4,710,521 A | 12/1987 | Soukup et al. |
| 4,759,880 A | 7/1988 | Nicolau et al. |
| 4,810,424 A | 3/1989 | Gerwick et al. |

(Continued)

FOREIGN PATENT DOCUMENTS

EP  0736509  10/1996

(Continued)

OTHER PUBLICATIONS

Stahl, G.L. et al., Pharmacologic profile of lipoxins A5 and B5: new biologically active eicosanoids European Journal of Pharmacology, 1989, vol. 163, No. 1, 99. 55-60.

Lloyd-Evans, P. et al., Eicosanoid generation and effects on the aggregation of thrombocytes from the rainbow trout, Oncorhynchus mykiss, Biochimica et Biophysica Acta, Lipids and Lipid Metabolism, 1994, vol. 1215, No. 3. pp. 291-299.

(Continued)

*Primary Examiner* — Deborah D Carr
(74) *Attorney, Agent, or Firm* — Scott D. Rothenberger; Fulbright & Jaworski L.L.P.

(57) ABSTRACT (Neuro)protectin D1 (10R,17S-dihydroxy-docosa-4Z,7Z, 11E,13E,15Z,19Z-hexaenoic acid) and 15,16-dehydro-PD1 and their derivatives are useful in the treatment of airway inflammation, especially asthma.

20 Claims, 21 Drawing Sheets

U.S. PATENT DOCUMENTS

| | | |
|---|---|---|
| 5,087,790 A | 2/1992 | Petasis et al. |
| 5,136,501 A | 8/1992 | Silverman et al. |
| 5,177,046 A | 1/1993 | Savoca et al. |
| 5,409,955 A | 4/1995 | Bockow et al. |
| 5,411,988 A | 5/1995 | Bockow et al. |
| 5,441,951 A | 8/1995 | Serhan |
| 5,594,732 A | 1/1997 | Bell et al. |
| 5,604,258 A | 2/1997 | Ferrante et al. |
| 5,648,512 A | 7/1997 | Serhan |
| 5,650,157 A | 7/1997 | Bockow |
| 5,709,855 A | 1/1998 | Bockow |
| 5,752,238 A | 5/1998 | Dedrick |
| 5,756,789 A | 5/1998 | Bruce et al. |
| 5,814,599 A | 9/1998 | Mitragotri et al. |
| 5,842,040 A | 11/1998 | Hughes et al. |
| 5,845,265 A | 12/1998 | Woolston |
| 5,846,974 A | 12/1998 | Kallman et al. |
| 5,861,399 A | 1/1999 | Seed et al. |
| 5,870,717 A | 2/1999 | Wiecha |
| 5,878,400 A | 3/1999 | Carter, III |
| 5,878,423 A | 3/1999 | Anderson et al. |
| 5,890,138 A | 3/1999 | Godin et al. |
| 5,896,379 A | 4/1999 | Haber |
| 5,912,006 A | 6/1999 | Bockow et al. |
| 5,932,598 A | 8/1999 | Talley et al. |
| 5,946,467 A | 8/1999 | Pathakis et al. |
| 6,030,715 A | 2/2000 | Thompson et al. |
| 6,030,917 A | 2/2000 | Weinberg et al. |
| 6,048,897 A | 4/2000 | Serhan |
| 6,069,109 A | 5/2000 | Kao et al. |
| 6,117,911 A | 9/2000 | Grainger et al. |
| 6,201,022 B1 | 3/2001 | Mease et al. |
| 6,232,467 B1 | 5/2001 | Petasis et al. |
| 6,259,699 B1 | 7/2001 | Opalka et al. |
| 6,272,474 B1 | 8/2001 | Garcia |
| 6,316,648 B1 | 11/2001 | Serhan |
| 6,336,105 B1 | 1/2002 | Conklin et al. |
| 6,336,138 B1 | 1/2002 | Caswell et al. |
| 6,377,937 B1 | 4/2002 | Paskowitz |
| 6,397,212 B1 | 5/2002 | Biffar |
| 6,415,270 B1 | 7/2002 | Rackson et al. |
| 6,427,132 B1 | 7/2002 | Bowman-Amuah |
| 6,428,990 B1 | 8/2002 | Mukerji et al. |
| 6,569,075 B2 | 5/2003 | Serhan |
| 6,602,817 B1 | 8/2003 | Petasis |
| 6,620,919 B2 | 9/2003 | Serhan |
| 6,635,776 B2 | 10/2003 | Serhan |
| 6,653,493 B2 | 11/2003 | Serhan |
| 6,670,396 B2 | 12/2003 | Serhan et al. |
| 6,750,360 B2 | 6/2004 | Serhan |
| 6,887,901 B1 | 5/2005 | Serhan |
| 6,949,664 B2 | 9/2005 | Petasis |
| 7,030,159 B2 | 4/2006 | Serhan et al. |
| 7,053,230 B2 | 5/2006 | Serhan et al. |
| 7,341,840 B2 | 3/2008 | Serhan et al. |
| 2001/0023500 A1 | 9/2001 | Serhan |
| 2001/0031882 A1 | 10/2001 | Serhan |
| 2002/0010351 A1 | 1/2002 | Serhan |
| 2002/0045579 A1 | 4/2002 | Madara et al. |
| 2002/0055538 A1 | 5/2002 | Serhan et al. |
| 2002/0055539 A1 | 5/2002 | Bockow et al. |
| 2002/0082435 A1 | 6/2002 | Serhan |
| 2002/0091279 A1 | 7/2002 | Serhan |
| 2002/0094549 A1 | 7/2002 | Serhan et al. |
| 2002/0107289 A1 | 8/2002 | Serhan |
| 2002/0111505 A1 | 8/2002 | Serhan |
| 2002/0120013 A1 | 8/2002 | Serhan |
| 2002/0132847 A1 | 9/2002 | Serhan |
| 2002/0143069 A1 | 10/2002 | Serhan |
| 2002/0193431 A1 | 12/2002 | Serhan et al. |
| 2003/0032827 A1 | 2/2003 | Serhan |
| 2003/0055275 A1 | 3/2003 | Serhan |
| 2003/0060512 A1 | 3/2003 | Madara et al. |
| 2003/0069435 A1 | 4/2003 | Serhan |
| 2003/0134901 A1 | 7/2003 | Serhan |
| 2003/0166716 A1 | 9/2003 | Serhan et al. |
| 2003/0191184 A1 | 10/2003 | Serhan et al. |
| 2003/0191332 A1 | 10/2003 | Serhan |
| 2003/0195248 A1 | 10/2003 | Serhan et al. |
| 2003/0236423 A1 | 12/2003 | Petasis |
| 2004/0019110 A1 | 1/2004 | Van Dyke et al. |
| 2004/0044050 A1 | 3/2004 | Goodman et al. |
| 2004/0053998 A1 | 3/2004 | Serhan et al. |
| 2004/0059144 A1 | 3/2004 | Serhan et al. |
| 2004/0116408 A1 | 6/2004 | Serhan |
| 2004/0151712 A1 | 8/2004 | Madara et al. |
| 2004/0192785 A1 | 9/2004 | Serhan |
| 2005/0075398 A1 | 4/2005 | Bazan et al. |
| 2005/0228047 A1 | 10/2005 | Petasis |
| 2005/0261255 A1 | 11/2005 | Serhan et al. |
| 2006/0128804 A1 | 6/2006 | Serhan et al. |
| 2006/0293288 A1 | 12/2006 | Serhan et al. |
| 2008/0096961 A1 | 4/2008 | Serhan et al. |

FOREIGN PATENT DOCUMENTS

| | | |
|---|---|---|
| GB | 2033745 | 5/1980 |
| JP | 5186342 | 7/1993 |
| WO | WO 91/16914 | 11/1991 |
| WO | WO 98/19259 | 5/1998 |
| WO | WO 98/35469 | 8/1998 |
| WO | WO 98/46588 | 10/1998 |
| WO | WO 99/06913 | 2/1999 |
| WO | WO 99/13417 | 3/1999 |
| WO | WO 99/56727 | 11/1999 |
| WO | WO 00/32210 | 6/2000 |
| WO | WO 00/74632 | 12/2000 |
| WO | WO 01/60778 | 8/2001 |
| WO | WO 03/051350 | 6/2003 |
| WO | WO 03/053423 | 7/2003 |
| WO | WO 03/084305 | 10/2003 |
| WO | WO 03/105776 | 12/2003 |
| WO | WO 2004/014835 | 2/2004 |
| WO | WO 2005/089744 | 9/2005 |

OTHER PUBLICATIONS

Yamane, M. et al., High-performance liquid chromatography-thermospray mass spectrometry of epoxy polyunsaturated fatty acids and epoxyhydroxy polyunsaturated fatty acids from an incubation mixture of rat tissue homogenate, Journal of Chromatography, B: Biomedical Sciences and Applications, 1994, vol. 652, No. 2, pp. 123-136.

Inhibitory potencies of fish oil hydroxyl fatty acids on cellular lipoxygenases and platelet aggregation, Biochemical Pharmacology, 1991, vol. 42, No. 4, p. 959-962.

"Scope and Editorial Policy", *Organometallics*, published by the American Chemical Society 21 (1) 2002, 13A, 14A.

"Epolinsatures", Bulletin De La Societe Chimique de France, No. 3, pp. 419-432, 1989.

XP002184773. Database WPI, Section Ch, Week 199334. Derwent Publications Ltd., London, GB; AN 1993-269748. (See also JP 05186342, Jul. 27, 1993.).

Alami, et al., A Versatile Route to conjugated hydroxyl (e,z,e,e)—Tetraenoic acids: highly chemo-and stereoselective synthesis of lipoxin B4 Tetrahedro Asym., 8 (17) 1997, pp. 2949-2958.

Albert, C. M. et al., "Blood levels of long-chain n-e fatty acids and the risk of sudden death", *N. Engl. J. Med.*, vol. 346, 2002, pp. 1113-1118.

Arita et al., "Stereochemical Assignment, Antiinflammatory Properties, and Receptor for the Omega-3 Lipid Mediator Resolvin E1", *J. Exp. Med.* 201(5) 2005, 713-722.

Arita, et al., "Resolvin E1, An Endogenous Lipid Mediator Derived from Omega-3 Eicosapentaenoic Acid, Protects Against 2, 4,6-Trinitrobenzene Sulfonic Acid-Induced Colitis", *Proc. Natl. Acad. Sci*, USA, 102(21) 2005, pp. 7671-7676.

Babine, R.E. and S.L. Bender., "Molecular Recognition of Protein-Ligand Complexes: Applications to Design", *Chem. Rev.* 97, 1997, pp. 1359-1472.

Bandeira-Mielo et al., "Cyclooxygenase—2 derived prostaglandin $E_2$ and lipoxin $A_4$ accelerate resolution of allergic edema in Antiostrongylus costaricensis-infected rats: relationship with concurrent eosinophilia", *J. Immunol.*, vol. 164, 2000, pp. 1029-1036.

Bannenberg, et al., "Molecular Circuits of Resolution: Formation and Actions of Resolvins and Protectins", *Immunol.* 174(7) 2005, pp. 4345-4355.

Bazan, et al., "Docosahexaneoic Acid (22:6, n-3) is metabolized to lipoxygenase reaction products in the retina", *Biochem. Biophys. Res. Comm.*, vol. 125, 1984, pp. 741-747.

Bazan et al., "Pathways for the uptake and conservation of docosahexaenoic acid in photoreceptors and synapses: biochemical and autoradiographic studies",*Can. J. Physiol. Pharmacol.*, vol. 71, 1993, pp. 690-698.

Beamer L.J. et al. "Crystal structure of Human BPI and two bound phospholipids at 2.4 angstrom resolution", *Science*, vol. 276, 1997, pp. 1861-1864.

Bhaley, G. et al., "Solid Phase Synthesis of Diverse Tetrahydro-1,4-Benzodiazepine-2-ones", *Tetrahedron Letters* 38(48) 1997, pp. 8375-8378.

Billman et al., "Prevention of sudden cardiac death by dietary pure ω-3 polyunsaturated fatty acids in dogs", *Circulation 99*,1999, pp. 2452-2457.

Blaser, E. et al., "Asymmetrix Steering of oxa Diels-Alder Reactions with Silyloxydienes Employing Proline Esters as Chiral Auxiliary Groups", *Eur. J. Org. Chem.*, 1999, pp. 329-333.

Boland et al.,"Stereospecific Syntheses and Spectroscopis Properties of Isomeric 2,4,6,8-Undecatetraenes. New Hydrocarbons from the Marine Brown Alga Giffordia Mitchellae", *Helv. Chim. Acta* 70, 1987, pp. 1025-1040.

Booyens et al., "Some effects of the essential fatty acids linoleic acid and alpha-linolenic acid and of their metabolites gamma-linolenic acid, arachidonic acid, eicosapentaenoic acid docosahexaenoic acid, and of prostoglandins A1 and e1 on the proliferation of human osteogenic sarcoma cells in culture", *Prostoglandins Leukot. Med.*, vol. 15, 1984, pp. 15-33.

Buchanan et al., "Regulation of endothelial cell and platelet receptor-ligand binding by the 12- and 15-lipoxygenase monohydroxides, 12-, 15-HETE and 13-HODE", Prostaglandins Leukot. Essent. Fatty Acids, 1998, pp. 339-346.

Canny, G. et al., "Lipid mediator-induced expression of bactericidal/permeability-increasing protein (BPI) in human mucosal epithelia", *Proc. Natl. Acad., Sci., USA*, vol. 99, No. 6, 2002, pp. 3902-3907.

Capdevila et al., "The highly stereoselective oxidation of polyunsaturated fatty acids by cytochrome P450BM-3", J. Biol. Chem., 1996, pp. 22663-22671.

Catella-Lawson et al., "Cycloxygenase inhibitors and the antiplatelet effects of aspirin", *N. Engl. J. Med.*, vol. 345, 2001, pp. 1809-1817.

Chiang et al., "Aspirin-triggered 15-epi-lipoxin A4 (ATL) generation by human leukocytes and murine peritonitis exudates: Development of a specific 15-epi-LXA4 ELISA", J. Pharmacol. Exp. Ther., 1998, pp. 779-790.

Chiang et al., "Leukotriene B4 receptor transgenic mice reveal novel protective roles for lipoxins and aspirin-triggered lipoxins in reperfusion", *J. Clin. Invest.*, 1999, pp. 309-316.

Claria et al., "Aspirin triggers previously undescribed bioactive eicosanoids by human endothelial cell-leukocyte interactions", *Proc. Natl. Acad. Sci., USA*, 1995, pp. 9475-9479.

Clish et al., "Oxidoreductases in lipoxin $A_4$ metabolic inactivation", *J. Biol. Chem.*, vol. 375, 2000, pp. 25372-25380.

Colgan, S.P .et al., "Defective in vitro motility of polymorphonuclear leuocytes of homozygote and heterozygote Chediak-Higashi cats", *Vet. Immunol. Immunopathology*, 1992, pp. 205-227.

Colgan et al., "Lipoxin $A_4$ modulates transmigration of human neutrophils across intestinal epithelial monolayers", *J. Clin. Invest.*, vol. 92,1993, pp. 75-82.

Cooper, S.F., et al., "Identification of Antibacterial Fatty Acids from *Phaeodactylum tricomtum* grown in dialysis culture", The Faculty Press, 1985, pp. 28-36.

Corey, E. J. et al., "Docosahexaaenoic acid is a strong inhibitor of prostaglandin but not leukotriene biosynthesis", *Proc. Natl. Acad. Sci. USA*, vol. 80, 1983, pp. 3581-3584.

Crofford. "Rational use of analgesic and anti-inflammatory drugs", *N. Engl. J. Med.*, vol., 345, 2001, pp. 1844-1846.

Cronstein et al., "A mechanism for the anti-inflammatory effects of corticosteriods: The glucocorticoid receptor regulates leukocyte adhesion to endothelial cells and expression of endothelial-leukocyte adhesion molecule 1 and intercellular adhesion molecule 1", Proc. Natl. Acad. Sci. 1992, pp. 9991-9995.

Croset, M. et al., "Inhibition by Lipoxygenase Products of TXA2-Like Responses of Platelets and Vascular Smooth Muscle", Biochemical Pharmacology, vol. 37, No. 7, 1988, pp. 1275-1280, XP002445509.

De Caterina et al., "n-e Fatty Acids and Vascular Disease", *Current Topics in Cardiovascular Disease*, Springer-Verlag, London, 1993.

De Montarby, L. et al., "Syntheses stereoselective de metabolites hydroxyles d'acides gras polyinsatures", Bulletin DeLa Societe Chimique De France, Societe Francaise De Chimie. Paris, FR, No. 3, 1989, pp. 419-432, XP00220024.

Dharmsathaphorn, K. et al., "Established intestinal cell lines as model systems for electrolyte transport studies", *Methods in Enzymology*, vol. 192, 1990, pp. 354-389.

Dioux, Laurent and Morris Srebnik, "Asymmetric Boron-Catalyzed Reactions", *Chem Rev.* 93, 1993, pp. 763-784.

Drazen et al., "Heterogeneity of therapeutic responses in asthma", Br. Med. Bull., vol. 56, 2000, pp. 1054-1070.

Durantel et al., "Study of the mechanism of Antiviral Action of Iminosugar Derivatives against Bovine Viral Diarrhea Virus", *J. Virology* 75 (19) 2001, pp. 8987-8998.

Eckmann, L. et al., "Epithelial cell secrete the chemokines interleukin-8 in response to bacterial entry", *Infection and Immunity*, vol. 61, No. 11, 1993, pp. 4569-4574.

Elsbach, P. et al., "Role of the bactericidal/permeability-increasing protein in host defence", Current Opinion in Immunology, vol. 10, No. 1, 1998, pp. 45-49.

Eritsland et al., "Effects of Highly Concentrated Omega-3 PUF As and Acetylsalicylic Acid, Alone and Combined, on Bleeding Time and Serum Liquid Profile", *J. Oslo City Hosp.*, vol. 39 (8-9) 1989, pp. 97-101.

Evans, B.E. et al., "Design of Nonpetidal ligands for a Peptide Receptor: Cholecystokinin Antagonists", *J. Med. Chem.* 30, 1987, pp. 1229-1239.

Fischer et al., "Uptake, release and metabolism of docosahexaenoic acid (DHA, C22:6w3) in human platelets and neutrophils", *Biochem, Biophys. RES. Commun.*, vol. 120, 1984, pp. 907-918.

Fletcher, M.D. and M.C. Campbell, "Partially Modified Retro-Inverso Peptides: Development, Sythesis, and Conformational Behavior", *Chem. Rev.,* 98, 1998, pp. 763-795.

Fored et al., "Acetaminophen, aspirin, and chronic renal failure", *N. Engl. J. Med.*

Freedman et al., "Characterization of LPS-induced lung inflammation in cftr mice and the effect of docosahexaenoic acid", *J. Appl. Physiol.* vol. 92, 2002, pp. 2169-2176.

Ganz T. et al., "Antimicrobial peptides of phagocytes and epithelia", Seminars in Hematology, vol. 34, No. 4, 1997, pp. 343-354.

Garcia-Cardena et al., "Biomechanical activation of cascular endothelium as a determinant of its functional phenotype", *Proc. Natl. Acad. Sci USA*, vol. 98, 2001, pp. 4478-4485.

Garro-Hellon et al., "Mild and selective Palladium (0)-Catalyzed Deallylation of Allylic Amines, Allylamine and Diallylamines as Very Convenient Ammonia Equivalents for the Synthesis of Primary Amines", *J. Org. Chem.* 58, 1993, pp. 6109-6113.

George et al., "Expression purification and characterization of recombinant human inductible prostaglandin G/H synthase from baculovirus-infected insect cells", Protein Expres. Purif., 1996, pp. 19-26.

Gilroy et al., "Inducible cyclooxygenase may have anti-inflammatory properties", *Nature Med.*, vol. 5, 1999, pp. 698-701.

GISSI-Preventive Investigators, "Dietary supplementation with n-3 polyunsaturated fatty acids and vitamin E after myocardial infarction: Results of the GISSI-Prevenzione trial", *Lancet*, vol. 354, 1999, pp. 447-455.

Golebiowski, A. and J. Jurczak, "Alpha-Amino-Beta-Hydroxy Acids in the Total Synthesis of Amino Sugars", *Synlett*, Apr. 1993, pp. 241-245.

Greeling et al., "Fat intake and fatty acid profile in plasma phospholipids and adipose tissue in patients with Crohn's disease, compared with controls",*Am. J. Gastroenterol.*, vol. 94, 1999, pp. 410-417.

Gronert, et al., "Transcellular regulation of eicosanoid biosynthesis", Eicosanoid Protocols 1999, pp. 119-144.

Guilier et al., "Linkers and Cleavage Stategies in Solid Phase Organic Synthesis and Combinatorial Chemistry", *Chem. Rev.*, 100, 2000, pp. 2091-2157.

Gum et al., "Aspirin use and all-cause mortality among patients being valuated for known or suspected coronary artery disease: a propensity analysis", *J.A.M.A.*, vol. 286, 2001, pp. 1187-1194.

Gunstone et al., "The Lipid Handbook", 2nd Ed., Chapman & Hall, London, 1994, pp. 1-551.

Hanessia, S. et al., "Design and Synthesis of Conformationally Constraines Amino Acids as Versatile Scaffolds and Peptide Manners", *Tetrahedron Lett.*, 53, 1997, pp. 12789-12854.

Herschman, "Recent progress in the cellular and molecular biology of prostaglandin synthesis", *Trends Cardiovasc. Med.*, 1998, pp. 145-150.

Hibbeln, "Fish consumption and major depression", *Lancet*, vol. 351, 1998, p. 1213.

Higuchi, R. et al., "Kinetic PCR analysis: real time monitoring of DNA amplification reactions", Biotechnology, vol. 11, 1993, pp. 1026-1030.

Hill et al., "Trout thrombocytes contain 12-but not 5-lipoxygenase activity", Biochem. Biophys. Acta 1999, pp. 63-70.

Hill, E.M. et al., "Identification and egg hatching activity of monohydroxy fatty acid eicosanoids in the barnacle Balanus balanoides", Proc. R. Soc. London, Ser. B, vol. 247, No. 1318, 1992, pp. 41-46, XP002200247.

Hill, E.M., *Proc R. Soc. London Ser. B.*, 247 (1318) 1992, pp. 41-46.

Hong, et al., "Novel Docosatrienes and 17S-Resolvins Generated from Docosahexaenoic Acid in Murine Brain, Human Blood, and Glial Cells", Autacoids in Anti-Inflammation, *J. Biol. Chem.* 278(17), 2003, pp. 14677-14687.

Hoyng, C.F. and A.D. Patel, "Aldehyde Components for use in Four-Component Condensation ("4CC") UGI Reaction Peptide Synthesis", *Tetrahedron Lett.*, (21) 1980, pp. 4795-4798.

Humphrey, J.M. and A.R. Chamberlin, "Chemical Synthesis of Natural Product Peptides Coupling Methods for the Incorporation of noncoded Amino Acids into Peptides", *Chem. Rev.*, 97, 1997, pp. 2243-2266.

Iacoviello et al., "Modulation of Fibrinolytic Response to Venous Occlusion in Humans by a Combination of Low-Dose Aspirin and n-3 PUFAs", *Arteriosclerosis Thrombosis*, vol. 10, 1992, pp. 1191-1197.

Ikeda et al., "Chiral Allenylboronic Esters as Practical Reagent for Enantioselective Carbon-Carbon Bond formation Facile Synthesis of (-) Ipsenol", *J. Am. Chem, Soc.*, 108, 1986, pp. 483-4486.

Jenski, L.J., et al. "Docosahexaenoic acid-induced alteration of Thy-1 and CD8 expression on murine splenocytes", *Biochim, Biophys. Acta.* 1236, pp. 39-50, 1995.

Karanian, J. et al., "Physiological functions of hydroxy-docosahexaenoic acid", 1992, XP002200246.

Karanian, J.W. et al., "Inhibitory Effects of n-6 and n-3 Hydroxy Fatty Acids on Thromboxane (U46619)-Induced Smooth Muscle Contraction", J. of Pharmacology and Experimental Therapeutics, vol. 270, No. 3, 1994, pp. 1105-1109.

Kato, T. et al., "Production of hydroxy unsaturated fatty acids using crude lipoxygenase obtained from infected rice plants", Bulletin of the Chemical Society of Japan, vol. 69, No. 6, 1996, pp. 1663-1666, XP002200251.

Khair-El-Din et al., "Transcription of the murine INOS gene is inhibited by docosahexanaenoic acid, a major constituent of fetal serum and fish oils diets inhibits IFN alpha-induced Ia-expression by murine macrophases in vitro", *J. Immuno.*, vol. 154, 1995, pp. 1296-1306.

Khair-El-Din, et al. "Transcription of the Murine iNOS Gene is Inhibited by Docosahexaenoic Acid, a Major Constituent of Fetal and Neonatal Sera as Well as Fish Oils", J. Exp. Med., vol. 183, pp. 1241-1246, 1996.

Khalfoun, B. et al., "Docosahexaenoic and Eicosapentaenoic Acids Inhibit Human Lymphoproliferative Responses in Vitro but not the Expression of T cells Surface Activation Markers", Scandinavian J. Immunology, vol. 43, 1996, pp. 248-256, XP0000878923, ISSN: 0300-9475.

Kitajka et al., "The role of n-3 polyunsaturated fatty acids in brain: Modulation of rat brain gene expression by dietary n-3 fatty acids", *Proc. Natl. Acad. Sci.*, USA9, 2002, pp. 2619-2624.

Knapp, Howard R., et al., "Bactericidal Effects of Polyunsaturated Fatty Acids", The Journal of Infectious Diseases, vol. 154, No. 1, 1986, pp. 84-94.

Konig et al., "Synthesis of N-Tert-Alkylglyxolic Acid Amides", *Syntheses*, pp. 1233-1234, (1993), [In German, English language abstract on 1 st page of article].

Lau et al., "Effects of Fish Oil Supplementation on Non-Steroidal Anti-Inflammatory Drug (NSAID) Requirement in Patients with Mild Rheumatoid Arthritis—A Double-Blind Placebo Controlled Study", *British Journal of Rheumatology*, vol. 32 (11), 1993, pp. 982-989.

Lee et al., "Characterization and biologic properties of 5,12-dihydroxy derivatives of eicosapentaenoic acid, including leukotriene B5 and the double lipoxygenase product", J. Biol. Chem., 1984, pp. 2383-2389.

Lee et al., "Effects of exogenous arachidonic, eicosapentaenoic, and docosahexaenoic acids on the generation of 5-lipoxygenase pathway products by ionophore-activated human neutrophils", *J. Clin. Invest.*, vol. 74, 1984, pp. 1922-1933.

Levy et al., "Lipid mediator class switching during acute inflammation: signals in resolution", *Nature Immunol.*, vol. 2, 2001, pp. 612-619.

Levy, "Prostaglandin H synthases, nonsteriodal anti-inflammatory drugs, and colon cancer", FASEB J., 1997, pp. 234-247.

Levy, O. , "A neutrophil-derived anti-infective molecule: bactericidal/permeability-increasing protein", Antimicrobial Agents and Chemotherapy, vol. 44, No. 11, 2000, pp. 2925-2931.

Levy, O., "Antimicrobial proteins and peptides of blood: templates for novel antimicrobial agents", Blood, vol. 96, No. 8, 2000, pp. 2664-2672.

Levy, Bruce D. et al. "Protectin D1 is Generated in Asthma and Dampens Airway Inflammation and Hyperresponsiveness," *The Journal of Immunology*, 2007, 178: 496-502.

Libby, "Atherosclerosis, The New View", *Sci. Am.*, vol. 286, 2002, pp. 46-55.

Ligo, et al., "Inhibitory Effects of Docosahexaenoic Acid on Colon Carcinoma to the Lung", Br. J. Cancer, 1997, pp. 650-655.

Lockhart, D.J. et al., "Expression monitoring by hybridization to high-density oligonucleotide arrays", Nature Biotechnology, vol. 14, No. 13, 1996, pp. 1675-1680.

Loeschke D. et al., *Dig. Dis. Sci.*, vol. 41, 1996, pp. 2087-2094.

Maddox et al., "Lipoxin $A_4$ and $B_4$ are potent stimuli for human monocyte migration and adhesion selective inactivation by dehydrogenation and reduction", *J. Exp. Med.*, vol. 183, 1996, pp. 137-146.

Marcheselli, et al. "Novel Docosanoids Inhibit Brain Ischemia-Reperfusion-Mediated Leukocyte Infiltration and Pro-Inflammatory Gene Expression", *J. Biol. Chem.* 278(44), 2003, pp. 43807-43817.

Marchioli, R. et al., "Early protection against sudden death by n-3 polyunsaturated fatty acids after myocardial infarction: time-course analysis of the results of the Gruppo-Italiano per lo Studion della Sopravivenze nell'Infarto Miocardico", *Circulation*, vol. 105, 2002, pp. 1897-1903.

Marchioloi, "Dietary supplementation with n-3 polyunsaturated fatty acids and vitamin E after myocardial infarction: results of the GISSI-Prevenzione trial", *Lancet* 1999, pp. 447-455.

Marcus, "Platelets: their role in hemostasis, thrombosis, and inflammation", *Inflammation: Basic Principles and Clinical Correlates*, 1999, pp. 77-95.

Martinez et al., "Docohexaenoic acid—a new therapeutic approach to peroxisomal disorder patients: Experience with two cases", *Neurology*, vol. 43, 1993, pp. 1389-1397.

Marx et al., "Synthetic Design for Combinatorial Chemistry. Solution and Polymer-Supported Synthesis of Polycyclic Lactams by Intramoloecular Cyclization of Azomethane Ylides", *J. Chem. Soc.*, 119, 1997, pp. 6153-6167.

Marzo et al., "Biosynthesis of docohexaenoic acid in human cells, evidence that two different—desaturase activities may exist", Biochem. Biophys. Acta 1301, 1996, pp. 263-272.

Mata de Urquiza et al., "Docosahexaenoic acids, a ligand for the retinoid X receptor in mouse brain", *Science*, vol. 290, 2000, pp. 2140-2144.

McCormick, B.A. et al., "*Salmonella typhimurium* attachment to human intestinal epithelial monolayers: transcellular signaling to subepithelial neurophils", *J. Cell Biology*, vol. 123, No. 4, 1993, pp. 895-907.

McLennan et al., "The cardiovascular protective role of the docosahexaenoic acid", *Eur. J. Pharmacol.* vol. 300, 1996, pp. 83-89.

McMahon et al., "Lipoxins: Revelations on Resolution", *Trends in Pharmacological Sciences*, vol. 22, 2001, pp. 391-395.

Mehta et al., "Structure—Activity Relationship of a New Class of Anti-Hepatitis B Virus Agents", *Antimicrobial Agents and Chemotherapy*, 46(12) 2002, pp. 4004-4008.

Miller et al., "Dietary supplementation with ethyl ester concentrates of fish oil (n-3) and borage oil (n-6) polyunsaturated fatty acids induces epidermal generation of local putative anti-inflammatory metabolites", *J. Invest. Dermat.*, vol. 96, 1991, pp. 98-103.

Miller et al., "Oxidative metabolism of dihomogammalinolenic acid by guinea pig epidermis: Evidence of generation of anti-inflammatory products", *Prostaglandins*, vol. 35, 1988, pp. 917-938.

Miller et al., "Guinea Pig Epidermis Generates Putative Anti-Inflammatory Metabolites from Fish Oil Polyunsaturated Fatty Acids", Lipids, Chemical Abstract 24(12), 112: 117062, pp. 998-1003, 1989. Lipids, Chemical Abstract 112:117062, 1989, pp. 998-1003.

Needleman et al., "The discovery and function of COX-2", *J. Rheumatol*, 1997, pp. 6-8.

Nicolaou et al., "Lipoxins and Related Eicosanoids: Biosynthesis, Biological Properties and Chemical Synthesis," *Angew. Chem. Ed. Engl.* 30, 1991, pp. 1100-1116.

Nicolaou et al., "Novel IBX-Mediated Process for the Synthesis of Amino Sugars and Libraries Thereof", *Angew. Chem. Int. Ed. Engl.*, 39, 2000, pp. 2525-2529.

Node et al., "Anti-inflammatory properties of cytochrome P450 epoxygenase-derived eicosanoids", Science, 1999, pp. 1276-1279.

Noyori, R. (Ed), "Enantioselective Addition of Organometallic Reagents to Carbonyl Compounds: Chirality Transfer, Multiplication and Amplification," Chapter 5 in Asymmetriccal Catalysts in Organic Synthesis, New York; Wiley & Sons, Inc., 1994, pp. 225-297.

Nugent, William A., "Chiral Lewis Acid Catalysts. Enantioselective Additon of Azide to Meso Epoxides", *J. Am. Chem. Soc.*, 114(7), 1992, pp. 2768-2769.

O'Banion et al., "Cdna Cloning and functional activity of a glucocorticoid-regulated inflammatory cyclooxygenase",*Proc. Natl., Acad., Sci USA*, vol. 89, 1992, pp. 4888-4892.

O'Donnell, Martin J. and J. Falmagne, "The Synthesis of Amino Acids via Organoboranes", *J. Chem. Soc. Chem. Commun.*, No. 17, Sep. 1, 1985, pp. 1168-1169.

Olfson et al., "National trends in the outpatient treatment of depression", *JAMA*, vol. 287, 2002, pp. 203-209.

Palmantieri, et al., "Transcellular metabolism of arachidonic acid in platelets and polymorphonuclear leukocytes activated by physiological agonists: enhancement of leukotriene B4 synthesis", *Cell-Cell Interactions in the Release of Inflammatory Mediators*, vol. 314, 1991, pp. 73-89.

Petasis, N. A. and I.A. Zavialov, "A New and Practical Syntrhesis of Alpha Amino Acids from Alkenyl Boronic Acids",*J. Am. Chem. Soc.*, 119(2), 1997, pp. 445-446.

Petasis, N. A. and I.A. Zavialov, "The Boronic Acid Mannich Reaction: A New Method for the Synthesis of Geometrically Pure Allylamines", *Tetrahedron Letters*, 34(4)1993, pp. 538-586.

Pfaffl, M.W., "A new mathematical model for relative quantification in real-time RT-PCR", Nucleic Acids Research, vol. 29, No. 9, 2001, pp. 2002-2007.

Poling, et al., "Docosahexaenoic acid block of neuronal voltage-gated K+ channels: subunit selective antagonism by zinc", *Neuropharmacology*, vol. 35, 1996, pp. 969-982.

Pullarkat et al., "Leukocyte docosahexaenoic acid in juvenile form of ceroidlipofuscinosis", *Neuropadiatrie*, vol. 9, 1987, pp. 127-130.

Qiu et al., "Aspirin-triggered lipoxin $A_4$ and lipoxin $A_4$ up-regulate transcriptional corepressor NAB1 in human neutrophils", *FASEB J.* 1096/ fj. 1001-0576fje, 2001, vol. 10.

Rao et al, "Comparative Pharmacology of Cyclooxygenase Inhibitors on Platelet Function", *Prostaglandins Leukot. Med.*, vol. 18 (1), 1985, pp. 119-131.

Rapp et al., "Dietary eicosapentaenoic acid and docosahexaenoic acid form fish oil", *Arteriosclerosis and Thrombosis*, vol. 11, 1991, pp. 903-911.

Reddy et al., "Change in content, incorporation and lipoxygenation of docosahexaenoic acid in retina and retinal pigment epithelium in canine ceroid lipofuscinosis", *Neuroscience Lett.*, vol. 59, 1985, pp. 67-72.

Reich, E.E. et al., "Formation of novel D-ring and E-ring isoprostane-like compounds ($D_4/E_4$—neuroprostanes) in vivo from docosahexaenoic acid", *Biochemistry*, vol. 39, 2000, pp. 2376-2383.

Reynaud et al., *Analytical Biochemistry* (1993), 214(1), pp. 165-170 , CA 119: 265901.

Ridker et al., "Inflammation, aspirin, and the risk of cardiovascular disease in apparently healthy men", N. Engl. J. Med. 1997, pp. 973-979.

Rodriguez and Spur, "Total Synthesis of aspirin-triggered 15-epi-lipoxin A4", *Tetrahedron Letters*, 42, 2001, pp. 6057-6060.

Rolinson et al., "Spatial requirements for 15-(R)-hydroxyl-5Z,8Z,11Z,13E-eicosatetraenoic acid synthesis with the cyclooxygenase active site of murine COX-2", J. Biol. Chem., vol. 275, 2000, pp. 6586-6591.

Rosenberg et al., "Fish-food to calm the heart", *N. Engl. J. Med.*, vol. 346, 2002, pp. 1102-1103.

Rowley et al., "Homeostasis in fish—an evolutionary perspective", *Throm. Homeost.*, vol. 77, 1997, pp. 227-233.

Ruettinger et al., "Epoxidation of unsaturated fatty acids by a soluble cytochrome P-45-dependent system from *Bacillus megaterium*", J. Biol. Chem., 1981, pp. 5728-5734.

Salem, N. et al., "Arachidonic and docosahexaenoic acids are biosynthesized from their 18-carbon precursors in human infants", *Proc. Natl. Acad. Sci USA*, vol. 93, 1996, pp. 49-54.

Samuelson et al., "From studies of biochemical mechanisms to novel biological mediators: prosraglandin endoperoxides, thromboxanes and leukotrienes", *In Les Prix Nobel*, 1982, pp. 165-174.

Samuelson et al., "Leukotrienes and lipoxins: structure, biosynthesis, and biological effects", *Science*, vol. 237, 1987, pp. 1171-1176.

Sawazaki et al., "Lipoxygenation of docosaxaenoic acid by the rate pineal body", *J. Neurochem.*,vol. 62, 1994, pp. 2437-2447.

Schmedtje, Jr. et al., "Hypoxia Induces Cyclooxygenase-2 via the NF- Kb p65 Transcription Factor in Human Vascular Endothelial Cells", *J. Biol. Chem.*, vol. 272, No. 1, 1997, pp. 601-608.

Serhan et al, "Design of lipoxin A4 stable analogs that block transmigration and adhesion of human neutrophils", *Biochemistry*, 1995, pp. 14609-14615.

Serhan et al., "Nomenclature of lipoxins and related compounds derived from arachidonic acid and eicosapentaenoic acid", Prostaglandins ,1987, pp. 201-204.

Serhan et al., "Novel functional sets of lipid-derived mediators with Anti-inflammatory Actions generated from omega-3 fatty acids via cyclooxygenase 2-nonsteroidal anti-inflammatory drugs and transcellular processing", *J. Exp. Med.*, vol. 192, No. 8, 2000, pp. 1197-1204.

Serhan et al., "Resolvins, Docosatrienes, and Neuroprotectins, Novel Omega-3-Derived Mediators, and their Aspirin-Triggered Endogenous Epimers: An Overview of Their Protective Roles in Catabasis", *Prostaglandins Other Lipid Mediat.* 5543, 2004, pp. 1-18.

Serhan et al., "Unorthodox routes to prostanoid formation: new twists in cyclooxygenase-initiated pathways", *J. Clin. Invest.*, vol. 107, 2001, pp. 1481-1489.

Serhan, "A Search for Endogenous Mechanisms of Anti-Inflammation Uncovers Novel Chemical Mediators: Missing Links to Resolution", *Histochem Cell Biol.* 122(4), 2004, pp. 305-321.

Serhan, "Novel Eicosanoid and Docosanoid Mediators: Resolvins, Docosatrienes, and Neuroprotectins", *Curr Opin Clin Nutr Metab Care*, 8(2), 2005, pp. 1-7.

Serhan, "Novel Omega-3-Derived Local Mediators in Anti-Inflammation and Resolution", *Pharmacol. Ther.* 105(1), 2005, pp. 7-21.

Serhan, et al., "Novel Endogenous Small Molecules as the Checkpoint Controllers in Inflammation and Resolution: Entrée for Resoleomics" *Rheum Dis Clin North Am.* 30(1), 2004, pp. 69-95.

Serhan, et al., "Novel functional sets of Lipid-derived mediators with anti-inflammatory actions generated from omega-3 fatty acids via Cyclooxygenase 2-nonsteroidal Anti-inflammatory drugs and transcelllular processing", *J. Exp. Med. Col.* vol. 192, 2000, pp. 1197-1204.

Serhan, et al., "Novel Pathways and Endogenous Mediators in Anti-Inflammation and Resolution", *Chem Immunol Allergy*, 83, 2003, pp. 115-145.

Serhan, et al., "Resolvins, Docosatrienes and Nueroprotectins, Novel Omega-3 Derived Mediators and their Endogenous Aspirin-Triggered Epimers", Lipids, vol. 39, 2004, pp. 1125-1132.

Serhan, et al., "Resolvins: a family of bioactive products of omega-3 fatty acids transformation circuits initiated by aspirin treatment that counter proinflammation signals", *J. Exp. Med.*, vol. 196, No. 8, 2002, pp. 1025-1037.

Serhan, et al. "Resolvins, Docosatrienes, and Neuroprotectins, Novel Omega-3-Derived Mediators, and their Endogenous Aspirin-Triggered Epimers", *Lipids*, 73: 155-172, 2004.

Sethi et al., "Inhibition of phagocyte-endothelium interactions by oxidized fatty acids: A natural anti-flammatory mechanism?", J. Lab. Clin. Med., 1996, pp. 27-38.

Shimizu, T. et al., "Enzyme with dual lipooxygenase activities catalyzes luekotriene $A_4$ synthesis from arachidonic acid", *Proc. Natl. Acad Sci. USA*, vol. 81, 1994, pp. 689-693.

Shinmura et al., "Cyclooxygenase-2 medaites the cardioprotectie effects of the late phase of ischemic preconditioning in conscious rabbits", *Proc. Natl. Acad. Sci. USA*, vol. 97, 2000, pp. 10197-10202.

Simopoulos, "Workshop on the essentiality of an recommended dietary intakes for omega-6 and omega-3 fatty acids", *J. Am. Coll. Nutr.*, 1999, pp. 487-489.

Srivastava, "Docosahexaenoic acid (C22:6w3) and linoleic acid are anti-aggregatory, and alter arachodonic acid metabolism in human platelets", *Prostaglandins Leukot. Med.*

Takeshi Terano, Ensho, Chemical Abstract 107:22439, 1987, pp. 63-71.

Takeshi Terano et al., "Eicosapentaenoic acid and docosahexaenoic acid inhibit vascular smooth muscle cell proliferation by inhibiting phosphorylation of Cdk2-cyclinE complex", *Biochem. Biophys. Res. Comm.*, vol. 254, pp. 502-506.

Taylor, C.T. et al., "Critical role of cAMP response element binding protein expression in hypoxia-elicited induction of epithelial tumor necrosis factor-a", J. Biol. Chem., vol. 274, No. 27, 1999, pp. 19447-19454.

Thompson, L.A. and J.A. Ellman, "Synthesis and Applications of Small Molecule Libraries", *Chem. Rev.*, 96, 1996, pp. 555-6000.

Tou, "Acylation of docosahexaenoic acid into phospholipids by by intact human neutrophils", *Lipids*, vol. 21, 1986, pp. 324-327.

Van Dyke, et al., "Resolution of Inflammation: A New Paradigm for the Pathogenesis of Periodontal Diseases", *J. Dent. Res.*, 82(2) 2003, pp. 82-90.

Vane et al., "Therapeutic Roles of Selective COX-2 Inhibitors", *William Harvey Press*, London, 2001.

VanRollins et al., "Autooxidation of docosahexaenoic acid: Analysis of ten isomers of hydroxydocosahexaenoate", *J. Lipid Res.*, vol. 25, 1984, pp. 507-517.

VanRollins et al., "Oxidation of docosahexaenoic acid by rat liver microsomes", *J. Biol. Chem.*, vol. 259, 1984, pp. 5776-5783 (CA 101:19194).

Vu Bois et al., "Novel, Stereoselcetive Synthesis of 2 Amino Saccharides", *J. Am. Chem. Soc.* 119, 1997, pp. 3179-3180.

Waki, M. and J. Meienhofer, "Peptide Synthesis Using the Four-Component Condensation (Ugi Reaction)," *J. Am. Chem. Soc.*, 99., 1997, pp. 6075-6082.

W.E.M. Lands, "Proceedings of the AOCS Short Course on Polyunsaturated Fatty Acids and Eicosanoids", American Oil Chemists' Society, 1987.

Weersink, A., et al., "Human granulocytes express a 550-kDa lipopolysaccharide-binding protein on the cell surface that is identical to the bactericidal/permeability-increasing protein", *J. Immunology*, vol. 150, No. 1, 1993, pp. 253-263.

Weiss, J. et al., "Purification and characterization of a potent bactericidal and membrane active protein from the granules of human polymorphonuclear leukocytes", *J. Biol. Chem.*, vol. 253, No. 8, 1987, pp. 2664-2672.

Weissmann, "Aspirin", *Sci Am.*, 1991, pp. 84-90.

Whelan et al., "The unique characteristics of the purified 5-lipoxygenase from potato tubers and the proposed mechanism of formation of leukotrienes and lipoxins", *Biological Oxidation Systems*, vol. 2, 1990, pp. 765-778.

Xiao et al., "Analysis of hydroperoxide-induced tyrosyl radicals and lipoxygenase activity in aspirin-treated human prostaglandin H synthase-2", Biochemistry, 1997, pp. 1836-1845.

Yamamoto, Y. and N. Asao, "Selective Reactions Using Allylic Metals", *Chem Rev.*, 93, 1993, pp. 2207-2293.

Yamane, M. et al., "Docosahexaenoic/arachiconic acid omega-hydroxylation system and differentiation in the human colonic adenocarcinoma cell line, Caco-2", Cancer Letters, vol. 122, 1998, pp. 51-59, XP002200245.

Yergey et al., "High-performance liquid chromatography/thermospray mass spectrometry of eicosanoids and novel oxygenated metabolites of docosahexaenoic acid", *Anal. Chem.*, vol. 58, 1986, pp. 1344-1348.

Yokomizo et al., "A G-protein-coupled receptor for leukotriene B4 that mediates chemotaxis", Nature, 1997, pp. 620-624.

Zeldin, "Epoxygenase pathways of arachidonic acid metabolism", *J. Biol. Chem.*, vol. 276, 2001, pp. 36059-36062.

Ziboth et al., "Inhibition of sheep vesicular gland oxygenase by unsaturated fatty acids from skin of essential acid deficient rats", *Prostaglandins*, 1974, vol. 5, pp. 233-240.

Ziboth et al., "Metabolism, of polyunsaturated fatty acids by skin epidermal enzymes: generation of anti-inflammatory and antiproliferative metabolites", Am. J. Clin. Nutr., vol. 71 (Suppl.), 2000, p. 361S-366S.

Chemical Abstracts online citation, AN:2004:143088, retrieved Aug. 15, 2007, from STN, Columbus, OH.

Hong, et al. "Rainbow trout (oncorhynchus mykiss) brain cells biosynthesize novel docasahexaenoic acid-derived resolvins and protectins—mediator lipidomic analysis", *Prostaglandins & Other Lipid Mediators*, Elsevier, vol. 78, No. 1-4, Jun. 13, 2005, pp. 107-116. XP005174168.

Serhan, Charles N. et al. "Anti-Inflammatory Actions of Neuroprotectin D1/Protectin D1 and it's Natural Stereoisomers: Assignments of Dihydroxy-Containing Docosatrienes", Journal of Immunology, 176(3), 1848-1959 Coden: J01MA3; ISSN 0022-1767, Feb. 1, 2006. XP002429095.

PCT/US2006/038326 International Search Report dated Apr. 23, 2007.

PCT/US2006/000306 International Search Report dated Jul. 14, 2006.

PCT/US2003/25336 International Search Report dated Feb. 16, 2004.

PCT/US2001/05196 International Search Report dated Jul. 19, 2002.

EP 06 02 2386 European Search Report dated Oct. 5, 2007.

PCT/US2005/12552 International Search Report dated Aug. 24, 2005 (in name of Trustees of Boston University).

PCT/US2006/011222 International Search Report dated Oct. 5, 2007.

PCT/US2005/009056 International Search Report dated Nov. 16, 2005.

Slots, et al., "General Health Risk of Periodontal Disease", International Dental Journal, Dec. 2001, 51(6), pp. 417-422.

Green, Gary A., "Understanding NSAIDS: From Aspirin to COX-2", Clinical Cornerstone, Sports Medicine 2001, 3(5), pp. 50-59.

MERCK Index, "Gingivitis", Copyright © 1995-2007 Merck & Co., Inc., Whitehouse Station, NJ, USA, Last Full Version, Feb. 2003, 3 pgs.

Stella, Valentino J., "Expert Opinion of Therapeutic Patents", Prodrugs as Therapeutics, 2004, 14(3), pp. 277-280.

Wolff et al., "Burger's Medicinal Chemistry and Drug Discovery", $5^{th}$ Ed., vol. 1, pp. 975-977, 1994.

Dragoli et al., "Parallel Synthesis of Prostaglandin $E_1$ Analogues", J. Comb. Chem., 1999, pp. 534-539.

A

A

Figure 7
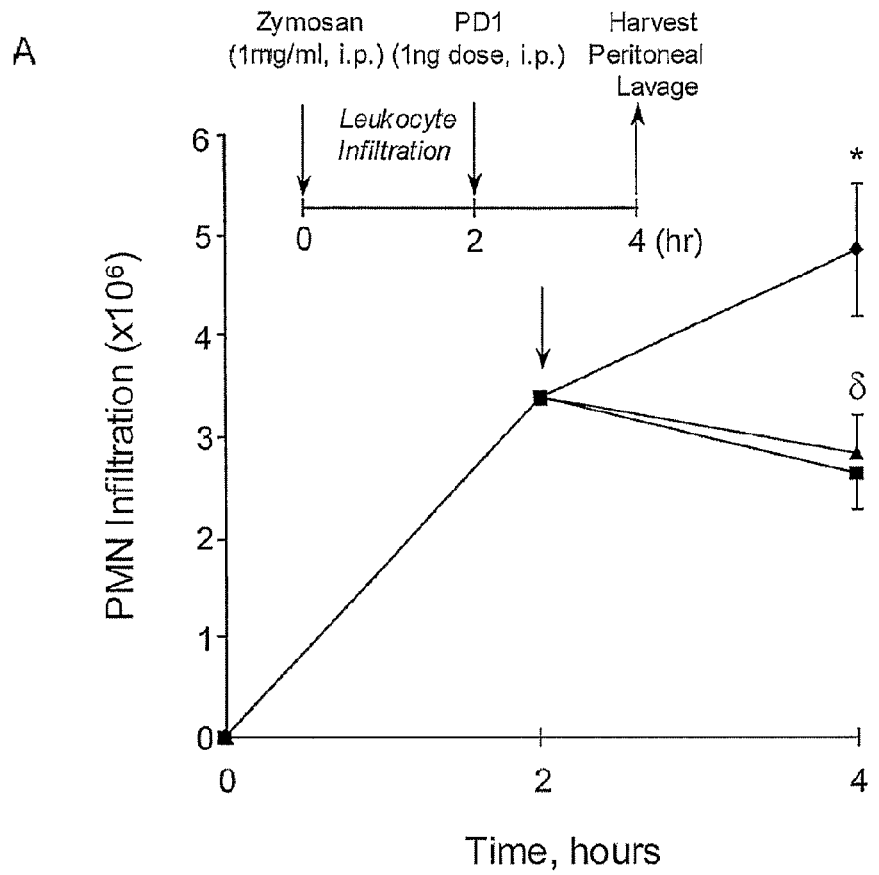
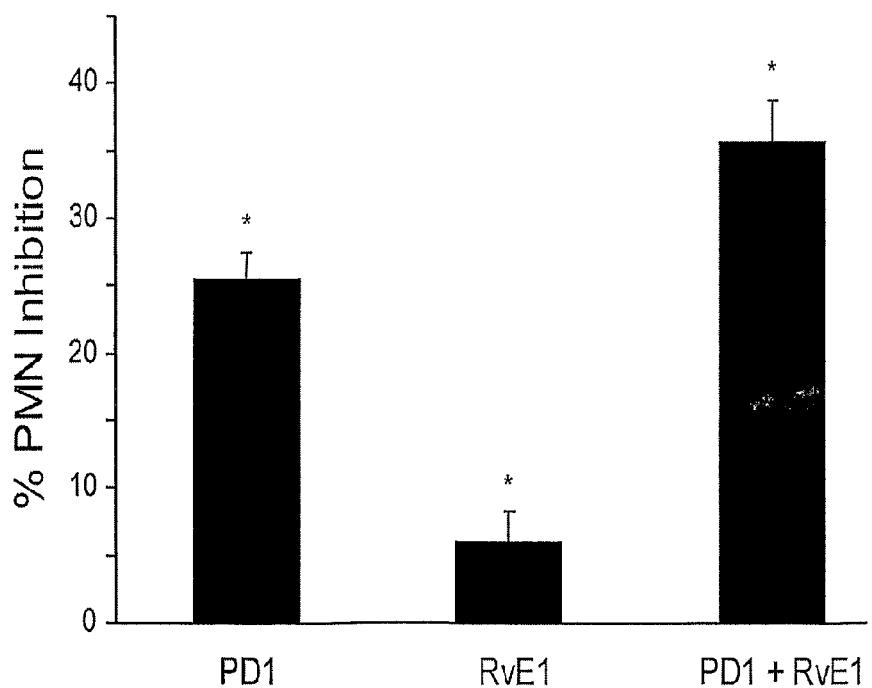

Fig. 8

| Compound | LC/MS RT | LC/MS Major Ions a | GC/MS Major Ions b | UV λmax c |
|---|---|---|---|---|
| 10,17S,-dihydroxy-docosa-4Z,7Z,11,13,15,19Z-hexaenoic-acid | 32.9 | 359; 341; 315; 297; 277; 245; 217; 181; 153 | 518; 503; 449; 351; 261; 171; 129; 73 | 270 nm shoulders 260;279 nm |
| 10S,17S,-dihydroxy-docosa-4Z,7Z,11E,13E,15Z,19Z-hexaenoic-acid | 30.2 | 359; 341; 315; 297; 277; 245; 217; 181; 153 | 518; 503; 449; 351; 261; 171; 129; 73 | 271 nm shoulders 264,281 nm |
| 10R,17S,-dihydroxy-docosa-4Z,7Z,11E,13E,15Z,19Z-hexaenoic-acid | 32.9 | 359; 341; 315; 297; 277; 245; 217; 181; 153 | 518; 503; 449; 351; 261; 171; 129; 73 | 271 nm shoulders 262;282 nm |
| 10S,17R,-dihydroxy-docosa-4Z,7Z,11E,13E,15Z,19Z-hexaenoic-acid | 32.9 | 359; 341; 315; 297; 277; 245; 217; 181; 153 | 518; 503; 449; 351; 261; 171; 129; 73 | 271 nm shoulders 260;279 nm |

Continuation of Fig. 8

| Compound | | | | |
|---|---|---|---|---|
| 10R,17S,-dihydroxy-docosa-4Z,7Z,11E,13Z,15E,19Z-hexaenoic-acid | 35.0 | 359; 341; 315; 297; 277; 245; 217; 181; 153 | 518; 503; 449; 351; 261; 171; 129; 73 | 269 nm shoulders 260;280 nm |
| 10R,17S,-dihydroxy-docosa-4Z,7Z,11E,13E,15E,19Z-hexaenoic-acid | 25.0 | 359; 341; 315; 297; 277; 245; 217; 181; 153 | 518; 503; 449; 351; 261; 171; 129; 73 | 269 nm shoulders 260;281 nm |
| 10S,17S-dihydroxy-docosa-4Z,7Z,11E,13Z,15E,19Z-hexaenoic-acid | 30.2 | 359; 341; 315; 297; 277; 245; 217; 181; 153 | 518; 503; 449; 351; 261; 171; 129; 73 | 269 nm shoulders 258;280 nm |

[a]LC-MS/MS was performed with a Finnigan LCQ liquid ion trap tandem mass-spectrometer equipped with a LUNA C18-2 (150 x 2mm x 5μm) column and a UV diode array detector using an isocratic mobile phase (MeOH:H2O:AcOH at 65:35:0.01) with a 0.2 ml/min flow rate.

[b]GC-MS was performed with a Hewlett-Packard 6890 equiped with a HP 5973 mass.detector. A HP5MS cross-linked 5% ME siloxane column (30 cm x 0.25 mm x 0.25μm) was employed with a temperature program; the intial temperature was 150°C, followed by 230°C (2 min), and 280°C (10 min) with a helium flow rate of 1.0 ml/min. Trimethylsilyl derivatives were prepared with each compound following treatment with diazomethane.

[c]Spectra were recorded in methanol using a Hewlett-Packard 8453 UV spectrophotometer with ±2 nm accuracy.

Fig. 9

Table II. Leukocyte Infiltration in Murine Peritonitis: Actions of PD1 and Chemically Stable Analog

| Injection | Number of leukocytes present $\times 10^6$ | | |
|---|---|---|---|
| | Neutrophils | Monocytes | Lymphocytes |
| Zymosan A | 9.22 ± 0.47 | 2.54 ± 0.15 | 0.15 ± 0.11 |
| Zymosan A + PD1 | 5.93 ± 0.62*δ (35.7% ↓) | 4.43 ± 0.62*δ (74.4% ↑) | 0.33 ± 0.13 (120% ↑) |
| Zymosan A + 15,16-dehydro-PD1 | 6.18 ± 0.80*δ (33.0% ↓) | 3.79 ± 0.53 (49.3% ↑) | 0.42 ± 0.11 (180% ↑) |

Peritonitis was carried out as in Experimental Procedures but extended to 4 h. Mice were injected with 10ng/mouse of either PD1 (n = 3) or 15,16-dehydro-PD1 (n = 4) followed by 1 mg of zymosan A. Leukocyte infiltration was determined 4 h after injection. Results are expressed as mean ± SEM, and percent inhibition of neutrophils and stimulation of monocytes as compared to mice injected with zymosan A (1 mg) alone. Statistically different from *zymosan A-injected mice ($p<0.05$) but not between δ PD1 and 15,16-dehydro-PD1-injected mice ($p>0.05$).

Fig. 10

Table I. Characteristics of Subjects*

|  | Healthy | Asthma Exacerbation |
|---|---|---|
| Sample size (n) | 3 | 4 |
| Age (yrs) | 28 +/- 1 | 41 +/- 6 |
| M:F | 1:2 | 2:2 |
| Race | 3 other | 2 Caucasian, 1 African American, 1 other |
| Current cigarette smoker | 0 | 2 |

*EBC was collected from individuals in the emergency department with an acute asthma exacerbation and a control group of healthy subjects (see Methods). Plus-minus values are means +/- SD.

Fig. 12
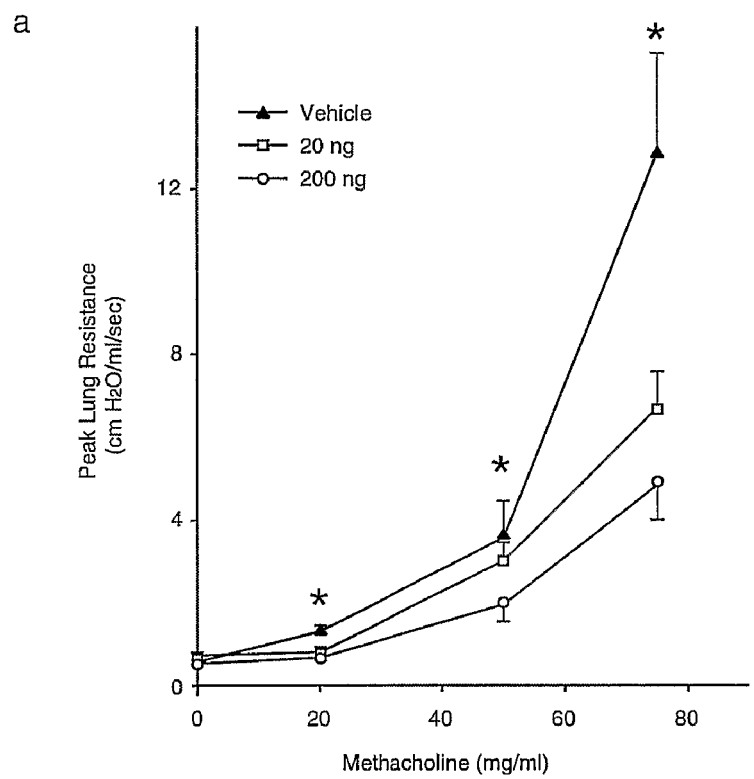
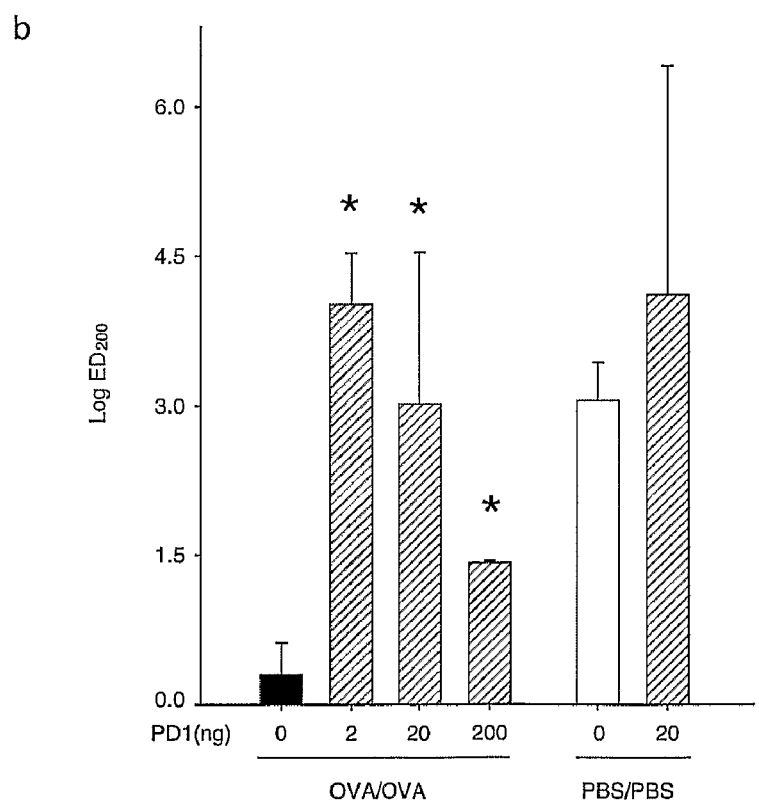

Fig. 16
a  PD1 200 ng
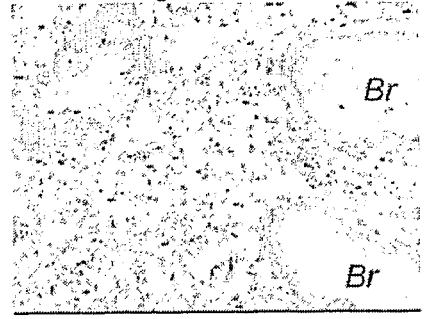
b  PD1 20 ng
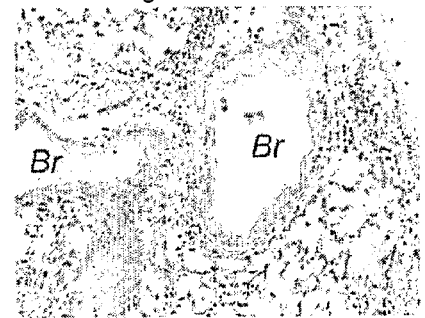
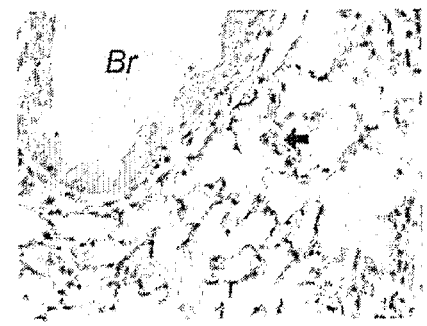
c  PD1 2 ng
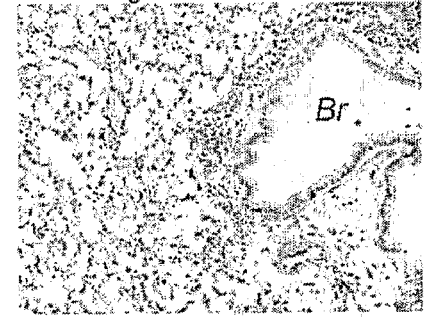
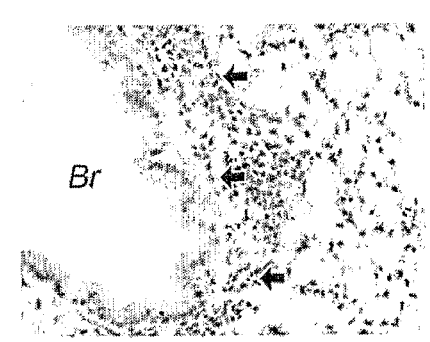
d  vehicle
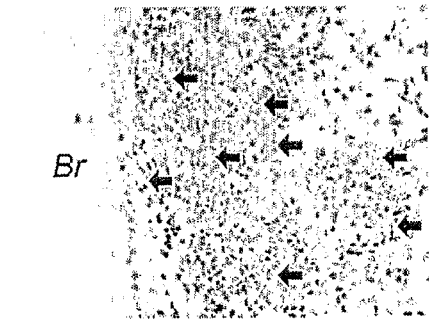
20x                                                                 40x

ANTI-INFLAMMATORY ACTIONS OF NEUROPROTECTIN D1/PROTECTIN D1 AND IT'S NATURAL STEREOISOMERS

CROSS REFERENCE TO RELATED APPLICATIONS

This application claims benefit under 35 U.S.C. §119(e) to U.S. Ser. Nos. 60/723,052, filed Oct. 3, 2005, entitled "Anti-Inflammatory Actions of Neuroptectin D1/Protectin D1 and Its Natural Stereoisomers" and 60/749,786, filed Dec. 13, 2005, entitled "Anti-Inflammatory Actions of Neuroptectin D1/Protectin D1 and Its Natural Stereoisomers", the contents of both are incorporated herein by reference in their entirety.

STATEMENT REGARDING FEDERALLY SPONSORED RESEARCH

The work leading to this invention was supported in part by National Institutes of Health (NIH) grants GM38765, P50-DE016191, HL068669 and AI068084. The U.S. Government therefore may have certain rights in the invention.

FIELD OF THE INVENTION

Protectin D1, neuroprotectin D1 when generated by neural cells, is a member of a new family of bioactive products generated from docosahexaenoic acid (1-3). The complete stereochemistry of protectin D1 (10,17S-docosatriene), namely chirality of the carbon 10 alcohol and geometry of the conjugated triene, required for bioactivity remained to be assigned. To this end, PD1 generated by human neutrophils during murine peritonitis and neural tissues was separated from natural isomers and subject to LC-MS-MS and GC-MS. Comparisons with six 10,17-dihydroxydocosatrienes prepared by total organic and biogenic synthesis showed that PD1 from human cells carrying potent bioactivity is 10R,17S-dihydroxy-docosa-4Z,7Z,11E,13E,15Z,19Z-hexaenoic acid. Additional isomers identified included trace amounts of Δ15-trans-PD1 (isomer III), 10S,17S-dihydroxy-docosa-4Z,7Z,11E,13Z,15E,19Z-hexaenoic acid (isomer IV), and a double dioxygenation product 10S,17S-dihydroxy-docosa-4Z,7Z,11E,13Z,15E,19Z-hexaenoic acid (isomer I), present in exudates. $^{18}O_2$ labeling showed that 10S,17S-diHDHA (isomer I) carried $^{18}O$ in the 10-position alcohol, indicating sequential lipoxygenation, whereas PD1 formation proceeded via an epoxide. PD1 at 10 nM attenuated (~50%) human neutrophil transmigration while Δ15-trans-PD1 was essentially inactive. PD1 was a potent regulator of PMN infiltration (~40% at 1 ng/mouse) in peritonitis. The rank order at 1-10 ng dose was PD1≈PD1 methyl ester>>Δ15-trans PD1>10S,17S-diHDHA (isomer I). 10S,17S-dihydroxy-docosa-4Z,7Z,11E,13E,15Z,19Z-hexaenoic acid (isomer VI) proved ≧PD1 in blocking PMN infiltration but was not a major product of leukocytes. PD1 also reduced PMN infiltration after initiation (2 h) of inflammation and was additive with resolvin E1. These results indicate that PD1 is a potent stereoselective anti-inflammatory molecule.

BACKGROUND OF THE INVENTION

The resolution of inflammation is a central component of host defense and the return of tissue to homeostasis (4). It is recognized that inflammation plays a key role in many prevalent human diseases including cardiovascular diseases, atherosclerosis, Alzheimer's disease, and cancer (5-7). Although much is known about the molecular basis of initiating signals and proinflammatory chemical mediators in inflammation, it has only recently become apparent that endogenous stop signals are critical at early checkpoints within the temporal events of inflammation (8). In this context, lipid mediators are of interest. The arachidonic acid-derived prostaglandins and leukotrienes are potent pro-inflammatory mediators (9), whereas their cousins, the lipoxins, biosynthesized from arachidonic acid, are potent anti-inflammatory and proresolving molecules (for reviews see 10, 11, 12). During the course of inflammation, arachidonate-derived eicosanoids switch from prostaglandins and leukotrienes within inflammatory exudates to lipoxins that in turn stop the recruitment of neutrophils to the site. This switch in eicosanoid profiles and biosynthesis is driven, in part, by cyclooxygenase-derived prostaglandin $E_2$ and prostaglandin $D_2$, which instruct the transcriptional regulation of enzymes involved in lipoxin biosynthesis (13). Hence, the appearance of lipoxins within inflammatory exudates is concomitant with spontaneous resolution of inflammation (13), and these chemical mediators are non-phlogistic stimulators of monocyte recruitment and macrophage phagocytosis of apoptotic PMN (14, 15)

Further studies on the endogenous mechanisms of anti-inflammation using a murine model of spontaneous resolution demonstrated, for the first time, that resolution is an active biochemical process that involves the generation of specific new families of lipid mediators (for recent reviews, see refs. 16, 17). During spontaneous resolution, cell-cell interactions and transcellular biosynthesis lead to the production of these new families of potent bioactive lipid mediators from ω-3 essential fatty acid precursors and were termed resolvins (resolution phase interaction products derived from DHA and EPA) and protectins (docosatrienes derived from DHA) ((1, 3, 18) and recently reviewed in (19)). These novel di- and trihydroxy-containing products from EPA and DHA that are generated by previously unrecognized enzymatic pathways display potent anti-inflammatory and immunoregulatory actions in vitro and in vivo in murine models of acute inflammatory actions (1, 3, 18).

In 1929, the omega-3 polyunsaturated fatty acids were assigned essential roles because their exclusion from the diet gave rise to a new form of deficiency disease (20). Many recent reports document the importance of fish oil (omega-3) fatty acids EPA and DHA in human diseases associated with inflammation. In particular, omega-3 DHA and EPA are protective in inflammatory bowel disease and colitis (21), cardiovascular disease (22-25), and Alzheimer's disease (26). However, the molecular mechanisms responsible for these documented beneficial actions of omega-3 fatty acids remain an important challenge. DHA is enriched in neural tissues, where it appears to play functional as well as structural roles (27, 28). Along these lines, results from earlier studies indicated that DHA was enzymatically converted to products coined docosanoids that might be linked to retinal protection (29) and neuronal function (30). The structures of the molecules involved, however, were not established.

Human whole blood isolated leukocytes, and glial cells enzymatically convert DHA to 17S-hydroxy-containing docosatrienes and 17S-series resolvins (1, 3). The novel 10,17S-docosatriene, first identified in ref. (3) and its basic structure established, displayed potent anti-inflammatory actions, i.e., reducing PMN numbers in exudates in vivo, and down regulating production of proinflammatory cytokines by glial cells in vitro (1). During the resolution phase of peritonitis, unesterified DHA levels increase within exudates and 10,17S-docosatriene is generated within the resolving exudates, where it appears to promote catabasis, or the return to homeostasis, by shortening the resolution interval (31). Of special interest, this DHA-derived 10,17S-docosatriene is generated in vivo during strokes in murine tissues and limits the entry of leukocytes into the area of neural damage, reducing the magnitude of tissue injury (32). It was found that 10,17S-docosatriene is neuroprotective in retinal pigmented cells and introduced the term neuroprotectin D1 for this potent compound (2), which accumulates in the ipsilateral hemisphere of the brain following focal ischemia (33).

Recent results indicate that neuroprotectin D1 is formed from DHA in cornea in a lipoxygenase-dependent fashion to protect from thermal injury as well as promote wound healing (34). It is noteworthy that neuroprotectin D1, resolvin D1, and resolvin D5 are all produced by trout brain cells from endogenous DHA, suggesting that the structures of these DHA-derived mediators are conserved from fish to humans (35). Together, these recent findings underscore the need to establish the complete stereochemistry of endogenous biologically active 10,17S-docosatriene, namely its carbon 10 position alcohol chirality and double bond geometry of its conjugated triene system. In recognition of its wide scope of formation and actions, protectin D1 (PD1) is used to denote the structure of this chemical mediator and the prefix neuro before protectin D1 is used to note its tissue origin and address. Here, the complete stereochemistry of protectin D1 and its related natural isomers (i.e., Δ15-trans-PD1) as well as their anti-inflammatory properties are reported.

Therefore, a need exists for additional understanding of how other polyunsaturated compounds and biological derivative may provide insight into such complex biological pathways.

BRIEF SUMMARY OF THE INVENTION

The present invention surprisingly provides methods to isolate, substantially purify (purify) and prepare compounds such as: I 10S,17S-dihydroxy-docosa-4Z,7Z,11E,13Z,15E, 19Z-hexaenoic acid; II 10R,17S-dihydroxy-docosa-4Z,7Z, 11E,13E,15Z,19Z-hexaenoic-acid; V 10S,17R,-dihydroxy-docosa-4Z,7Z,11E,13E,15E,19Z-hexaenoic-acid; III 10R, 17S-dihydroxy-docosa-4Z,7Z,11E,13E,15E,19Z-hexaenoic-acid; IV 10R,17S-dihydroxy-docosa-4Z,7Z,11E, 13Z,15E,19Z-hexaenoic-acid; and VI 10S,17S-dihydroxy-docosa-4Z,7Z,11E,13E,15E,19Z-hexaenoic-acid. Also, derivatives such as esters, e.g., methyl esters, of the acids can be prepared and show biological activity as discussed herein.

Additionally, the 15,16-dehydro-PD1 provides a chemically stable system that also has biological activity.

In other aspects, the invention provides 10,17-dihydroxy-docasa-hexaenoic acids having the general formula (VII):

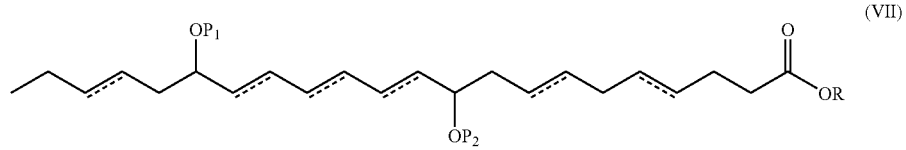

wherein R is a hydrogen atom, an alkyl group, or is a pharmaceutically acceptable salt and each of $P_1$ and $P_2$, individually, is a hydrogen atom or a protecting group. The dashed line represents that the double bond can be "cis" or "trans" in configuration. In certain aspects, compounds I, II, IV, V and VI, each independently of each other, are excluded from the invention.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed descriptions are to be regarded as illustrative in nature and not restrictive.

BRIEF DESCRIPTION OF THE DRAWINGS

FIG. 7: PD1 actions in vivo. A) PD1 treatment during the course of acute inflammation reduces PMN infiltration. Peritonitis was induced in 6-8-week-old male FVB mice (Charles River Laboratories) by peritoneal injection of 1 mg of zymosan A (♦) as in FIG. 6. Synthetic compound PD1 (▲; cf. FIG. 1) free acid or its synthetic carboxy methyl ester (■) each at 1 ng dose/mouse were injected by peritoneal injection i.p. 2 h after zymosan A-initiated peritonitis. 4 h after induction of peritonitis, rapid peritoneal lavages were collected, and cell-type enumeration was performed. * p<0.05, δ p<0.05, from zymosan plus vehicle alone. B) PD1 and RvE1 have additive anti-inflammatory actions in vivo. Mice were injected i.p. with 10 ng/mouse of either PD1, RvE1, or both, and exudates were collected at 2 h. *p<0.05.

FIG. 8: provides physical attributes of several of the novel compounds.

FIG. 9: provides leukocyte infiltration in Murine Peritonitis.

FIG. 10: provides characteristics of test subjects.

FIG. 12: Lung histopathology from mice given PD1. Mice were sensitized and aerosol challenged with OVA in the presence of PD1 ((a), 200 ng, (b), 20 ng, (c), 2 ng) or (d), vehicle. Representative (n≧3) lung tissue sections (magnifications: ×20 (left column), ×40 (right column)) were obtained from fixed, paraffin-embedded lung tissue, prepared and stained with hematoxylin and eosin. Arrows denote representative EOS; Br, bronchus; v, vessel.

FIG. 16: PD1 reduces airway hyper-responsiveness. (a), OVA sensitized mice were treated with PD1 20 ng (□), 200 ng (○) or vehicle (▲) prior to OVA aerosol challenge. Airway reactivity was determined by methacholine-dependent change in peak lung resistance. Results are expressed as mean±SEM (n≧5). *P<0.05 by one-way ANOVA compared to control animals. (b), ED$_{200}$ was determined for methacholine-dependent changes in mean lung resistance for OVA-sensitized animals receiving PD1 (0, 2, 20 or 200 ng) prior to OVA aerosol challenge and for control animals receiving buffer (PBS) instead of OVA during sensitization and challenge phases of the model. *P<0.05 by Student's t-test compared to control animals.

DETAILED DESCRIPTION

Figure 1:
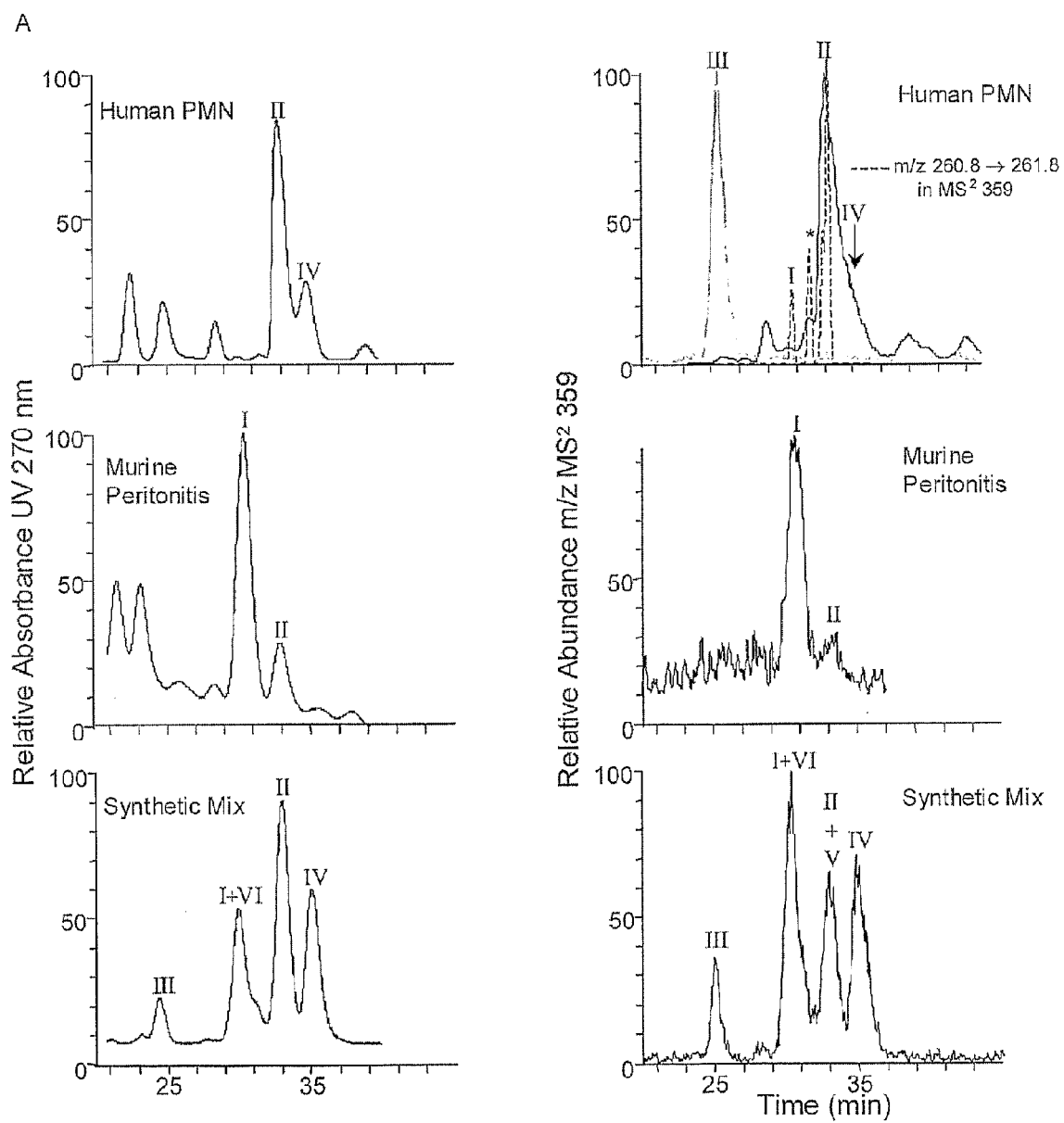
FIG. 1: Panel A: LC-MS-MS profiles and chromatographic behavior of related isomers. Left panels: LC chromatograms plotted at UV absorbance 270 nm; right panels: corresponding MS profiles obtained for m/z MS-MS 359. Upper inserts: representative profiles from human PMN. Right: plotted at $MS^2$ m/z=359; another incubation plotted at m/z 261 of the $MS^2$ 359. The position of synthetic III is shown for comparison. Middle: Murine exudate profiles and lower: profiles obtained for a mixture of related synthetic isomers I-VI (see FIG. 2 for structures). Note that isomers I and VI and II and V coelute in this HPLC system (also see FIG. 8 and text). Panel B: MS-MS Spectrum of PD1 obtained from murine peritonitis. The LC retention time was 32.9 min for the recorded spectrum. Panel C: MS-MS spectrum of synthetic PD1. Panel D: GC-MS spectrum of derivatized PD1. MS obtained following treatment with diazomethane and trimethylsilane. See FIG. 8 and methods section for NMR data and conditions of analysis using LC-MS-MS and GC-MS.
Figure 1:
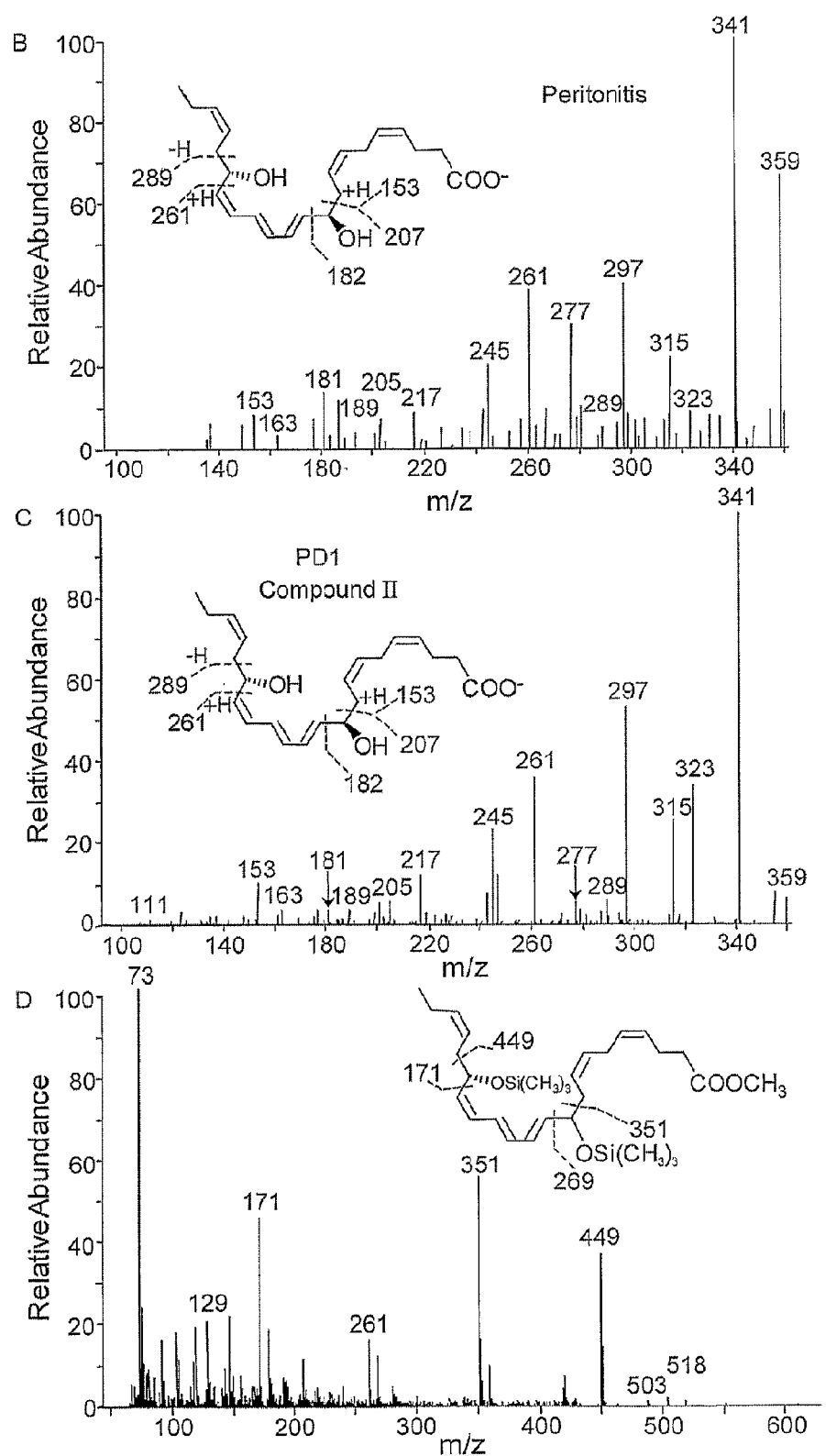

Abbreviations used are:
ω-3 PUFA, omega-3 polyunsaturated fatty acid;
5S,15S-diHETE, 5S,15S-dihydroxy-6E,8Z,11Z,13E-eicosatetranoic acid;
7S,17S-diHDHA, 7S,17S-dihydroxy-docosa-4Z,8E,10Z, 13Z,15E,19Z-hexaenoic acid (resolvin D5);
10S—HDHA, 10S-hydroxy-docosa-hexaenoic acid;
10S,17S-docosatriene, 10S,17S-dihydroxy-docosa-4Z, 7Z,11E,13Z,15E,19Z-hexaenoic acid (the dioxygenation product);
10,17-docosatriene isomers, 10R,17S-dihydroxy-docosa-4Z,7Z,11E,13E,15Z,19Z-hexaenoic acid; 10R,17S-dihydroxy-docosa-4Z,7Z,11E,13E,15E,19Z-hexaenoic acid; 10R,17S-dihydroxy-docosa-4Z,7Z,11E,13Z,15E,19Z-hexaenoic acid; 10S,17R-dihydroxy-docosa-4Z,7Z,11E, 13E,15Z,19Z-hexaenoic acid; 10S,17S-dihydroxy-docosa-4Z,7Z,11E,13E,15Z,19Z-hexaenoic acid;

17S—HDHA, 17S-hydroxy-docosa-4Z,7Z,10Z,13Z,15E, 19Z-hexaenoic acid; 7S—H(p)DHA, 17S-hydroxy(peroxy)-docosa-4Z,7Z,10Z,13Z,15E,19Z-hexaenoic acid;

BAL, bronchoalveolar lavage;
COX-2, cyclooxygenase 2;
CysLT, cysteinyl leukotriene;
DHA, C22:6, docosahexaenoic acid;
EBC, exhaled breath condensate;
EOS, eosinophil;
GC-MS, gas chromatography mass spectrometry;
HMEC, human micro-vascular endothelial cells;
LC-UV-MS-MS, liquid chromatography-ultraviolet-tandem mass spectrometry;
LO, lipoxygenase;
LT, leukotriene;
LX, lipoxins;
Lymph, lymphocyte;
MS, mass spectrometry;
PD1, protectin D1/neuroprotectin D1,10R,17S-dihydroxy-docosa-4Z,7Z,11E,13E,15Z,19Z-hexaenoic acid (when generated in neural tissues the prefix neuro is added, hence neuroprotectin D1 or NPD1 as in ref. 2);
PMN, polymorphonuclear leukocytes;
RP-HPLC, reverse-phase high performance liquid chromatography; and
RvE1, resolvin E1,5S,12R,18R-trihydroxy-6Z,8E,10E,14Z,16E-eicosapentaenoic acid.

Neuroprotectin D1/protectin D1 (10,17-docosatriene) is a potent bioactive lipid mediator derived from DHA that displays anti-inflammatory actions (1, 3) and is generated during the resolution phase of an acute inflammatory response (31). The basic structure of this novel potent DHA-derived mediator was determined, i.e., 10,17-dihydroxydocosatriene (1, 3, 37); its potent role in neural protection was recently uncovered (2) and thus it is denoted as neuroprotectin D1 (NPD1) when produced in neural tissues. Given the importance of establishing the molecular basis of endogenous anti-inflammation and natural resolution (17), as knowledge of these pathways and mechanisms in vivo may provide new therapeutic approaches to human disease, evidence was sought for the complete stereochemistry of PD1. On the basis of physical, biosynthetic, and biological properties in matching results with human cells and synthetic materials, the complete stereochemistry of PD1 was assigned 10R,17S-dihydroxy-docosa-4Z,7Z,11E,13E,15Z,19Z-hexaenoic acid (Compound II; FIGS. 1, 2, and 6A and FIG. 8).

On identification of 10,17-diHDHA in resolving inflammatory exudates (3, 37) and potent anti-inflamatory actions, it was critical to establish its biosynthesis from DHA. To address this, isolated human PMN, whole blood, microglial cells, and murine exudates and tissues (1, 3) were studied. The isolation and identification of alcohol trapping products indicated the involvement of an epoxide intermediate in the conversion of DHA to 10,17S-diHDHA, a docosatriene containing a characteristic conjugated triene structure involving three of the six double bonds present in this compound. The role of a 16(17)epoxide intermediate generated from the 17S-hydroperoxy-DHA precursor was further supported by the identification of two vicinal diols, i.e., 16,17S-dihydroxy-docosatrienes present in these LC-MS-MS profiles also generated from DHA (1). The 16(17)epoxy-DHA intermediate could open via non-enzymatic hydrolysis to a racemic mixture, i.e., 16R/S,17S-diHDHA, or to a single 16,17S-vicinol alcohol by the actions of an appropriate epoxide hydrolase in a reaction similar to that demonstrated earlier in the biosynthesis of $LXA_4$ (39, 44, 46). The biosynthesis of PD1 by human cells (Compound II) with this stereochemistry from a 16(17)epoxide intermediate would require an enzymatic reaction to move the double bond configuration to set the triene geometry to 11E,13E,15Z and direct the attack of $H_2O$ and insertion of its oxygen into the carbon 10 position of PD1 determined in the present experiments to be in the 10R stereochemical configuration.

In addition to PD1 (Compound II) in human cell extracts, which carried potent bioactions, an isomer 10S,17S-diHDHA (Compound I) was also identified in murine exudates with lesser amounts in isolated human cells (FIG. 1). Compound I was found to be a double dioxygenation product and was also formed from DHA but in a reaction that required two sequential lipoxygenation steps and oxygen incorporation that was directed at the 10 position derived from molecular oxygen (i.e., $^{18}O_2$ in an enriched atmosphere in vitro). This reaction producing 10S,17S-diHDHA is markedly different from the proposed enzymatic hydrolysis of the epoxide intermediate in mammalian tissues to produce PD1. The double dioxygenation product formed in vivo is different from PD1 in three key ways: i) PD1 carbon 10 position alcohol is predominantly in the 10R configuration while the dioxygenation product is mainly in the 10S configuration; ii) the double bond structure of PD1 conjugated triene is in the 11E,13E,15Z configuration; the 10S,17S-dioxygenation product conjugated triene system is in the 11E,13Z,15E configuration; iii) most importantly, PD1 is more potent than the dioxygenation product; PD1 (Compound II)>>10S,17S-diHDHA (Compound I); and iv) PD1 is generated by isolated human leukocytes and tissues.

Figure 2:
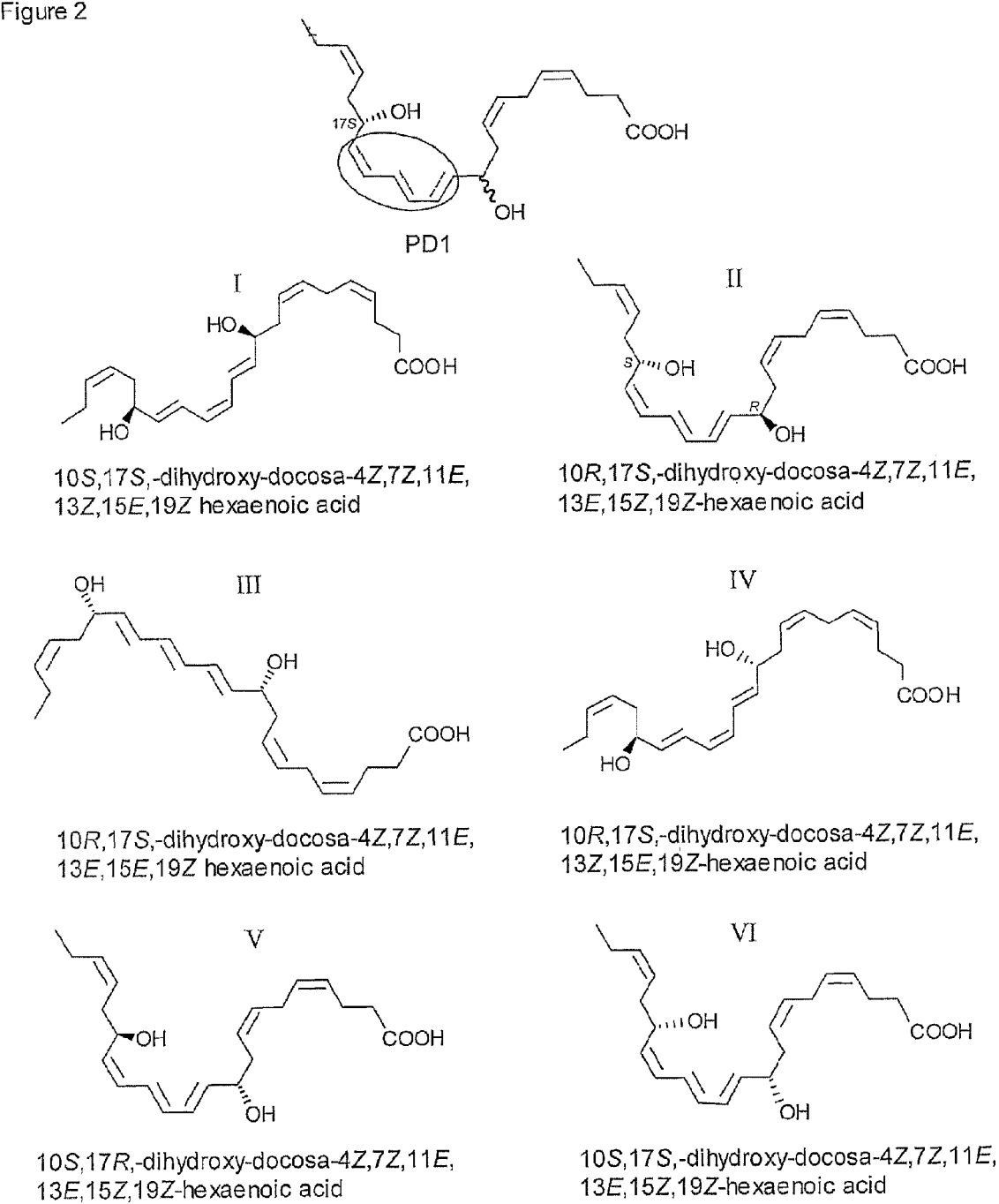
FIG. 2: PD1 and related 10,17-diHDHA isomers. List of compounds prepared and used for the present experiments. PD1 obtained from biological tissues and incubations was identified earlier (1) as a potent bioactive product generated from DHA possessing the 10,17S-dihydroxy-docosatriene structure with a conjugated triene unit between carbons 10 and 17. As denoted, the configuration of the carbon 10 alcohol and double bonds of the conjugation remained to be determined; see text for details and Methods for the NMR values obtained for each of the isomers prepared by total organic synthesis.
Figure 5:
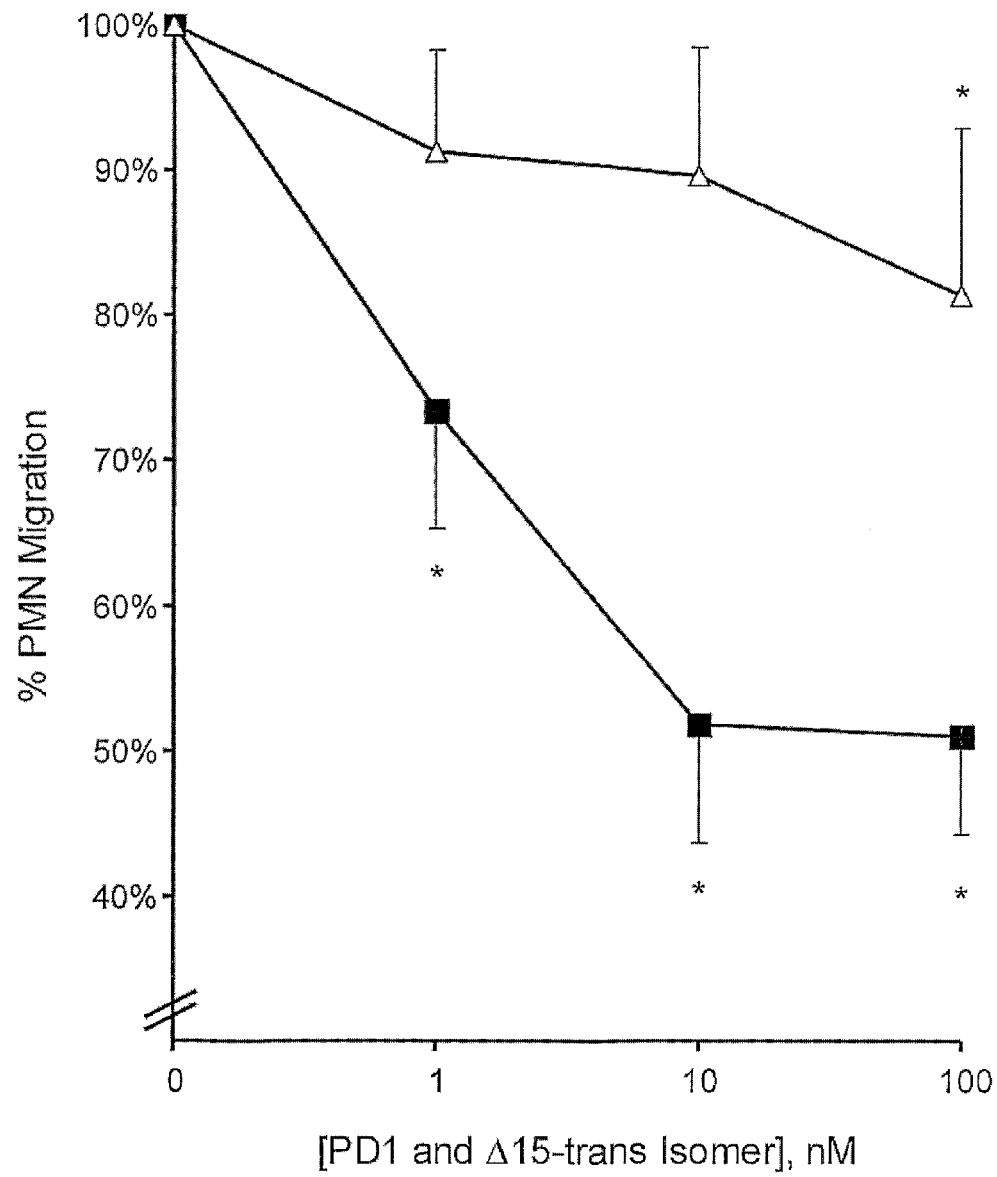
FIG. 5: PD1 blocks human PMN transmigration across endothelial cells. PD1, but not its Δ15-trans-PD1 isomer, inhibited $LTB_4$-induced PMN migration across microvascular endothelial monolayers. Neutrophils ($10^6$ per monolayer) were exposed to vehicle containing buffer or at the indicated concentrations of compound for 15 minutes (see Methods). Neutrophils were then layered on HMEC monolayers and stimulated to transmigrate by addition of $10^{-8}$ M LTB$_4$ for 90 min at 37° C. Transmigration was assessed by quantitation of the PMN marker myeloperoxidase. PD1 represents the mean±SEM percent migration of neutrophils compared to vehicle-treated neutrophils for 9 separate donors and experiments, each performed in triplicate. The results with Δ15-trans PD1 isomer are the mean±SEM obtained for 6 separate PMN donors where each point was also in triplicate. * denotes p<0.01.
Figure 6:
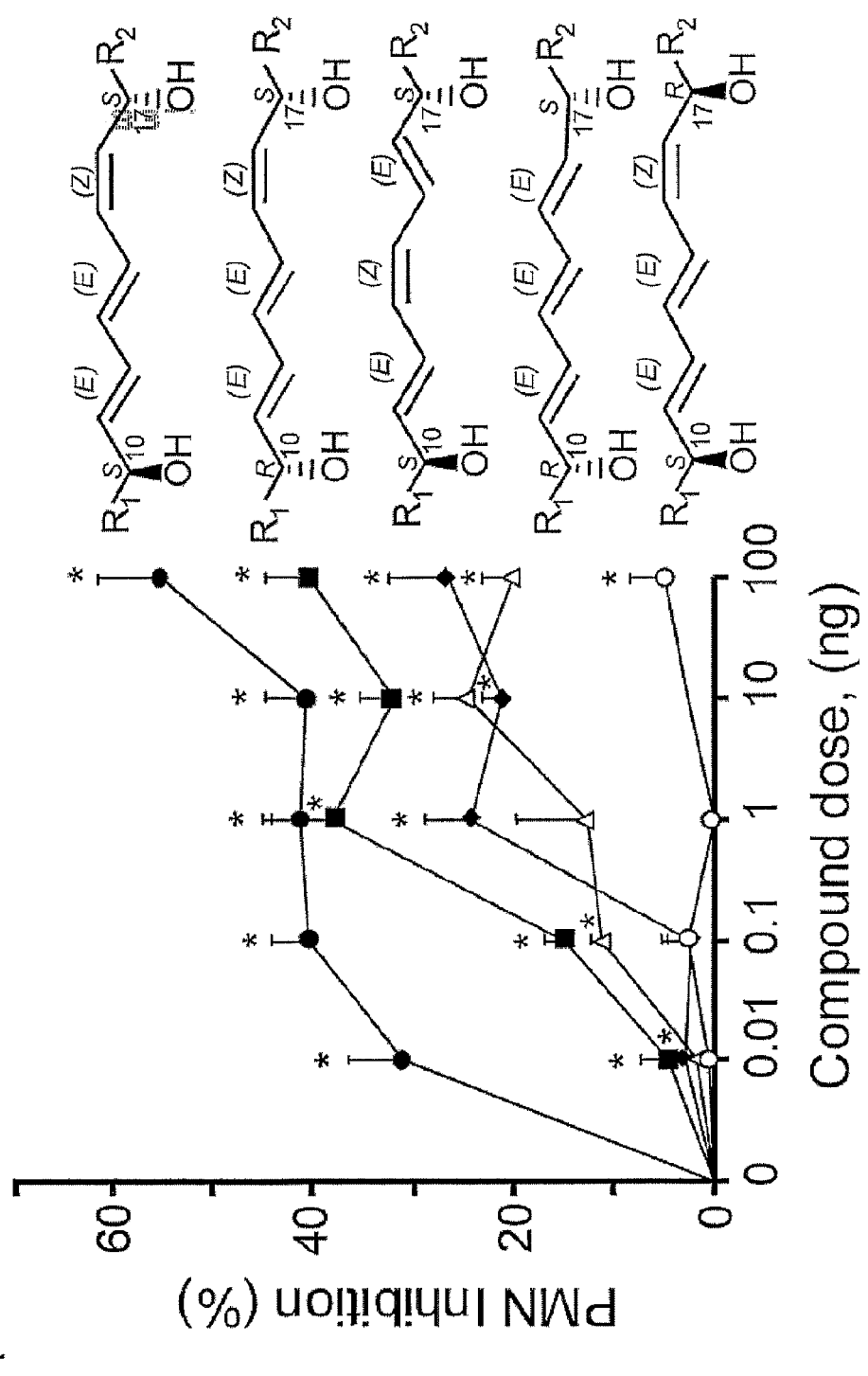
FIG. 6: Dose-dependent inhibition of acute inflammation in vivo with synthetic PD1 and its isomers. Peritonitis was initiated in 6-8-week-old male FVB mice (Charles River Laboratories) by peritoneal injection of 1 mg of zymosan A. Mice were injected with (Panel A): the double dioxygenation product 10S,17S-diHDHA (Compound I, FIG. 2), synthetic PD1 (Compound II), Δ15-trans-PD1 (Compound III), the 10S,17R-diHDHA isomer (Compound V), Compound VI, or vehicle alone. *p<0.05; n≧3 for each compound. n≧7 for PD1 and n≧4 for Compound I. Panel B: PD1, PD1 methyl ester, or the isomer (Compound VI) methyl ester. Peritoneal lavages were obtained at 2 h and leukocytes enumerated. Results are expressed as percent inhibition compared to mice injected with zymosan A (1 mg) and vehicle alone. * p<0.05; n≧4 for each compound.
Figure 6:
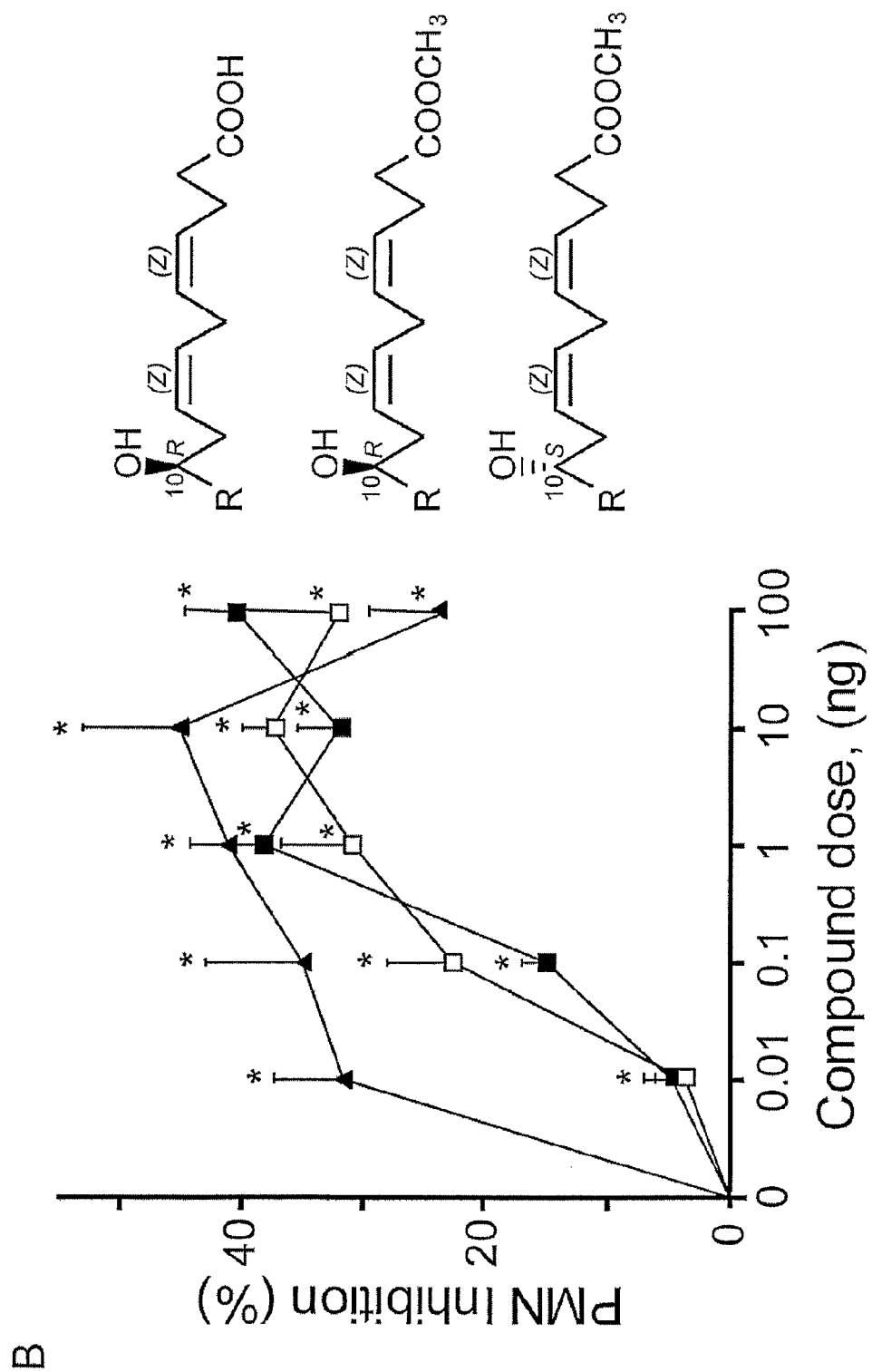

Also in support of the stereospecific basis of these DHA-derived products in human and murine systems is the bioaction of the Δ15-trans-PD1 isomer (Compound III), which can arise via workup-induced isomerization of PD1 and possesses little bioactivity in vitro or in vivo within the dose or concentration range (FIG. 5) observed with biogenic or synthetic PD1 (FIGS. 6 and 7). Also, Compound IV, identified in human leukocytes (FIG. 1) and which differed from Compound I at the 10R position and carried the same double bond geometry, was essentially equipotent at a 1 ng dose (FIG. 2). Hence, the biosynthesis of PD1 from DHA, from the results of the present experiments, appears to require stereoselective enzymatic steps to evoke bioactions. This requirement for stereoselective enzymatic reactions is widely appreciated in the biosynthesis of eicosanoids (9, 44). The nature of the PD1 epoxide hydrolase in vivo is therefore of interest, particularly in view of the bioactivity results with Compound VI, which was the most potent of the isomers (FIG. 6). Compound VI shares the triene geometry of PD1, differing only in the C10 chirality in the S configuration. However, only trace amounts of this isomer appear to be generated by human cells (vide infra). Thus the fidelity of the enzyme that produces PD1 from the proposed carbonium cation intermediate (1) in its ability to direct insertion of $H_2O$-derived alcohol at carbon 10 exclusively in the 10R with apparently trace amounts of 10S as in Compound VI (FIGS. 2 and 6) is an intriguing point for further studies.

Earlier results indicated that DHA, which is not a natural substrate for potato 5-lipoxygenase, is converted to 10-HDHA by this enzyme and the double dioxygenation product 10,20-diHDHA (47). In addition, Whelan et al. demonstrated that this plant lipoxygenase is very versatile with DHA as a substrate (48) and identified multiple monohydroxy-DHA products at carbon positions 4, 7, 8, 11, 13, 14, 16, 17 to give positional isomers of HDHA; each was an enzymatic product of this flexible enzyme. This regioselectivity also likely reflects the degree of enzyme purity as well as the geographic source of the potato. It was found that potato 5-LOX and soybean 15-lipoxygenase gave specific diHDHA profiles of products that were dependent on pH, enzyme, and substrate concentrations used in the incubations (3). When the substrates were presented in micellar configuration with the enzymes, hydroperoxy intermediates were converted to epoxides that, on hydrolysis, gave many of the isomers as relatively minor products but were nonetheless in quantities useful for in vitro and in vivo studies (37). These findings were advantageous in the preparation of intermediates (i.e., 7,17-diHDHA, 17S—HDHA, and 17S—H(p) DHA) used in biosynthesis studies and determining the identity and actions of enzymatic products generated in vivo as well as by isolated human cells from DHA (1, 3).

Recently, the chirality of the DHA potato 5-LOX product 10-HDHA, originally reported (47) by J. Whelan and C. Reddy in 1988, was established as 10S—HDHA by classic steric analysis, and the formation of 10,20-diHDHA and 17-H(p)DHA were reportedly optimized for the plant lipoxygenases (49). In the present studies, the double dioxygenation product prepared, matched, and identified in both suspensions of human PMN (see FIG. 1A, m/z 261 profile) and in vivo during peritonitis carries its alcohols as expected in the 10S,17S configuration in this diHDHA (Compound I). Hence, this natural isomer of PD1 (Compound II) formed in vivo from DHA has its Δ13 position double bond in the cis configuration (i.e., 13Z) and its Δ11 in the trans configuration within the conjugated triene portion of the molecule (11E, 13Z,15E) and possesses some anti-inflammatory activity in vivo, albeit proved to be much less potent than natural or synthetic PD1 (Compound II). The human and murine enzymes(s) involved in the biosynthesis of 10S,17S-diHDHA, the dioxygenation product, have not been determined.

Figure 4:
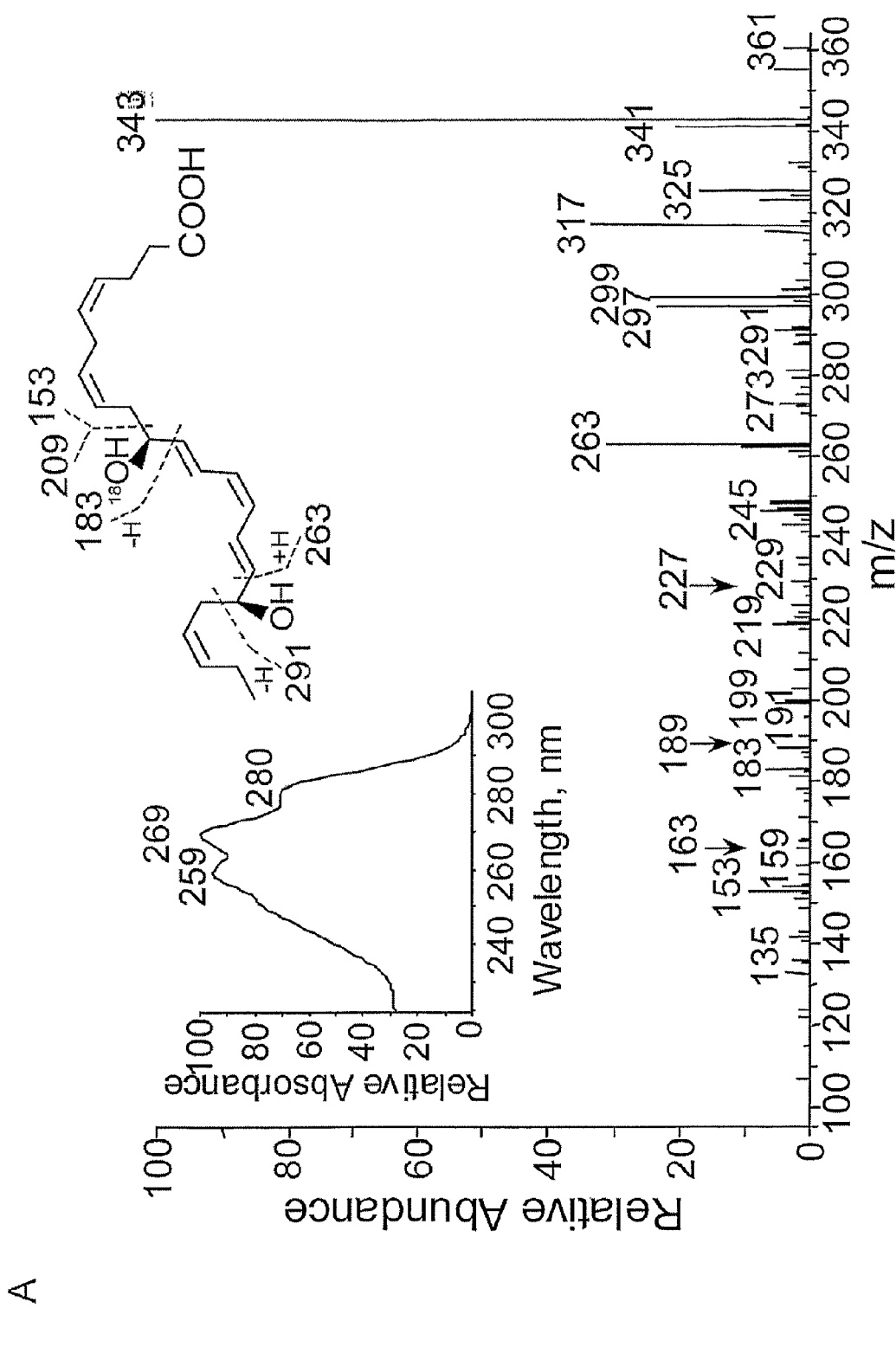
FIG. 4: PD1 and related double dioxygenation products. Panel A: MS-MS of the 10S,17S-diHDHA (isomer I, FIG. 2) carrying $^{18}O$ obtained from incubations enriched in $^{18}O_2$ atmosphere. The substrate was 17S—H(p)DHA; hence, the 17 position alcohol retained the $^{16}O$ and remained unlabeled while both the carbon 7 and 10 position alcohols were labeled from $^{18}O_2$. Fragments carrying $^{18}O_2$ were increased in m/z+2. Panel B: Scheme for PD1 enzymatic formation: epoxidation versus dioxygenation for production of its natural isomer. See text for details.
Figure 4:
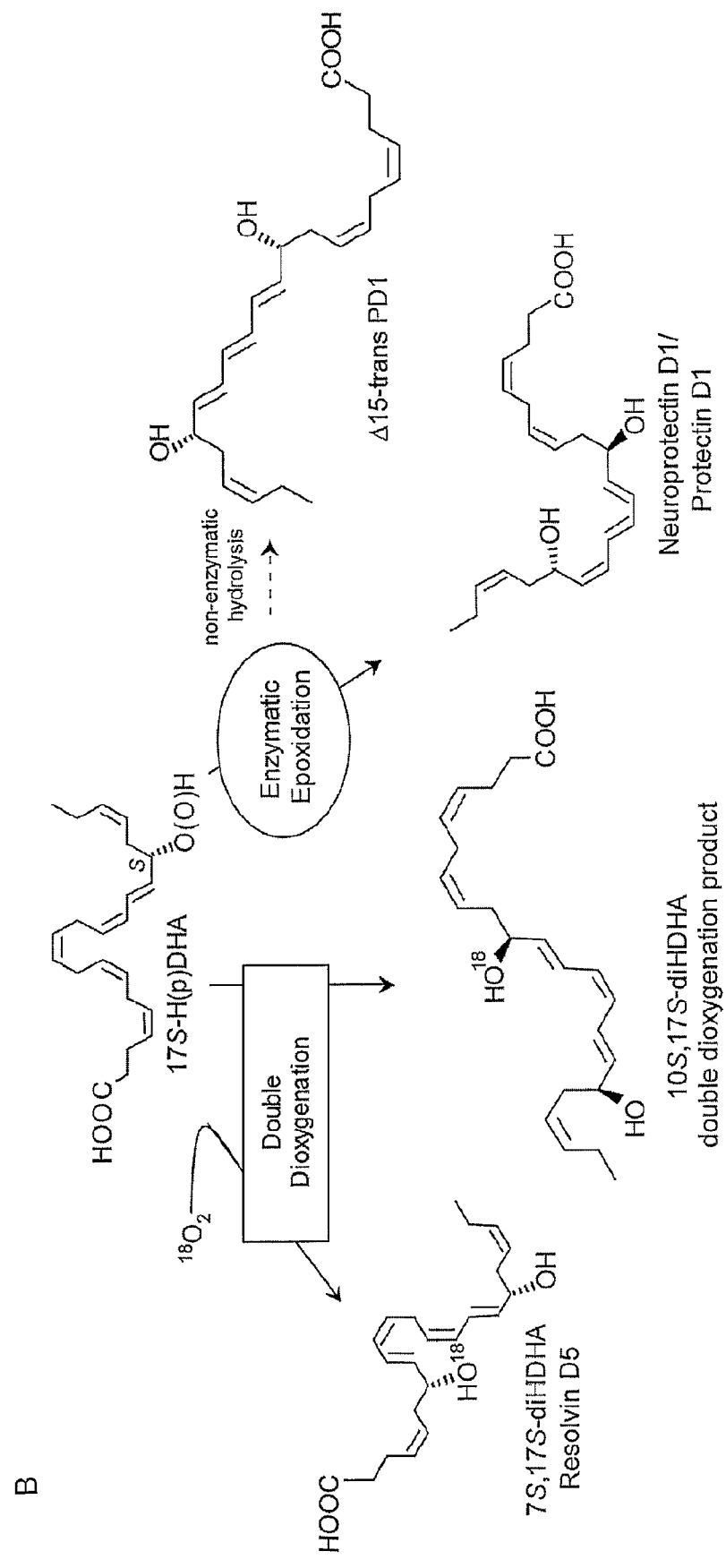

In peritonitis, PD1 significantly reduced PMN infiltration at doses as low as 100 ng/mouse that reached an apparent maximal response at ~50% range (1). This level of inhibition of PMN infiltration may be related to PD1's endogenous anti-inflammatory roles in physiologic settings and thus relevant in dampening PMN infiltration in inflammation as a natural mechanism rather than complete inhibition of PMN transmigration, an event that in theory could lead to immune suppression of microbial host defense mechanisms. In the present studies, it was confirmed that 7,17-diH(p)DHA (1, 3) and 10,17-diH(p)DHA (49) are both double dioxygenation products (see FIG. 4). $^{18}$O was incorporated at the carbon 10-position alcohol that originated from enriched atmosphere molecular $^{18}O_2$ via a lipoxygenase mechanism (FIG. 4A). The evidence for $^{18}$O incorporation at carbon 10 position includes the 2 amu increase in prominent ions in the mass spectrum of 10,17-diHDHA, e.g., m/z 299, 263, 183, 343 (cf FIGS. 1B and C) that was obtained with either 17S—H(p) DHA or 17S—HDHA as substrates. The 10-position alcohol results from lipoxygenation and with native DHA as sequential actions of lipoxygenase(s) (FIG. 4B), since the chirality at the 10-position is likely in predominantly the S configuration (Compound I), the remainder in the 10R configuration as in Compound IV. (see ref. 1).

In peritonitis, PD1 significantly reduced PMN infiltration at doses as low as 100 ng/mouse that reached an apparent maximal response at ~50% range (1). This level of inhibition of PMN infiltration may be related to PD1's endogenous anti-inflammatory roles in physiologic settings and thus relevant in dampening PMN infiltration in inflammation as a natural mechanism rather than complete inhibition of PMN transmigration, an event that in theory could lead to immune suppression of microbial host defense mechanisms. In the present studies, it was confirmed that 7,17-diH(p)DHA (1, 3) and 10,17-diH(p)DHA (49) are both double dioxygenation products (see FIG. 4). $^{18}$O was incorporated at the carbon 10-position alcohol that originated from enriched atmosphere molecular $^{18}O_2$ via a lipoxygenase mechanism (FIG. 4A). The evidence for $^{18}$O incorporation at carbon 10 position includes the 2 amu increase in prominent ions in the mass spectrum of 10,17-diHDHA, e.g., m/z 299, 263, 183, 343 (cf FIGS. 1B and C) that was obtained with either 17S—H(p) DHA or 17S—HDHA as substrates. The 10-position alcohol results from lipoxygenation and with native DHA as sequential actions of lipoxygenase(s) (FIG. 4B), since the chirality at the 10-position is likely in predominantly the S configuration (Compound I), the remainder in the 10R configuration as in Compound IV.

At the 1 ng/mouse dose, 10S,17S-diHDHA (Compound I) did display some activity but this activity did not increase with higher doses in a statistically significant fashion. Also, this double dioxygenation isomer 10S,17S-diHDHA (Compound I) was not active at the 0.1 ng dose compared to PD1. Given the double bond geometry determined in the present study for the conjugated triene unit of PD1 as Δ11E,13E,15Z and 10-position alcohol in the R configuration (FIGS. 1 and 2 and FIG. 8), it is likely that, once the 16(17)-epoxide intermediate is produced from 17S—H(p)DHA (1), it is enzymatically subject to hydrolysis. This opens attack of the proposed cation intermediate by water-derived oxygen rather than molecular oxygen in vivo to give the 10R configuration and set the triene double bond configuration to trans, trans, cis geometry at Δ11E,13E,15Z in PD1. This enzymatic mechanism is also supported by identification of epoxide-derived alcohol trapping products in human leukocytes and glial cells and the isolation and identification of two vicinal diols as minor hydrolysis products, namely 16,17-dihydroxydocosatrienes (see ref. 1). Further studies are warranted to identify the enzyme(s) and establish their role in PD1 biosynthesis as noted above.

In earlier experiments, when administered i.v., 10,17S-docosatriene (PD1, Compound II, FIG. 2) was found to be more potent than indomethacin in reducing PMN infiltration in murine peritonitis, i.e., ~40% inhibition at 100 ng/mouse (1). Synthetic PD1 in as small a dose as 1 ng/mouse gave ~40% inhibition of PMN infiltration that was maintained at the ng and 100 ng doses. Thus, synthetic PD1 (Compound II) matched with the natural compound is a potent regulator of PMN infiltration in vivo but does not completely block PMN recruitment, which is consistent with its counterregulatory and autacoid actions and apparently would not compromise host defense via immune suppression of effector cell function. This was also the case with human PMN transmigration, which required 10-100 nM PD1 to reduce PMN transmigration by 35-45% in vitro. Thus, although PD1 stereoselectively reduces PMN transmigration in vitro, given its potent actions in vivo, PD1 (Compound II) likely targets additional cell types in vivo to evoke its potent anti-inflammatory actions in vivo (FIG. 7 and FIG. 9). In murine peritonitis, PD1 also regulated both monocyte and lymphocyte traffic to the exudates. Alternatively, these potencies in vivo vs. isolated human cells might also reflect species differences. As an inducer of peritonitis, zymosan stimulates the initial formation of many endogenous chemoattractants for PMN, i.e., LTB$_4$, the complement component C5a, chemokines and cytokines (37). Since PD1 stops PMN recruitment in vivo, it counteracts these several different sets of PMN chemoattractants that regulate trafficking of these cells in vivo (FIG. 9 and see ref. 37). Given the inherent chemical liabilities of PD1, a more chemically stable form denoted 15,16-dehydro-PD1 (FIG. 9) was prepared and tested. Although less potent, chemical stabilization of the conjugated double bonds with an acetylenic form proved useful as the molecule retained activity in vivo (FIG. 9). These results are consistent with the ~40% inhibition obtained with a 4,5-acetylenic analog of PD1 (37).

In addition to this lipoxygenase-initiated route of biosynthesis for PD1, an aspirin-triggered route with a 17R epimer of PD1 (17R series) is generated via acetylated COX-2 and subsequent reactions (3, 32); the complete stereochemistry of this bioactive epimer is in progress. It is of interest to note that compound V, 10S,17R-dihydroxy-docosa-4Z,7Z,11E,13E, 15Z,19Z-hexaenoic acid (FIG. 2) was essentially inactive in vivo (FIG. 6A). Whether the many beneficial actions reported for DHA in vitro and with DHA dietary supplementation in humans (21, 24-26) are linked to the formation and actions of these new families of DHA-derived mediators, protectin and D-series resolvins, is of interest and a timely proposal in view of the importance of uncontrolled inflammation in many widely occurring human diseases. These findings also underscore yet another similarity between the immune and neural systems. Hence, results of the present experiments establish the stereochemistry of PD1 (Compound II) and its natural isomers generated by human leukocytes and murine tissues during inflammation. Moreover, they confirm the potent stereoselective anti-inflammatory actions of PD1 and provide new avenues to mark the impact of DHA utilization/supplementation and its endogenous anti-inflammatory/proresolving actions by monitoring PD1, given its unique physical and biological properties documented in the present report.

Evidence is provided herein for protectin D1 (PD1,10R, 17S-dihydroxy-docosa-4Z,7Z,11E,13E,15Z,19Z-hexaenoic acid) formation from docosahexaenoic acid in human asthma in vivo and PD1 counter-regulatory actions in allergic airway inflammation. PD1 and 17S-hydroxy-docosahexaenoic acid were present in exhaled breath condensates from healthy subjects. Of interest, levels of PD1 were significantly lower in exhaled breath condensates from subjects with asthma exacerbations. PD1 was also present in extracts of murine lungs from both control animals and those sensitized and aerosol challenged with allergen. When PD1 was administered prior to aeroallergen challenge, airway eosinophil and T-lymphocyte recruitment were decreased, as were airway mucus, levels of specific pro-inflammatory mediators, including interleukin-13, cysteinyl leukotrienes and prostaglandin $D_2$, and airway hyper-responsiveness to inhaled methacholine. PD1 treatment after aeroallergen challenge markedly accelerated the resolution of airway inflammation. Together, these findings provide evidence for endogenous PD1 as a pivotal counter-regulatory signal in allergic airway inflammation and point to new therapeutic strategies for modulating inflammation in asthmatic lung.

Chronic airway inflammation with large numbers of eosinophils (EOS) and T lymphocytes (Lymphs) infiltrating respiratory tissues is mechanistically linked to asthma pathogenesis (50). In addition to their direct actions, these leukocytes amplify airway inflammation by trafficking into the lung an increased capacity to generate both pro-inflammatory peptides and lipid mediators, such as $T_H2$ cytokines and cysteinyl leukotrienes (CysLTs) (50). In addition, $T_H2$ cytokines up-regulate the expression of biosynthetic enzymes for eicosanoids—including prostaglandins (PGs), LTs and lipoxins (LXs) with potent immunomodulatory properties (51).

DHA levels in the respiratory tract are decreased in asthma and other diseases of excess airway inflammation, such as cystic fibrosis (55). Epidemiologically, a diet high in marine fatty acids (fish oil) may have beneficial effects on inflammatory conditions, including asthma (56, 57) and dietary supplementation with omega-3 fatty acids in children prevents the development of atopic cough, a symptom of allergic airway inflammation (58). The underlying mechanisms for beneficial properties of omega-3 fatty acids in asthma remain to be established.

Natural resolution of acute inflammation (or asthma exacerbation) is driven, in part, by decrements in pro-inflammatory mediators and removal of inflammatory cells (50, 59). Promotion of resolution is now recognized as an active process with early signaling pathways, for example cyclooxygenase-2 derived $PGE_2$ and $PGD_2$, engaging biosynthetic circuits for the later formation of counter-regulatory mediators, such as LXs and the newly identified families of lipid mediators generated from omega-3 fatty acids named resolvins and protectins that can dominate the resolution phase (60). DHA is incorporated into membranes and rapidly released upon neuronal cell activation (61) for conversion to 17S-hydroxy containing resolvins of the D series (because they are from DHA) and protectin D1 (PD1) (62). The complete stereochemistry for PD1 is established as 10R,17S-dihydroxy-docosa-4Z,7Z,11E,13E,15Z,19Z-hexaenoic acid. Throughout the specification, it is shown that PD1 is generated from endogenous sources in human asthma and reduces both allergic airway inflammation and hyper-responsiveness.

In one embodiment, the invention provides PD1 and analogs thereof having the formula:

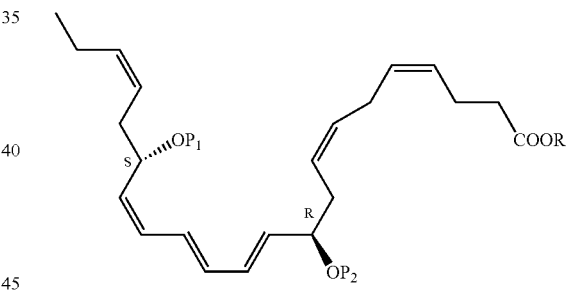

(II)

wherein R is a hydrogen atom, an alkyl group, or is a pharmaceutically acceptable salt and each of $P_1$ and $P_2$, individually, is a hydrogen atom or a protecting group. In one particular aspect, when $P_1$ and $P_2$ are both hydrogen atoms, then R is a pharmaceutically acceptable salt or an alkyl group, such as a methyl or ethyl group. In another aspect, when $P_1$ and $P_2$ are both hydrogen atoms, then R can also be a hydrogen atom provided that the compound is isolated or substantially purified.

In other aspects, the invention provides 10,17-dihydroxy-docasa-hexaenoic acid derivatives having the general formula (VII):

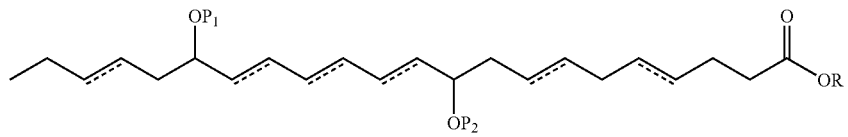

(VII)

wherein R is a hydrogen atom, an alkyl group, or is a pharmaceutically acceptable salt and each of $P_1$ and $P_2$, individually, is a hydrogen atom or a protecting group. The dashed line represents that the double bond can be "cis" or "trans" in configuration. In certain aspects, compounds I, II, IV, V and VI are excluded from the invention.

In still another aspect, the invention provides 10,17-dihydroxy-15,16-dehydrodocasahexaenoic acid derivatives having the general formula (VIII):

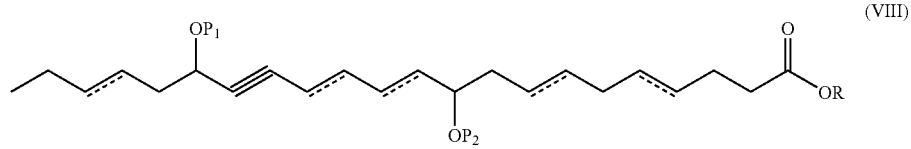

wherein R, $P_1$ and $P_2$, and the dashed lines are as described above. The chiral centers at 10 and 17 can be R/S, S/R or mixtures thereof. In certain embodiments, the 4,5 bond is cis, the 7,8 bond is cis, the 11,12 bond is trans, the 13,14 bond is trans, the 15,16 bond is acetylenic and the 19,20 bond is cis.

In still yet another aspect, the invention provides a 10,17-dihydroxy-15,16-dehydrodocasahexaenoic acid derivative having the general formula (IX):

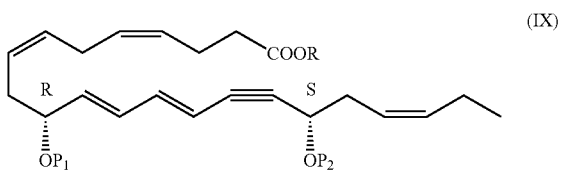

wherein R, $P_1$ and $P_2$ are as described above.

In one aspect of the invention, the compound(s) of the invention are substantially purified and isolated by techniques known in the art. The purity of the purified compounds is generally at least about 90%, preferably at least about 95%, and most preferably at least about 99% by weight (100% by weight).

In certain embodiments, the subject compounds are purified, e.g., substantially separated from other compounds or isomers that are present in a cellular environment where resolvins are produced or that are present in crude products of synthetic chemical manufacturing processes. In certain embodiments, a purified compound is contaminated with less than 25%, less than 15%, less than 10%, less than 5%, less than 2%, or even less than 1% of cellular components (proteins, nucleic acids, carbohydrates, etc.), chemical byproducts, reagents, and starting materials, and the like. In certain embodiments, a purified compound is contaminated with less than 25%, less than 15%, less than 10%, less than 5%, less than 2%, or even less than 1% of other resolvins and/or other isomers of the compound. The addition of pharmaceutical excipients, other active agents, or other pharmaceutically acceptable additives is not understood to decrease the purity of a compound as this term is used herein.

The compounds described throughout the specification can be administered alone or in combination with a pharmaceutically acceptable carrier.

The compounds described throughout the specification can be used to treat inflammation, and in particular airway inflammatory conditions such as asthma.

The compounds described throughout the specification can be administered alone or in combination with one another.

"Alkyl" by itself or as part of another substituent refers to a saturated or unsaturated branched, straight-chain or cyclic monovalent hydrocarbon radical having the stated number of carbon atoms (i.e., C1-C6 means one to six carbon atoms) that is derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl, cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl; cyclobuta-1,3-dien-1-yl, but-1-yn-1-yl, but-1-yn-3-yl, but-3-yn-1-yl, etc.; and the like. Where specific levels of saturation are intended, the nomenclature "alkanyl," "alkenyl" and/or "alkynyl" is used, as defined below. In preferred embodiments, the allyl groups are (C1-C6) alkyl.

"Alkanyl" by itself or as part of another substituent refers to a saturated branched, straight-chain or cyclic alkyl derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like. In preferred embodiments, the alkanyl groups are (C1-C6) alkanyl.

"Alkenyl" by itself or as part of another substituent refers to an unsaturated branched, straight-chain or cyclic allyl having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like. In preferred embodiments, the alkenyl group is (C2-C6) alkenyl.

"Alkynyl" by itself or as part of another substituent refers to an unsaturated branched, straight-chain or cyclic alkyl having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like. In preferred embodiments, the alkynyl group is (C2-C6) alkynyl.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3$^{rd}$ Ed., 1999, John Wiley & Sons, NY and Harrison et al., *Compendium of Synthetic Organic Methods*, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPPS groups), glycol ethers, such as ethylene glycol and propylene glycol derivatives and allyl ethers.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting a compound(s) of the present invention within or to the subject such that it can perform its intended function. Typically, such compounds are carried or transported from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

In certain embodiments, the compounds of the present invention may contain one or more acidic functional groups and, thus, are capable of forming pharmaceutically acceptable salts with pharmaceutically acceptable bases. The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. These may include cations based on the alkali and alkaline earth metals, such as sodium, lithium, potassium, calcium, magnesium and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See, for example, Berge S. M., et al., "Pharmaceutical Salts," J. Pharm. Sci., 1977; 66:1-19 which is incorporated herein by reference).

The term "pharmaceutically acceptable esters" refers to the relatively non-toxic, esterified products of the compounds of the present invention. These esters can be prepared in situ during the final isolation and purification of the compounds, or by separately reacting the purified compound in its free acid form or hydroxyl with a suitable esterifying agent. Carboxylic acids can be converted into esters via treatment with an alcohol in the presence of a catalyst. The term is further intended to include lower hydrocarbon groups capable of being solvated under physiological conditions, e.g., alkyl esters, methyl, ethyl and propyl esters.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations of the present invention include those suitable for intravenous, oral, nasal, topical, transdermal, buccal, sublingual, rectal, vaginal and/or parenteral administration. The formulations may conveniently be presented in unit dosage form and may be prepared by any methods well known in the art of pharmacy. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention. Such solutions are useful for the treatment of conjunctivitis.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

The preparations of the present invention may be given orally, parenterally, topically, or rectally. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Intravenous injection administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systematically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of ordinary skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous and subcutaneous doses of the compounds of this invention for a patient, when used for the indicated analgesic effects, will range from about 0.0001 to about 100 mg per kilogram of body weight per day, more preferably from about 0.01 to about 50 mg per kg per day, and still more preferably from about 0.1 to about 40 mg per kg per day. For example, between about 0.01 microgram and 20 micrograms, between about 20 micrograms and 100 micrograms and between about 10 micrograms and 200 micrograms of the compounds of the invention are administered per 20 grams of subject weight.

If desired, the effective daily dose of the active compound may be administered as two, three, four, five, six or more sub-doses administered separately at appropriate intervals throughout the day, optionally, in unit dosage forms.

The pharmaceutical compositions of the invention include a "therapeutically effective amount" or a "prophylactically effective amount" of one or more of the compounds of the invention. A "therapeutically effective amount" refers to an amount effective, at dosages and for periods of time necessary, to achieve the desired therapeutic result, e.g., a diminishment or prevention of effects associated with various disease states or conditions. A therapeutically effective amount of the compound may vary according to factors such as the disease state, age, sex, and weight of the individual, and the ability of the therapeutic compound to elicit a desired response in the individual. A therapeutically effective amount is also one in which any toxic or detrimental effects of the therapeutic agent are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of a compound of the invention is 0.1-20 mg/kg, more preferably 1-10 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

Delivery of the compound of the present invention to the lung by way of inhalation is an important method of treating a variety of respiratory conditions (airway inflammation) noted throughout the specification, including such common local conditions as bronchial asthma and chronic obstructive pulmonary disease. The compound can be administered to the lung in the form of an aerosol of particles of respirable size (less than about 10 µm in diameter). The aerosol formulation can be presented as a liquid or a dry powder. In order to assure proper particle size in a liquid aerosol, as a suspension, particles can be prepared in respirable size and then incorporated into the suspension formulation containing a propellant. Alternatively, formulations can be prepared in solution form in order to avoid the concern for proper particle size in the formulation. Solution formulations should be dispensed in a manner that produces particles or droplets of respirable size.

Once prepared an aerosol formulation is filled into an aerosol canister equipped with a metered dose valve. The formulation is dispensed via an actuator adapted to direct the dose from the valve to the subject.

Formulations of the invention can be prepared by combining (i) at least one compound of the invention in an amount sufficient to provide a plurality of therapeutically effective doses; (ii) the water addition in an amount effective to stabilize each of the formulations; (iii) the propellant in an amount sufficient to propel a plurality of doses from an aerosol canister; and (iv) any further optional components e.g. ethanol as a cosolvent; and dispersing the components. The components can be dispersed using a conventional mixer or homogenizer, by shaking, or by ultrasonic energy. Bulk formulation can be transferred to smaller individual aerosol vials by using valve to valve transfer methods, pressure filling or by using conventional cold-fill methods. It is not required that a stabilizer used in a suspension aerosol formulation be soluble in the propellant. Those that are not sufficiently soluble can be coated onto the drug particles in an appropriate amount and the coated particles can then be incorporated in a formulation as described above.

Aerosol canisters equipped with conventional valves, preferably metered dose valves, can be used to deliver the formulations of the invention. Conventional neoprene and buna valve rubbers used in metered dose valves for delivering conventional CFC formulations can be used with formulations containing HFC-134a or HFC-227. Other suitable materials include nitrile rubber such as DB-218 (American Gasket and Rubber, Schiller Park, Ill.) or an EPDM rubber such as Vistalon™ (Exxon), Royalene™ (UniRoyal), bunaEP (Bayer). Also suitable are diaphragms fashioned by extrusion, injection molding or compression molding from a thermoplastic elastomeric material such as FLEXOMER™ GERS1085 NT polyolefin (Union Carbide).

Formulations of the invention can be contained in conventional aerosol canisters, coated or uncoated, anodized or unanodized, e.g., those of aluminum, glass, stainless steel, polyethylene terephthalate.

The formulation(s) of the invention can be delivered to the respiratory tract and/or lung by oral inhalation in order to effect bronchodilation or in order to treat a condition susceptible of treatment by inhalation, e.g., asthma, chronic obstructive pulmonary disease, etc. as described throughout the specification.

The formulations of the invention can also be delivered by nasal inhalation as known in the art in order to treat or prevent the respiratory conditions mentioned throughout the specification.

While it is possible for a compound of the present invention to be administered alone, it is preferable to administer the compound as a pharmaceutical composition.

The invention features an article of manufacture that contains packaging material and a compound of the invention contained within the packaging material. This formulation contains an at least one compound of the invention and the packaging material contains a label or package insert indicating that the formulation can be administered to the subject to treat one or more conditions as described herein, in an amount, at a frequency, and for a duration effective to treat or prevent such condition(s). Such conditions are mentioned throughout the specification and are incorporated herein by reference. Suitable EPA analogs and DHA analogs are described herein.

More specifically, the invention features an article of manufacture that contains packaging material and at least one compound of the invention contained within the packaging material. The packaging material contains a label or package insert indicating that the formulation can be administered to the subject to asthma in an amount, at a frequency, and for a duration effective treat or prevent symptoms associated with such disease states or conditions discussed throughout this specification.

Materials and Methods

Materials—Zymosan A, soybean lipoxygenase (fraction V), and calcium ionophore, A-23187, were purchased from Sigma Co. (St. Louis, Mo.). Docosahexaenoic acid (C22:6, DHA) and 5-LO from potato (pt5LO) were from Cayman Chemical Co. (Ann Arbor, Mich.). Additional materials used in LC-UV-MS-MS analyses were from vendors reported in (1, 3). $^{18}O_2$ isotope was purchased from Cambridge Isotopes (Andover, Mass.).

Isolation, LC-MS-MS and GC-MS Analyses—Incubations were extracted with deuterium-labeled internal standard ($PGE_2$) (Cayman Chemicals) for LC-MS-MS analysis using a Finnigan LCQ liquid chromatography ion trap tandem mass spectrometer equipped with a LUNA C18-2 (150×2 mm 5 μm) column and a rapid spectra scanning UV diode array detector using mobile phase (methanol:water:acetate at 65:35:0.01) with a 0.2 ml/min flow rate that monitored UV absorbance ~0.1 min before samples entered the MS-MS. The scan acquisition rates were 11/min for MS-MS and 60/min for UV, which give rise to a lag interval in retention times that was corrected in the results presented for each molecule. All intact cell incubations and in vivo exudates were stopped with 2 vol cold methanol and kept at 20° C. for >30 min. Samples were extracted using C18 solid phase extraction and further analyzed using gas chromatography-mass spectrometry (GC-MS) using a Hewlett-Packard 6890 with a HP 5973 mass detector (see FIG. 8), and tandem liquid chromatography-mass spectrometry (LC-MS-MS). Detailed procedures for isolation, quantitation, and structural determination of these DHA and related lipid-derived mediators were reported recently (1, 36) and used here essentially as reported for elucidation of new products. Biogenic synthesis of some of the DHA-derived products were performed using isolated enzymes, i.e., 5-LOX from potato and 15-LO were each incubated in tandem sequential reactions (see refs. 1, 3, 37, 38) with either DHA, 17S-hydroxy-DHA, or 17S-hydroperoxy-DHA to produce the compounds in quantities suitable for isolation and incubation with cells and tissues as well as confirmation of physical properties and assigning biological actions. Incubations in an $^{18}O_2$-enriched atmosphere were performed and analyzed as in ref. (39).

NMR for Protectin D1—$^1$H NMR (400 MHz, MeOH-d4): δ 6.52 (dd, J=14.1 Hz and 11.8 Hz, 1H), 6.26 (m, 2H), 6.07 (dd, J=11.1 Hz and 11.1 Hz, 1H), 5.50-5.28 (m, 7H), 4.90 (s, 2H), 5.50-5.60 (m, 2H), 4.55 (m, 1H), 4.14 (m, 1H), 3.65 (s, 3H), 2.82 (m, 2H), 2.40-2.13 (m, 8H), 2.06 (m, 2H), 2.07 (m, 2H), 0.96 (t, J=7.5 Hz, 3H).

$^{13}$C NMR (125 Hz, MeOH-d4): δ 174.93, 137.59, 134.56, 134.47, 134.35, 131.01, 130.52, 130.17, 129.92, 128.57, 128.52, 126.14, 124.89, 72.60, 68.18, 36.00, 35.97, 34.45, 26.30, 23.43, 21.312, 14.20.

Incubations with Human PMN and Whole Murine Brain—Human venous whole blood (~10 ml) was collected into heparin (0.01 units/ml) via venipuncture from healthy volunteers (who declined taking medication for ~2 weeks before donation; Brigham and Women's Hospital protocol 88-02642). Human PMN were freshly isolated from whole blood using Ficoll gradient and enumerated as in (40). PMN (30×10$^6$ cells/ml) were exposed to ionophore A23187 (5 μM) with either DHA or 17S-hydro(peroxy)-DHA (15 μg/ml). Cell suspensions were incubated for 30 min at 37° C. in a covered water bath. Lipidomics and lipid mediator profile analyses were carried out for DHA-derived products, resolving, and docosatrienes as in (1, 3, 18, 36). Whole murine brains (Charles River Laboratories, Wilmington, Mass.) were excised, and then homogenized in PBS (minus $Mg^{2+}$ and $Ca^{2+}$) (Cambrex Bioscience, Walkersville, Md.). Brain homogenates were washed one time (800 rpm, 4° C., 5 min) in PBS, and then suspended in 1 ml of PBS minus divalent cations. Homogenates were placed in the incubator (5 min) with an atmosphere of 5% $CO_2$, 37° C., and calcium ionophore A23187 (5 μM) or DHA (30 μM) was added. Brain homogenates were then placed in the incubator for 30 min with an atmosphere of 5% $CO_2$ (37° C.). Incubations were stopped with 2 volumes of ice-cold MeOH, and, after 30 min at 4° C., the suspensions were pelleted and the supernatants were extracted using solid phase C18 cartridges (Alltech Associates, Deerfield, Ill.). Material eluted with methyl formate was taken to dryness using a stream of nitrogen gas and taken for further analyses.

Human Neutrophil Transmigration—PMN were freshly isolated from whole blood obtained by venipuncture from healthy human donors (who denied taking medication for 2 weeks prior to donation; BWH protocol no. 88-02642) and anti-coagulated with acid citrate dextrose as in (40, 41). Briefly, plasma and mononuclear cells were removed by aspiration from the buffy coat after centrifugation (400 g; 20 min) at room temperature. Histopaque (density 1.077) was from Sigma-Aldrich (St. Louis, Mo.). RBCs were sedimented using 2% gelatin, and residual RBCs were removed by lysis in ice-cold $NH_4Cl$ buffer. The cell suspensions were >90% PMN as determined by light microscopic evaluation. PMN were suspended at 5×10$^7$ cells/ml in HBSS with 10 mM Hepes, pH 7.4, and without $Ca^{2+}$ or $Mg^{2+}$ (Sigma-Aldrich, St. Louis, Mo.). PMN were used within 2 hours of their isolation.

Human Microvascular Endothelial Cells (HMEC; a gift from Francisco Candal of the Centers for Disease Control, Atlanta, Ga.) were obtained as primary cultures. For preparation of experimental HMEC monolayers, confluent endothelial cells were grown on 0.33 cm$^2$ ring-supported polycarbonate filters (5 μm pore size; Costar Corp., Cambridge, Mass.) in the apical-to-basolateral direction. Cells were grown for ~1 week prior to transmigration experiments.

Transmigration was conducted essentially as in ref. (41). PMN were incubated with either vehicle-containing buffer or compound for 15 minutes at 37° C. A chemotactic gradient was established by placing HMEC inserts that had been washed in HBSS with $Ca^{2+}$ and $Mg^{2+}$ (denoted +/+) in 10$^{-8}$M $LTB_4$ in the lower chambers. Neutrophils (10$^6$ cells) were added to 50 μl HBSS+/+ in the upper chambers and cells were incubated at 37° C. for 90 min. Transmigrated PMN were quantified by assessing the PMN azurophilic marker myeloperoxidase and a calibration curve. PMN were lysed by the addition of Triton X-100 to a final concentration of 0.5%. The samples were acidified with citrate buffer (final concentration 100 mM, pH 4.2). An aliquot of each sample was added to an equal volume of ABTS solution (1 mM ABTS [2'-azino-bis (3-ethylbenzo-thiazoline-6-sulfonic acid)], 0.03% $H_2O_2$, 100 mM sodium citrate buffer, pH 4.2) in a 96-well plate. The resulting color was monitored using a plate reader at 405 nm and a calibration curve for cell number.

Acute Inflamatory Exudates: Murine Peritonitis—Peritonitis was carried out using 6-8 week-old FVB male mice (Charles River Laboratories) fed laboratory Rodent Diet 5001 (Purina Mills) that were anesthetized with isoflurane, and compounds to be tested were administered intraperitoneally. Zymosan A in 1 ml saline (1 mg/ml) was injected ~1-1.5 min later in the peritoneum. Each compound tested or vehicle alone was suspended in 1 μl ethanol and mixed in sterile saline (120 μl). After intraperitoneal injections (either 2 or 4 hours of acute inflammation), the mice were sacrificed in accordance with the Harvard Medical Area Standing Committee on Animals protocol no. 02570, and peritoneal lavages were collected rapidly and placed in an ice bath (4° C.) for enumeration, differential counts, and further analysis.

Sensitization and challenge protocols—Five to seven week old male FvB mice (Charles River Laboratories) were housed in isolation cages under viral antibody-free conditions. Mice were fed a standard diet (Laboratory Rodent Diet 5001, PMI Nutrition International) that contained no less than 4.5% total fat with 0.26% omega-3 fatty acids and <0.01% C20:4. After Harvard Medical Area IRB approval (Protocol #02570), mice were sensitized with intraperitoneal injections of ovalbumin (OVA) (Grade III; Sigma Chemical Co.) (10 μg) plus 1 mg aluminum hydroxide (ALUM) (J.T. Baker Chemical Co.) as adjuvant in 0.2 ml PBS on days 0 and 7. On days 14, 15, 16 and 17, the mice received PD1 (2, 20 or 200 ng) (a product of biogenic synthesis (52)) or PBS with 1.6 mM $CaCl_2$ and 1.6 mM $MgCl_2$ (0.1 ml) by intravenous injection 30 min prior to an aerosol challenge containing either PBS or 6% OVA for 25 min/day. Matching experiments were performed with 20 ng PD1 prepared by total organic synthesis (62).

On day 18, 24 h after the last aerosol challenge, either airway responsiveness to aerosolized methacholine (0, 20, 50 and 75 mg, 10 sec) was measured, bilateral bronchoalveolar lavage (BAL) (2 aliquots of 1 ml PBS plus 0.6 mM EDTA) was performed or tissues were harvested for histological analysis. Lung resistance was measured using a Flexivent ventilator (SciReq). Resistance was measured as a function of time for each animal, and peak and average values for each dose of methacholine were recorded. No BAL or histological analysis was performed on those animals undergoing airway hyper-responsiveness or lipid extraction studies.

In select experiments, animals were sensitized and aeroallergen challenged for four days prior to receiving PD1 (20 ng) or PBS by intravenous injection (0.1 ml) on days 18, 19 and 20. On day 21, bilateral BAL was performed.

Allergen-initiated respiratory inflammation—Murine lungs were fixed in 10% buffered formalin and paraffin embedded for hematoxylin and eosin and periodic acid Schiff staining (Sigma Chemical Co.). Tissue morphometry was performed by a member (K. Haley) of the Lung Histopathology Core Laboratory at Brigham and Women's Hospital who was blinded to the experimental conditions prior to histological analyses. Three fields per slide were examined at 200× magnification for vessels, large airways and alveoli with EOS counted at 400× magnification in randomly assigned fields. Vessels were identified by perivascular smooth muscle, and large airways were identified by at least ½ their diameter either cuboidal or columnar epithelia. Measurement of inflammatory mediators was determined in cell-free BAL fluid (BALF) (2000 g, 10 min) by sensitive and specific ELISAs, in tandem, for interleukin-5 (IL-5), IL-12, IL-13, $PGD_2$ (R&D Systems), cysteinyl LTs, (Cayman Chemical Co.), and $LXA_4$ (Neogen). Cells in BALF were resuspended in PBS, enumerated by hemocytometer, and concentrated onto microscope slides by cytocentrifuge (STATspin) (265 g). Cells were stained with a Wright-Giemsa stain (Sigma Chemical Co.) to determine leukocyte differentials (after counting ≧200 cells).

PD1 Extraction and Identification by LC-MS-MS—Exhaled breath condensates were collected by R-tube (Respiratory Research, Inc.) from volunteer subjects who had given written informed consent to a protocol approved by the Brigham and Women's Hospital Committee for the Protection of Human Subjects in Research. Samples were collected during 10 minutes of tidal breathing. Characteristics of the subjects are provided in FIG. 10. For samples of murine lung, blood was flushed from the pulmonary circulation with 2 ml PBS, and whole murine lungs were removed from OVA-sensitized/OVA-challenged and control mice on Day 18. Using a manual dounce, lungs were gently homogenized for direct lipid extraction in MeOH or in some cases were warmed (5 min, 37° C.) in PBS, and incubated (40 min, 37° C.) in the absence or presence of DHA (100 μg). Reactions were stopped with 10 volumes of iced MeOH and stored at −20° C. overnight.

Figure 11:
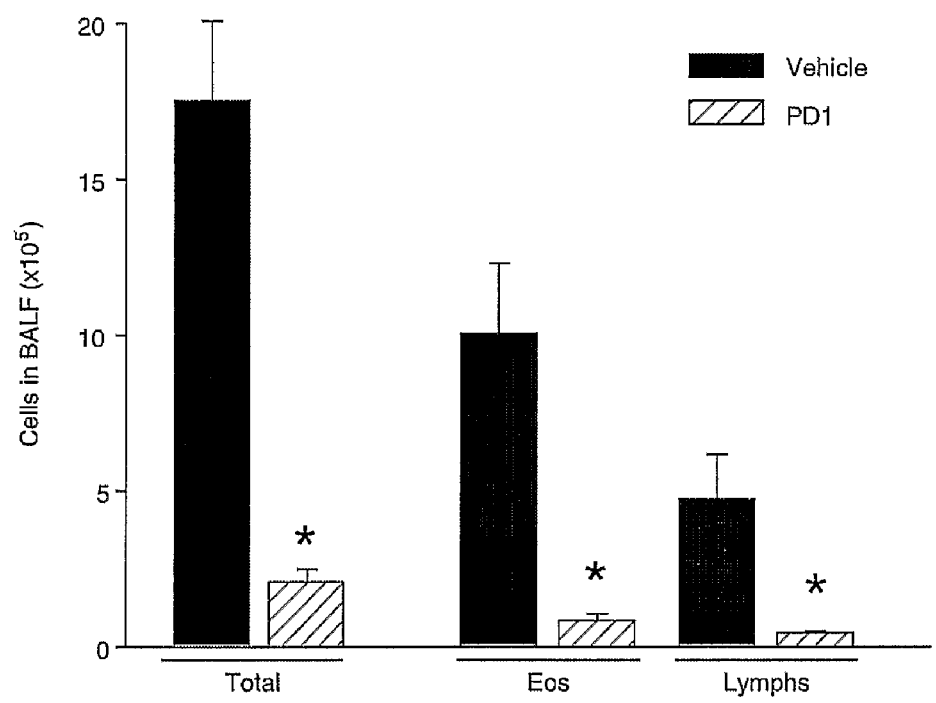
FIG. 11: Generation of Protectin D1 in asthma. Exhaled breath condensates were obtained from volunteer subjects in the emergency department during a clinical exacerbation of asthma. Lipids were extracted and subjected to analysis by LC-PDA-MS-MS. (a) LC chromatogram plotted for ms/ms at m/z 343 and (b) corresponding MS profile were diagnostic for 17(S)-hydroxy-DHA (i.e., 17S-hydroxy-docosa-4Z,7Z,11E, 13E,15Z,19Z-hexaenoic acid). Material was also present in the lipid extracts with (c) LC chromatogram for m/z 217 of ms/ms at m/z 359, (d) UV absorbance spectrum (inset, left) and mass spectrum diagnostic for authentic Protectin D1 (i.e., 10R,17S-dihydroxy-docosa-4Z,7Z,11E,13E,15Z,19Z-hexaenoic acid). Insets, the fragmentation ions are denoted for (b) 17(S)-hydroxy-DHA and (d) Protectin D1. Results are representative of n=3.

Lipids in EBC or murine lung were extracted using C18 cartridges (Alltech) and deuterium-labeled $d_4$-$PGE_2$ as an internal standard to correct for losses during extraction (52). Materials eluting in the methyl formate fraction were taken to HPLC coupled to a photo-diode-array detector and tandem mass spectrometry (LC-PDA-MS-MS, ThermoFinnigan) for lipidomic analyses. PD1 was identified using criteria that include retention time, coelution with authentic 10R,17S-dihydroxy-docosa-4Z,7Z,11E,13E,15Z,19Z-hexaenoic acid, UV absorbance in methanol (λmax 270 nm with shoulders at 261 and 281 nm, a triple band of absorption consistent with a conjugated triene structure) and at least 5 diagnostic MS-MS ions (m/z 359 [M-H], 341 ([M-H]-$H_2O$; base peak), 323 ([M-H]-$2H_2O$), 315 ([M-H]-$CO_2$), 297 ([M-H]-$H_2O$, —$CO_2$), and 277 ([M-H]-$H_2$-$2H_2O$—$CO_2$) plus additional ions defining the presence of the C10 and C17 hydroxyl (i.e., m/z 289, 261, 243 (261-$H_2O$), 217 (261-$CO_2$), 205, 181, 163 (181-$H_2O$) and 153) (FIG. 11). The quantitation of PD1 was determined following LC-MS-MS analyses using a calibration curve ($r^2$=0.991) and the chromatographic peak areas obtained via selective ion monitoring.

Statistical analysis—Results are expressed as the mean±SEM. Statistical significance of differences was assessed by Student's t-test and Kruskal-Wallis nonparametric one-way ANOVA. $P<0.05$ was set as the level of significance.

Results

Complete Stereochemistry of PD1—The DHA-derived 10,17-dihydroxy conjugated triene-containing product PD1 is generated by several human cell types, murine exudates, skin, and brain tissues (1-3, 32), as well as isolated fish tissues, indicating that it is a conserved structure in evolution (35). PD1 displays potent protective and anti-inflammatory actions (1, 2, 18, 32). To determine the complete stereochemical assignment of PD1, i.e., the chirality at C10 and the geometry of the triene, the physical and biologic properties of DHA-derived PD1 and related 10,17 dihydroxy-docosatriene stereoisomers were directly compared to those prepared by total organic and biogenic synthesis. These included: I 10S,17S-dihydroxy-docosa-4Z,7Z,11E,13E,15E,19Z-hexaenoic acid; II 10R,17S-dihydroxy-docosa-4Z,7Z,11E,13E,15Z,19Z-hexaenoic-acid and V 10S,17R,-dihydroxy-docosa-4Z,7Z,11E,13E,15Z,19Z-hexaenoic-acid coelute in this HPLC system; III 10R,17S-dihydroxy-docosa-4Z,7Z,11E,13E,15E,19Z-hexaenoic-acid; IV 10R,17S-dihydroxy-docosa-4Z,7Z,11E,13Z,15E,19Z-hexaenoic-acid; and VI 10S,17S-dihydroxy-docosa-4Z,7Z,11E,13E,15Z,19Z-hexaenoic-acid. The total synthesis of these will be reported elsewhere.[3] Of interest, I and VI coeluted in this system, as did both II and V (FIGS. 1 and 2). Bioactive PD1 was generated by isolated human cells, murine brain tissue, and during inflammation in vivo. FIG. 1 reports representative chromatographic profiles for PD1 generated by isolated human neutrophils incubated with DHA that was separated into several positional and geometric isomers (FIG. 1A, top panel). The main positional isomer of 10,17S-docosatriene was 7,17-diHDHA (denoted resolvin D5), as documented earlier (1, 3), and a double dioxygenation product (see Ref. 37). Also, a representative profile of products is given for those obtained from murine inflammatory exudates (FIG. 1A, middle panel) and neural tissues (not shown). A direct comparison of these materials is reported in Panel A, FIG. 1 along with the profile obtained for synthetic materials (FIG. 1A, lower panel) and chromatograms recorded by MS-MS (right) and UV at 270 nm (FIG. 1A, left side).

The complete stereochemistry of bioactive 10,17-docosatriene, PD1, namely the double bond geometry of the conjugated triene unit and chirality of its carbon 10-position remained to be established (see FIG. 2, top, middle). In order to assign the complete stereochemistry of bioactive PD1 and its related natural geometric isomers, it was necessary to carry out total organic synthesis and side-by-side matching experiments with murine and human systems because PD1 is generated in only nanogram quantities commensurate with its potent actions in vivo and in vitro, but preclude direct NMR analysis. The mixture of synthetic isomers used is shown in the lower insert of Panel A, FIG. 1. The human and murine generated bioactive PD1 matched the physical and biologic properties of synthetic 10R,17S-dihydroxy-docosa-4Z,7Z, 11E,13E,15Z,19Z-hexaenoic acid (Compound II). In addition to both LC-MS-MS and GC-MS analyses with these materials (FIG. 8), experiments were carried out with both biologic and synthetic isomers prepared with the same overall backbone structure, namely 10,17-dihydroxydocosatriene. A 17R-containing isomer was prepared and included in these experiments (isomer V; see FIG. 2), but could be eliminated in these assignments, since 17R-containing products are the major series produced from DHA when aspirin is used (3, 18). Thus, although II and V coelute in this system, V could be eliminated as a major DHA-derived product in these incubations (FIGS. 1 and 2).

The chirality of the alcohols and double bond geometry of the triene were systematically addressed. FIG. 1B shows the MS-MS spectrum of PD1 obtained from murine peritonitis (4 h) generated in vivo upon challenge with zymosan A. FIG. 1, Panel C reports the mass spectrum recorded using the same instrument settings and conditions with synthetic 10R,17S-dihydroxy-docosa-4Z,7Z,11E,13E,15Z,19Z-hexaenoic acid (Compound II, FIGS. 1 and 2). To obtain additional evidence for matching, GC-MS analyses were performed. FIG. 1, Panel D reports a representative mass spectrum and prominent ions obtained with GC-MS for PD1 treated with diazomethane and subsequently converted to its corresponding trimethylsilyl derivative. Hence, chromatographic behavior and prominent ions in two mass spectrometry systems (LC-MS-MS and GC-MS), together with biological activity (see FIGS. 5 and 6), permitted criteria for assignment of the physical properties of PD1 and related isomers. Since the parent and daughter ions were the same for each isomer, retention time in two chromatographic systems and bioactivity were needed for assigning the stereochemistry of the endogenous PD1 (vide infra).

Figure 3:
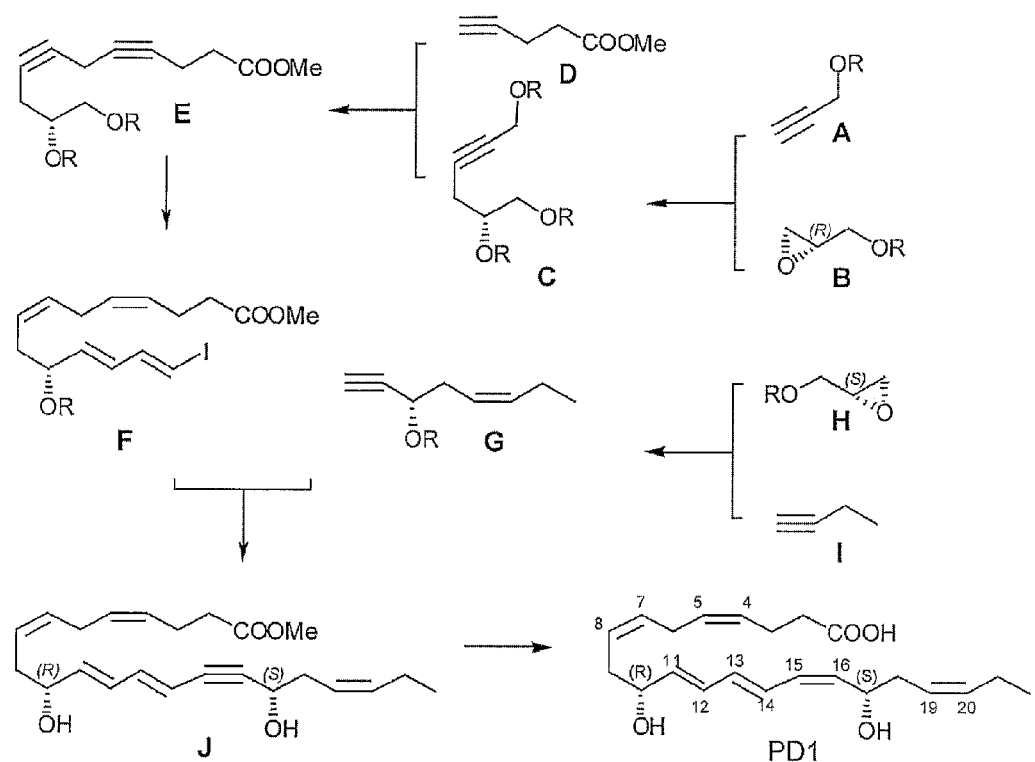
FIG. 3: Strategy for total synthesis of PD1 and related isomers. The $C_{10}$ and $C_{17}$ stereochemistry of 1 was derived from enantiomerically pure glycidol derivatives B and H which were reacted with alkynyl nucleophiles derived from A and I, respectively. The (Z) alkene geometry at positions 4-5, 7-8, 15-16 and 19-20 was obtained from selective hydrogenation of acetylenic precursors, which were constructed using coupling procedures. The (E) geometry at positions 11-12 and 13-14 was secured during the synthesis of intermediate F. Other stereoisomers of 1 were synthesized similarly.

Compounds synthesized for these matching experiments are given in FIG. 2. PD1 isolated and identified earlier carries alcohol groups at carbon 10 and 17 positions flanking the conjugated triene portion of this molecule (1, 3). The stereochemistry of the carbon 17-position alcohol was retained from the precursor predominantly in the S configuration when derived from the LOX product 17S—H(p)DHA precursor (1, 3), eliminating isomer V from the matching panel in FIGS. 1 and 2. The double bond geometry and stereochemistry of the alcohol group at position 10 were tentatively assigned based on biogenic evidence, i.e., the formation of alcohol trapping products in murine brain and human leukocytes as well as identification of two vicinal diols 16,17S-diHDHA; hence the complete stereochemical assignment remained as illustrated in FIG. 2, top. To this end, each of the double bond isomers likely to be biosynthesized was prepared in view of potential biosynthetic routes involved in PD1 formation, namely the involvement of epoxide-containing intermediates and/or double dioxygenation intermediates (1-3). The R and S configuration of the alcohol group at the carbon 10-position were each prepared by stereocontrolled total organic synthesis. The strategy for the synthesis of these is outlined in FIG. 3. Each of the stereocontrolled steps from defined precursors enabled preparation of geometric isomers of the conjugated triene region that were confirmed by NMR (see Materials and Methods). Also, for these experiments dihydroxydocosanoids were prepared using isolated plant lipoxygenase(s) to obtain, as in earlier experiments (37), both positional isomers 7,17S-diHDHA and 10,17S-diHDHA (1, 3). The preparation of these using micellar substrate was given in further detail in (37). These reference compounds were useful in analyses of biosynthetic routes (see below).

FIG. 8 reports the prominent ions and chromatographic behaviors for each of the double bond and positional isomers prepared (FIG. 2). As expected, each of these isomers gave characteristic UV $\lambda_{max}^{MeOH}$ for a conjugated triene chromophore with a $\lambda_{max}^{MeOH}$ at ~270 nm with shoulders at 260 nm and 282 nm (±2 nm). Each isomer gave a specific $\lambda_{max}^{MeOH}$, which appeared to reflect the geometry of the double bond system. For example, the Δ15-trans isomer in the conjugated triene portion of 10,17-diHDHA gave a UV $\lambda_{max}^{MeOH}$ of 269 nm (FIG. 8). Only one of these products (Compound II) matched the chromatographic behavior using both LC-MS and GC-MS as well as biological activity. As expected, each of the major prominent ions for these isomers in both LC-MS-MS and GC-MS were essentially identical (i.e., daughter and parent ions were essentially the same for each).

The main materials isolated from human PMN coeluted with compound II and, in some preparations, a trace amount of compound IV. Compound IV differs from II in its triene configuration, which is 11E,13Z,15E. This change in two double bonds was unlikely in view of the earlier identification of alcohol trapping products (1). Also, compound IV was not observed in all PMN incubations, which might reflect some degree of donor variation. A second representative profile from another human donor is reported in FIG. 1A, top right panel, at m/z 260.8 to 261.8 of the MS-MS for M-1 at m/z=359. As noted for this ion plot and donor, compound II is the most abundant and IV is not present. Also, compound I is clearly present along with an unknown material denoted with an asterisk. In this panel, the retention time of isomer III is plotted in gray for direct comparison. Only trace amounts of III, the Δ15-trans isomer of PD1, were routinely identified. The appearance of this Δ15-trans isomer with its triene in the all-trans configuration likely reflects workup-induced isomerization at the Δ15 position, which may account for its varied presence in LC-MS-MS-based analysis. This is in addition to Δ15-trans-PD1 formation via nonenzymatic hydrolysis of the proposed epoxide intermediate (FIG. 4B).

Compound I was consistently identified in profiles obtained from murine peritonitis (FIG. 1A middle). However, it was not the major product of human cells nor did it carry potent actions as compound II did (FIGS. 5, 6), also reported earlier (1, 3, 39). Consistent with its biosynthesis (vide infra), the appearance of this double dioxygenation product was time-dependent in vivo and in vitro (not shown). Although isomer VI coeluted with I in this system, it was excluded on the basis that it was not a major product of human cells and is not likely to be generated from an epoxide intermediate without a specialized enzyme (see FIG. 4 and below). The stereoselective insertion of oxygen from $H_2O$ can be expected to give rise to predominantly a 10R configuration when attaching a carbonium cation intermediate; proposed in ref. (1).

Compound VI differs from PD1 in its C10 position, which is 10S rather than 10R and is not a double dioxygenation product because its double bond geometry in the triene portion of the compound is not consistent with the biosynthesis of the triene in the trans, cis, trans configuration. Since these and other lipid mediators are highly conserved structures found in many species from fish to human (35), a species difference between mouse and human in PD1 structure is not likely. Hence, although compound VI carries bioactivity (FIG. 6), it was excluded on the basis of the above findings and because compound VI was not a major isomer in human profiles, as compound II was. Hence, compound II matched PD1 formation and physical properties as well as potency of action (see below).

The biosynthesis of 7,17-diHDHA in inflammatory exudates (3, 18) and its formation from DHA or 17-hydroxy-DHA with isolated human neutrophils suggested that the biosynthesis of this compound involved formation via double dioxygenation (18). That is, in addition to using molecular oxygen for insertion at the 17-position, lipoxygenation could also insert molecular oxygen at the 7-position in sequential fashion. The identification of this novel compound from DHA and the sequential lipoxygenation events in its formation (1, 3) appeared to be similar to that of 5S,15S-diHETE generated from arachidonic acid (42, 43). Hence, it was of particular interest in earlier studies (37) when sequential actions of potato 5-lipoxygenase and/or 15-lipoxygenase with the substrates in micellar configuration were noted to produce both 7,17-diHDHA and 10,17-diHDHA isomers as major products as well as multiple geometric isomers as minor products following hydrolysis of enzymatically generated epoxides in vitro (cf. 1, cf. 3). The formation of the minor isomers was dependent on substrate, pH, and enzyme concentration.

To test the role of sequential LO actions in the proposed mechanism of PD1 formation (Compound II; see FIG. 2) and its isomer 10S,17S-diHDHA (Compound I), incubations were carried out in an atmosphere enriched in isotope $^{18}O_2$ with 17-hydroperoxy-DHA as substrate and isolated pt 5-lipoxygenase (see Methods). Note that Compounds I and II differ in both chirality at carbon 10 and geometry of their respective triene configurations (FIG. 2). Following extraction and isolation, the product profiles, GC-MS and LC-MS-MS results indicated that $^{18}O$ was incorporated in the carbon 10-position in 10S,17S-diHDHA (FIG. 4). Chromatographic separation of 10S,17S-diHDHA (FIG. 4) gave prominent ions with MS-MS (FIG. 4, Panel A), indicating on average >75% incorporation of $^{18}O$ originating from molecular oxygen in the carbon 10-position with a range of 51.4 to 91.8% increase in diagnostic ions. Since these enzymes use molecular oxygen as a substrate, it is not possible, under these conditions, to completely replace enzyme-associated $^{16}O$ for the $^{18}O$ isotope as calculated earlier for lipoxin $A_4$ in refs. (39, 44). The extent of $^{18}O$ present in diagnostic ions was determined for m/z 181/183, 261/263, 289/291, 297/299, 315/317, 323/325, 341/343, and 359/361, and the ratio of $^{16}O$ to $^{18}O$ calculated from ion intensities and averaged. These results indicate that 10S,17S-diHDHA can be produced via double lipoxygenation.

Results for matching studies indicated that the double bond geometry for the conjugated triene portion of this molecule was in the trans, cis, trans configuration (matching Compound I, FIG. 2). Hence, double dioxygenation to form 10S,17S-diHDHA was also a mechanism to generate this compound in vivo, since it is a prominent product in murine exudates from peritonitis, and to some extent present in suspensions of human leukocytes incubated with DHA, (FIG. 1 and ref. 1) and murine brain (3, 18), as well as trout leukocytes and brain (35). FIG. 4, Panel B outlines the proposed scheme and proposed role for double dioxygenation and its products 10S,17S-diHDHA and 7S,17S-diHDHA. The double bond geometry in the conjugated triene portion of the molecule (trans,cis,trans) is consistent with oxygenation using molecular oxygen with two sequential lipoxygenation steps. Given the biological actions, chromatographic and physical properties of PD1 as well as the results from epoxide trapping experiments with human PMN and the isolation of two vicinal diol 16,17S-dihydroxy-docosatrienes as minor products (1), it is likely that, once a 16,17-epoxide-containing intermediate is generated in situ (as illustrated in FIG. 4), an enzymatic reaction is needed to efficiently produce PD1 carrying the 10R,17S-dihydroxy-trans, trans, cis configuration arising from an epoxide intermediate as depicted in FIG. 4, Panel B.

Anti-inflammatory Actions of PD1—As indicated above, the complete stereochemical assignment for synthetic PD1 also relied on determining biological action of the related isomers. Earlier results indicated that PD1's anti-inflammatory properties were comprised of blocking leukocyte infiltration in murine systems (1, 3, 32, 37). Results in FIG. 5 show that synthetic PD1 reduced PMN transmigration in response to leukotriene $B_4$. Amounts as small as 1.0 μM gave 30% inhibition. The Δ15-trans isomer of PD1, where the conjugated triene portion of the molecule was in the trans configuration, did not block PMN transmigration in vitro. Although PD1 is a potent inhibitor in neutrophil transmigration, the degree of inhibition observed with monolayers of human microvascular endothelial cells and human neutrophils from >5 separate donors did not achieve values greater than 50% inhibition in each experiment.

These experiments with transmigration were carried out in parallel with murine acute inflammation. In these, acute peritonitis was initiated by challenge with the microbial isolate zymosan A and the actions of five isomers were assessed in vivo. Two compounds (Compound V and Compound VI) were excluded from matching with PD1 because the physical retention times on LC and GC-MS (FIG. 1 and FIG. 8) and biosynthetic considerations indicated that they were not likely candidates for endogenous human PD1 or isomers produced. It is noteworthy that PD1 (Compound II, FIG. 2) at doses as low as 1 ng per mouse gave striking inhibition of PMN infiltration within the exudates. In these experiments, the double dioxygenation product 10S,17S-docosatriene (Compound I) was substantially less potent. In this context, the double dioxygenation product was not active at 0.1 ng compared directly to synthetic PD1. At higher doses, 10S, 17S—HDHA (Compound I) blocked PMN infiltration, but it was less potent than PD1. Compound IV, which is the 10R version of the double dioxygenation products, was essentially equipotent at a 1 ng dose (Compound IV≈Compound I) but did not increase potency in a dose-dependent fashion at 10 ng and 100 ng doses (not shown). The Δ15-trans isomer of PD1 was, at equal doses of 1 ng/mouse, substantially less potent. Also, a rogue isomer for this series, Compound V (FIG. 2) was not likely to be produced in vivo from the 17S-hydroxy precursor because its 10S,17R-diHDHA was essentially without activity in this dose range. Of interest, Compound VI was the most potent of these isomers in vivo. However, only trace amounts were noted in human PMN extracts. Hence, a rank order of potency at the 0.1 ng dose of these 10,17-diHDHA isomers was Compound VI>>PD1>10S,17S-DT (the double dioxygenation product)>the Δ15-trans-PD1>>Compound V. The carboxy methyl ester of PD1 was also tested versus the native synthetic PD1. FIG. 6, Panel B demonstrates the potent dose response of PD1 as it dramatically reduced the infiltration of PMN into the peritoneum. The carbon 1-position carboxy-methyl ester was similar in its ability to block in vivo the hallmark of acute inflammation, namely PMN infiltration. The methyl ester of Compound VI also proved to be a potent regulator of PMN infiltration.

Can PD1 Stop Inflammation After Its Initiation?—Next, PD1 or its methyl ester was tested to determine if it could reduce leukocyte infiltration once inflammation had already been initiated. Results in FIG. 7A indicate that doses as low as 1 ng PD1/mouse diminished infiltration of PMN when administered i.p. following 2 h after challenge with zymosan in vivo. Similar and striking results were obtained with the carboxy methyl ester of PD1, also administered i.p. Hence, once PD1 was given, essentially no further infiltration of PMN into the peritoneum was obtained with essentially >90% blocking of further PMN infiltration to the site. The anti-inflammatory actions of DHA-derived PD1 and EPA-derived resolvin E1 were evaluated for synergistic or additive effects in vivo. RvE1 is derived from EPA and is another omega-3-derived counterregulatory anti-inflammatory lipid mediator recently isolated and identified (3, 45). When administered together, RvE1 and PD1 both reduced the infiltration of PMN in vivo during zymosan-induced peritonitis (FIG. 7B). These results indicate that they have a potential additive rather than synergistic anti-inflammatory action when administered together in vivo. A chemically more stable form of synthetic PD1, i.e., 15,16-dehydro-PD1, was prepared and tested that proved to retain activity in vivo, reducing PMN infiltration, albeit was slightly less potent than the native PD1 (FIG. 9). Of interest, differential counts on light microscopy also revealed that both PD1 and its chemical analog 15,16-dehydro-PD1 reduced PMN infiltration and increased the non-phlogistic recruitment of monocytes and lymphocytes (FIG. 8) while reducing inflammation, a hallmark of resolution (17, 31).

PD1 is present in asthma and endogenously generated in allergic lung—To determine if DHA-derived products are generated in respiratory tissues, lipid extracts from exhaled breath condensates (EBCs) were analyzed that were collected from healthy volunteer subjects and patients in the emergency department during a clinical exacerbation of asthma (FIG. 10). PD1 and its biosynthetic precursor, 17(S)-hydroxy-DHA were present in these human respiratory tract secretions (FIG. 11). Levels of PD1 were significantly lower in EBCs from subjects with status asthmaticus (trace amounts) compared to healthy individuals (2.23+/−1.55 ng PD1/ml EBC, mean+/− SEM, P<0.05). These results indicate that asthma exacerbation is associated with reduced airway levels of the counter-regulatory lipid mediator PD1.

To investigate potential roles for PD1 in airway inflammation, an experimental animal model of allergic asthma was studied. After sensitization and aerosol challenge with allergen, murine lungs generated PD1 from endogenous sources (73.9+/−35.6 ng PD1, mean+/−SEM for n=3). Of note, PD1 levels in the inflamed lungs were not significantly different from those in healthy murine lungs (45.8 ng PD1). Similar to results with human EBCs, 17(S)-hydroxy-DHA was also present in murine lungs. Addition of exogenous DHA to a homogenate of the inflamed murine lungs ex vivo significantly increased mean PD1 levels by 5.8-fold to 431.6+/−69.3 ng PD1 (mean+/−SEM, n1=3, P<0.02). These findings indicate that during airway inflammation, respiratory tissues can convert DHA to 17(S)-hydroxy-DHA and PD1.

Figure 13:
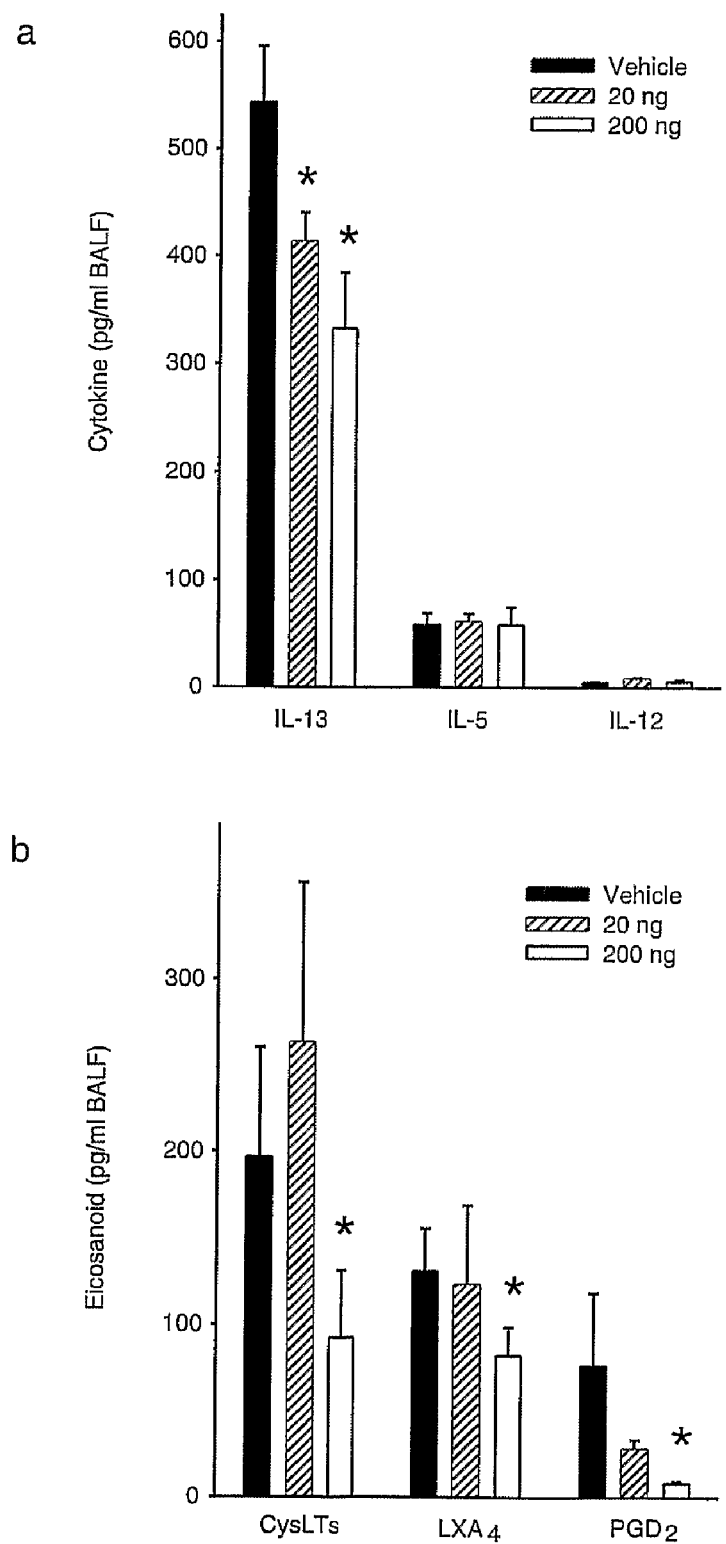
FIG. 13: PD1 decreases airway mucus. Representative lung tissue sections from mice given PD1 (a, 200 ng, b, 20 ng) or (c) vehicle were stained with periodic acid Schiff (magnifications: ×20 (left column), ×40 (right column). Arrows indicate representative mucus (magenta) containing goblet cells.
Figure 14:
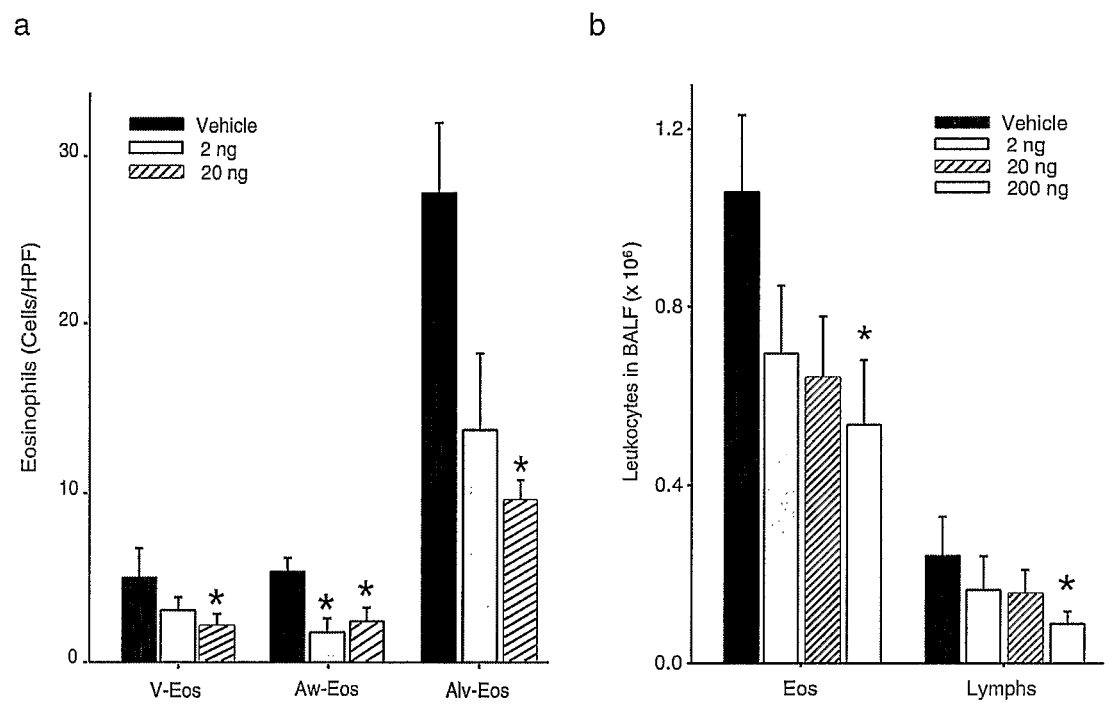
FIG. 14: PD1 sharply reduces leukocyte infiltration. (a), Tissue morphometric analyses were performed to determine the impact of PD1 on EOS accumulation in pulmonary vessels (V-EOS), large airways (Aw-EOS) and alveoli (Alv-EOS). (b), BALFs were obtained from OVA sensitized and challenged mice. Leukocytes in BALF were enumerated and identified after Wright-Giemsa stain. Results are expressed as mean±SEM (n≧3). *P<0.05 by Student's t-test compared to control animals.
Figure 15:
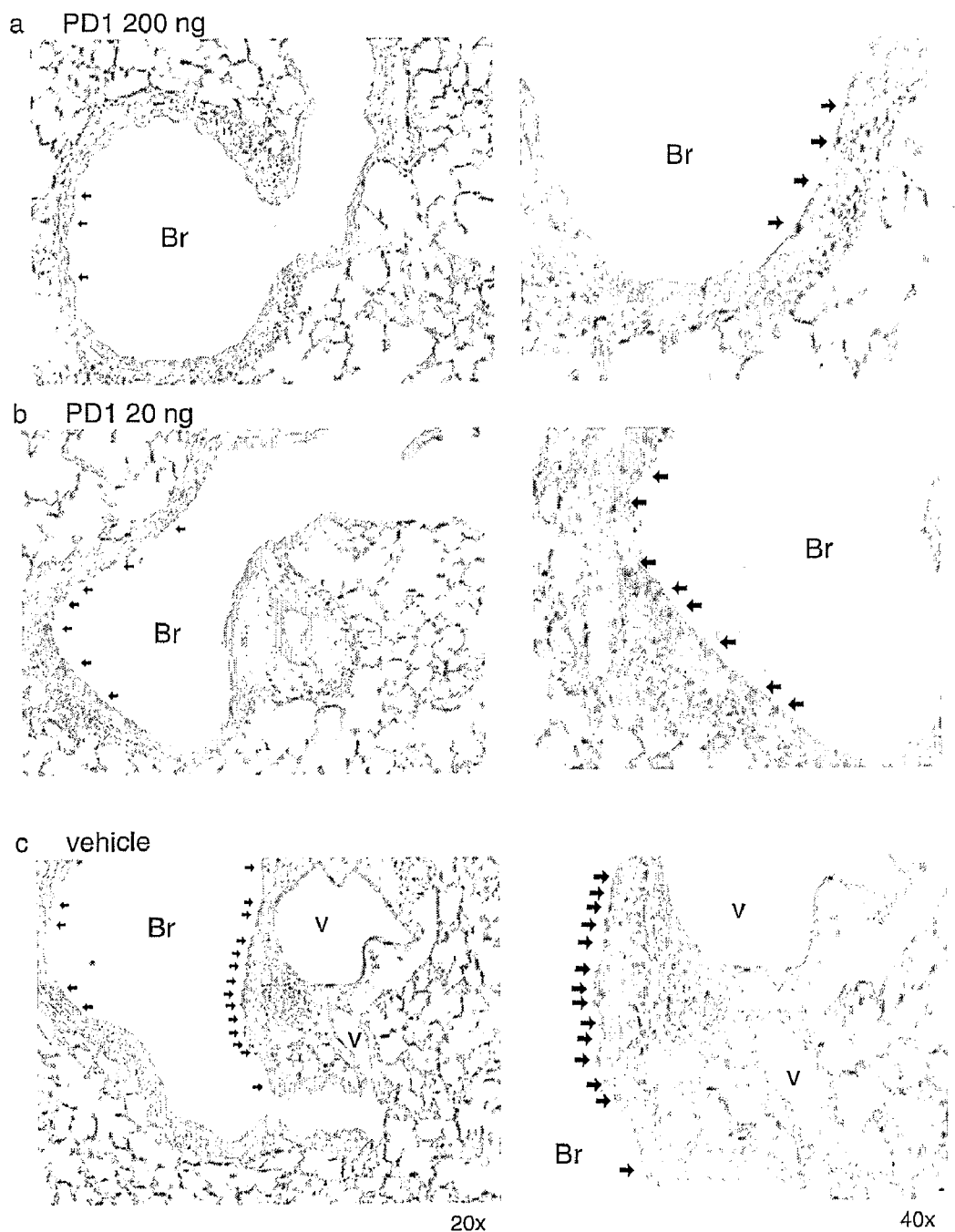
FIG. 15: PD1 selectively decreases airway inflammatory mediators. In the presence or absence of PD1, the mediator profile in BALF was determined in materials from OVA sensitized and challenged mice for specific (a) cytokines (IL-13, IL-5, IL-12), and (b) lipid mediators (CysLTs, LXA$_4$ and PGD$_2$). Results are expressed as mean±SEM (n≧5, d=2). *P<0.05 by Student's t-test compared to control animals.

Allergic airway inflammation decreases with PD1—To determine the impact of PD1 on airway inflammation, physiologically relevant quantities (2, 20 or 200 ng) were administered by intravenous injection to allergen-sensitized animals just prior (30 min) to each aerosol challenge. For these experiments, PD1 was produced via biogenic synthesis and matching studies were performed with PD1 that was prepared by total organic synthesis (62). Animals receiving PD1 had substantially less EOS and Lymphs in the peribronchial regions and airspaces compared to control mice that received only vehicle (FIG. 12). PD1 also reduced goblet cell hyperplasia and airway mucus as determined by periodic acid Schiff stain (FIG. 13). Morphometric analyses identified significant decreases in EOS tissue infiltration around vessels and in the large and peripheral airways (FIG. 14a). In BALF, PD1 decreased total leukocytes, EOS, and Lymphs in a concentration-dependent manner (FIG. 14b), and levels of peptide and lipid pro-inflammatory mediators were selectively reduced (FIG. 15). PD1 administration blocked allergen-induced increases in IL-13, CysLTs and $PGD_2$, all of which have been assigned pivotal roles in asthma pathobiology (63-65). Of note, PD1 did not significantly impact IL-5 or IL-12 levels in BALF. In conjunction with decreased airway inflammation, levels of the counter-regulatory eicosanoid $LXA_4$ were diminished in the presence of PD1 (FIG. 14b). No behavioral or physical signs of toxicity with PD1 treatment were observed. Together, these results indicate that PD1, in nanogram quantities, significantly reduced allergic pulmonary inflammation, and suggests that its mechanism of action is distinct from LXs.

PD1 blocks airway hyper-responsiveness—Because increased airway reactivity is a diagnostic hallmark of asthma, it was also determined whether PD1 regulated airway hyper-responsiveness to inhaled methacholine. After allergen sensitization and aerosol challenge in the presence of PD1 (0-200 ng), animals were ventilated and exposed (10 sec) to increasing concentrations of inhaled methacholine. Consistent with the regulation of airway inflammation, PD1 also decreased both peak and average lung resistance in response to methacholine (FIG. 16). The log $ED_{200}$ for the mean airway resistance for all three doses of PD1 (2, 20 and 200 ng) was significantly increased compared with vehicle (FIG. 16b). There was a bell-shaped dose response with maximal protection for PD1 on airway hyper-responsiveness to methacholine apparent with lower amounts (2 and 20 ng). PD1 displayed no significant impact on the airway responses of control animals that received PBS rather than allergen (FIG. 16b). In addition, no significant changes in lung elastance or compliance were observed with PD1 following allergen challenge (data not shown). These results indicate that methacholine-induced bronchoconstriction is significantly reduced by administration of PD1.

Figure 17:
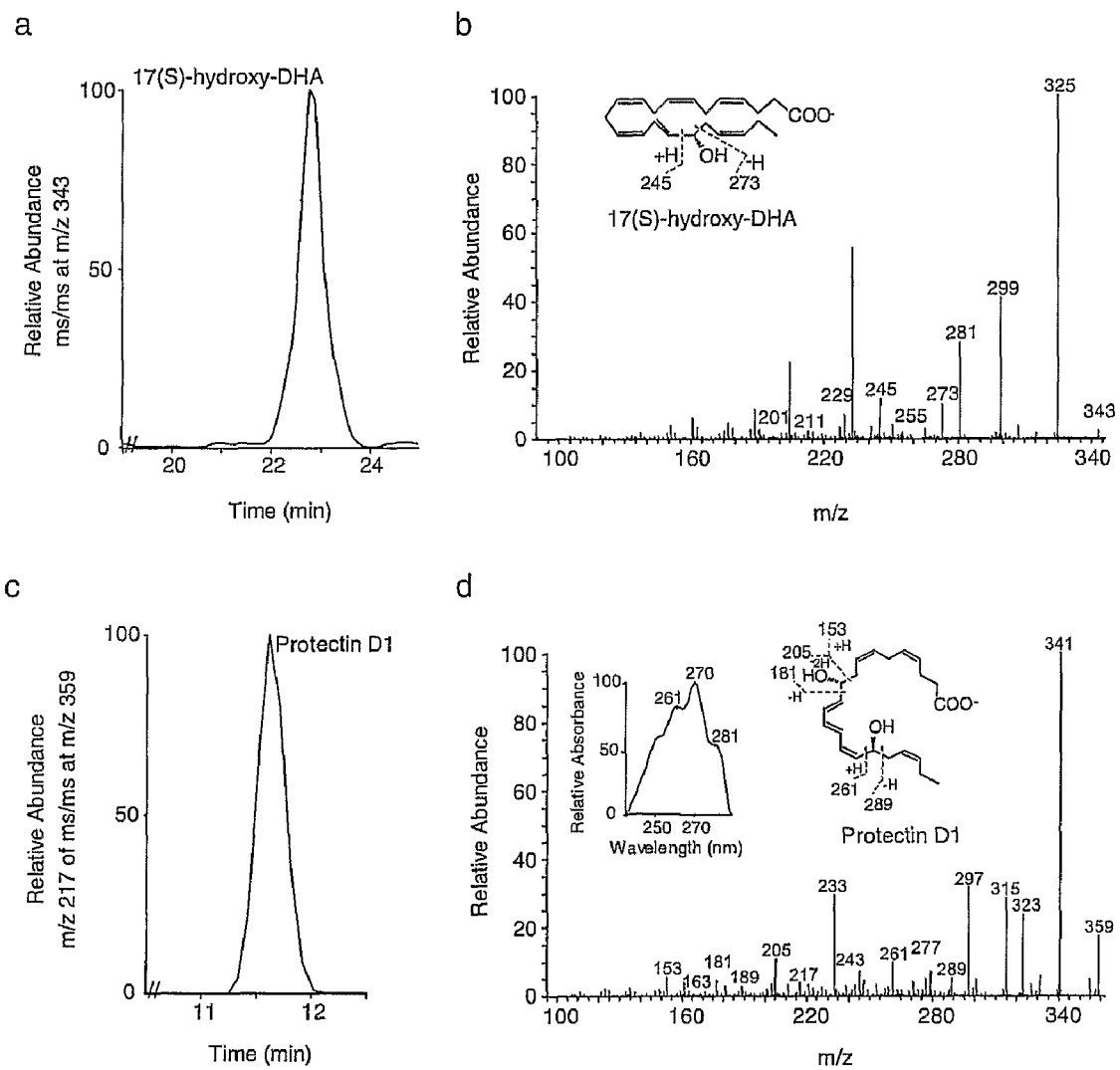
FIG. 17: PD1 treatment promotes resolution of allergen-driven leukocytes in mouse lung. BALFs were obtained from OVA sensitized and challenged mice that received either PD1 (20 ng, hatched bars) or vehicle (0.9% saline, black bars) for three consecutive days prior to study. Leukocytes in BALF were enumerated and identified after Wright-Giemsa stain. Results are expressed as mean±SEM (n≧3). *P<0.05 by Student's t-test compared to control animals.

Impact of PD1 treatment on airway inflammation—To more closely mimic the clinical scenario of asthma exacerbation, it was next determined whether PD1 could dampen established airway inflammation by administration after aeroallergen challenge. Mice were sensitized and allergen challenged on four consecutive days. PD1 (20 ng, iv) or vehicle (0.9% saline) was then given once a day for three additional days and BAL was performed to enumerate cellular infiltration into the lung. Despite no further aeroallergen challenges, animals receiving vehicle still carry a substantial number of EOS and Lymphs in BALF at day 21 in our protocol (FIG. 17). In sharp contrast, PD1 administration led to significant decrements in the numbers of total leukocytes, Eos and Lymphs in BALFs (FIG. 17). These findings indicated that PD1 has the capacity to accelerate resolution of allergic airway inflammation.

PD1 is identified as a natural product of a new C22:6 signaling pathway during respiratory tract inflammation that displays potent counter-regulatory actions on key asthma phenotypes, namely airway levels of pro-inflammatory peptide and lipid mediators, airway mucus, leukocyte accumulation and hyper-responsiveness. The present invention provides for the first identification of 17S-hydroxy-DHA and PD1 in human asthma. In addition, airway inflammation triggered PD1 formation in vivo and conversion of C22:6 to PD1 in lung tissues. Similar to the inflamed airway, generation of PD1 occurs elsewhere during multicellular host inflammatory responses, including Alzheimer disease, brain ischemia-reperfusion injury and activated human whole blood (52, 53, 66). The biosynthesis of PD1 proceeds via 15-lipoxygenase-catalyzed conversion of DHA to 17S-hydroperoxy and 16(17)-epoxide intermediates in activated human leukocytes and in Alzheimer's brain and murine cornea (53, 62, 67, 68). Lipoxygenases and epoxide hydrolases are both prominent classes of enzymes in asthmatic lung that are induced by pivotal regulators of allergy, including specific $T_H2$ cytokines (69-72). Potential source(s) for PD1 generation include airway epithelial cells, EOS and other leukocytes, but the definitive cellular and enzymatic source of PD1 in the lung remains to be established in future studies. The present invention provides that the presence of specialized enzyme systems in the lung for this new DHA pathway that convert the omega-3 fatty acid to biologically active chemical mediators during airway inflammation.

Eosinophilic airway inflammation and airway hyper-responsiveness are characteristic features of asthma. EOS recruitment to the lung in asthma is primarily a consequence of $T_H2$ lymph activation (50). Because PD1 was identified in EBCs in the ng range and this sampling technique likely reflects only a small fraction of total PD1 generated in the lung, the impact of PD1 was examined in physiologically relevant ng quantities. After allergen sensitization and aerosol challenge, EOS trafficking was reduced by as little as 2 ng of PD1. Levels of $T_H2$ cytokines in BALF and the number of Lymphs in both BALF and lung tissue were decreased. These findings provide evidence for potent, concentration-dependent reduction of both $T_H2$ Lymphs and EOS responses in vivo. Lymph and EOS activation in the lung are held to contribute to asthma pathobiology. In addition, neutrophil (PMN) activation contributes to the pathogenesis of asthma exacerbation (73) and severity (74). PD1 promotes T-lymph apoptosis in vitro (67), and PD1 also carries systemic and topical anti-inflammatory actions for PMNs in vivo (52, 66). In the nervous system, PD1 decreases brain leukocyte infiltration, IL-1β-induced NFκB activation and COX-2 expression to elicit neuroprotection (61, 66). Here, PD1 also dampened hyper-responsiveness to methacholine and mucus production in the inflamed airway. The local generation of PD1 in allergic inflammation together with counter-regulatory properties in the airway broadens its potential cellular sources and actions in vivo to new leukocyte classes and tissue resident cells and points to a more generalized counter-regulatory function as an autacoid in inflammation.

LXs are also generated in asthma and serve as potent inhibitors of both airway inflammation and hyper-responsiveness (75). While there is some overlap in the pattern of cytokine regulation for PD1 and a LX stable analog in this murine model of asthma, some key differences were observed. First, while both mediators blocked IL-13 and CysLT generation and had no significant effect on BAL IL-12 levels (75), the inhibitory concentrations of PD1 were 1 to 2 log orders more potent than the LX analog. Secondly, IL-5 production was reduced by the LX stable analog, but not PD1, suggesting a direct effect of PD1 on EOS, T Lymphs and other effector cells. Third, administration of PD1 led to decreased airway levels of $LXA_4$, suggesting that the circuit for PD1 formation and actions is distinct from LX signaling in the murine lung. In aggregate, these findings indicate the presence of unique homeostatic pathways for DHA derived bioactive mediators in the lung.

It is interesting to note that formation of counter-regulatory LXs is defective in severe inflammatory diseases of the airways, including asthma and cystic fibrosis (76-78). DHA levels in the respiratory tract are decreased in both of these illnesses (55), and here, in comparison to healthy controls, it was uncovered that there are lower levels of PD1 during human asthma exacerbation. Given its counter-regulatory properties, decreased formation of PD1 from low levels of DHA would adversely impact control of airway inflammation and hyper-responsiveness. While observational studies have identified an increased risk of asthma in populations with diets low in DHA, interventional trials with DHA supplementation have not consistently improved clinical outcomes (79), despite altering the responses of isolated leukocytes to inflammatory stimuli (80). In contrast, nutritional supplementation with omega-3 essential fatty acids has proven beneficial in cystic fibrosis and the acute respiratory distress syndrome, clinical disorders of excess PMN-mediated inflammation (81, 82). Because the molecular rationale for these beneficial effects is uncertain, there remain many potential reasons for the lack of clinical success with DHA feeding in asthma, including purity, dose, time course and difficulties tolerating the ingestion of large amounts of fish oils for extended periods of time (83). After the induction of experimental asthma by aeroallergen challenge, we determined that administration of PD1 promoted the resolution of airway inflammation. Thus, identification of PD1 as a DHA-derived counter-regulatory autacoid in the lung opens the door to new mechanism-based therapeutic strategies in airway inflammation.

The present results are the first demonstration of PD1 formation in human asthma in vivo from DHA and identify direct protective and regulatory roles for this novel mediator in allergic inflammation and airway hyper-responsiveness. In light of its ability to strongly reduce both of these key asthma phenotypes, the PD1 pathway may offer new therapeutic approaches for asthma. Moreover, the results indicate that endogenous conversion of DHA to PD1 represents a potential mechanism for the therapeutic benefits derived from diets rich in this omega-3 essential fatty acid in maintaining respiratory homeostasis.

REFERENCES

1. Hong, S., K. Gronert, P. Devchand, R.-L. Moussignac, and C. N. Serhan. 2003. Novel docosatrienes and 17S-resolvins generated from docosahexaenoic acid in murine brain, human blood and glial cells: autacoids in anti-inflammation. J. Biol. Chem. 278: 14677-14687.
2. Mulherjee, P. K., V. L. Marcheselli, C. N. Serhan, and N. G. Bazan. 2004. Neuroprotectin D1: a docosahexaenoic acid-derived docosatriene protects human retinal pigment epithelial cells from oxidative stress. Proc. Natl. Acad. Sci. USA 101: 8491-8496.
3. Serhan, C. N., S. Hong, K. Gronert, S. P. Colgan, P. R. Devchand, G. Mirick, and R.-L. Moussignac. 2002. Resolvins: a family of bioactive products of omega-3 fatty acid transformation circuits initiated by aspirin treatment that counter pro-inflammation signals. J. Exp. Med. 196: 1025-1037.
4. Majno, G., and I. Joris. 2004. Cells, Tissues, and Disease: Principles of General Pathology. Oxford University Press, New York.

5. Coussens, L. M., and Z. Werb. 2002. Inflammation and cancer. Nature 420: 860-867.
6. Libby, P. 2002. Inflammation in atherosclerosis. Nature 420: 868-878.
7. Weiner, H. L., and D. J. Selkoe. 2002. Inflammation and therapeutic vaccination in CNS diseases. Nature 420: 879-884.
8. Nathan, C. 2002. Points of control in inflammation. Nature 420: 846-852.
9. Samuelsson, B., S. E. Dahlén, J. Å. Lindgren, C. A. Rouzer, and C. N. Serhan. 1987. Leukotrienes and lipoxins: structures, biosynthesis, and biological effects. Science 237: 1171-1176.
10. McMahon, B., and C. Godson. 2004. Lipoxins: endogenous regulators of inflammation. Am. J. Physiol. Renal Physiol. 286: F189-F201.
11. Serhan, C. N. 1994. Lipoxin biosynthesis and its impact in inflammatory and vascular events. Biochim. Biophys. Acta 1212: 1-25.
12. Wallace, J. L., and S. Fiorucci. 2003. A magic bullet for mucosal protection. and aspirin is the trigger! Trends Pharmacol. Sci. 24: 323-326.
13. Levy, B. D., C. B. Clish, B. Sclunidt, K. Gronert, and C. N. Serhan. 2001. Lipid mediator class switching during acute inflammation: signals in resolution. Nature Immunol. 2: 612-619.
14. Godson, C., S. Mitchell, K. Harvey, N. A. Petasis, N. Hogg, and H. R. Brady. 2000. Cutting edge: Lipoxins rapidly stimulate nonphlogistic phagocytosis of apoptotic neutrophils by monocyte-derived macrophages. J. Immunol. 164: 1663-1667.
15. Maddox, J. F., and C. N. Serhan. 1996. Lipoxin A4 and B4 are potent stimuli for human monocyte migration and adhesion: selective inactivation by dehydrogenation and reduction. J. Exp. Med. 183: 137-146.
16. Gilroy, D. W., T. Lawrence, M. Perretti, and A. G. Rossi. 2004. Inflammation resolution: new opportunities for drug discovery. Nat. Rev. Drug Discov. 3: 401-416.
17. Serhan, C. N. 2004. A search for endogenous mechanisms of anti-inflammation uncovers novel chemical mediators: missing links to resolution. Histochem. Cell Biol. 122: 305-321.
18. Serhan, C. N., C. B. Clish, J. Brannon, S. P. Colgan, N. Chiang, and K. Gronert. 2000. Novel functional sets of lipid-derived mediators with antiinflammatory actions generated from omega-3 fatty acids via cyclooxygenase 2-nonsteroidal antiinflammatory drugs and transcellular processing. J. Exp. Med. 192: 1197-1204.
19. Serhan, C. N., K. Gotlinger, S. Hong, and M. Arita. 2004. Resolvins, docosatrienes, and neuroprotectins, novel omega-3-derived mediators, and their aspirin-triggered endogenous epimers: an overview of their protective roles in catabasis. Prostaglandins Other Lipid Mediat. 73: 155-172.
20. Burr, G. O., and M. M. Burr. 1929. A new deficiency disease produced by the rigid exclusion of fat from the diet. J. Biol. Chem. 82: 345.
21. Camuesco, D., J. Galvez, A. Nieto, M. Comalada, M. E. Rodriguez-Cabezas, A. Concha, J. Xaus, and A. Zarzuelo. 2005. Dietary olive oil supplemented with fish oil, rich in EPA and DHA (n-3) polyunsaturated fatty acids, attenuates colonic inflammation in rats with DSS-induced colitis. J. Nutr. 135: 687-694.
22. Billman, G. E., J. X. Kang, and A. Leaf. 1999. Prevention of sudden cardiac death by dietary pure w-3 polyunsaturated fatty acids in dogs. Circulation 99: 2452-2457.
23. Marchioli, R., F. Barzi, E. Bomba, C. Chieffo, D. Di Gregorio, R. Di Mascio, M. G. Franzosi, E. Geraci, G. Levantesi, A. P. Maggioni, L. Mantini, R. M. Marfisi, G. Mastrogiuseppe, N. Mininni, G. L. Nicolosi, M. Santini, C. Schweiger, L. Tavazzi, G. Tognoni, C. Tucci, and F. Valagussa. 2002. Early protection against sudden death by n-3 polyunsaturated fatty acids after myocardial infarction: time-course analysis of the results of the Gruppo Italiano per lo Studio della Sopravvivenza nell'Infarto Miocardico (GISSI)-Prevenzione. Circulation 105: 1897-1903.
24. Holub, D. J., and B. J. Holub. 2004. Omega-3 fatty acids from fish oils and cardiovascular disease. Mol. Cell. Biochem. 263: 217-225.
25. Engler, M. M., M. B. Engler, M. Malloy, E. Chiu, D. Besio, S. Paul, M. Stuehlinger, J. D. Morrow, P. M. Ridker, N. Rifai, and M. Mietus-Snyder. 2004. Docosahexaenoic acid restores endothelial function in children with hyperlipidemia: results from the EARLY study. Int. J. Clin. Pharmacol. Ther. 42: 672-679.
26. Lim, G. P., F. Calon, T. Morihara, F. Yang, B. Teter, O. Ubeda, N. Salem, Jr., S. A. Frautschy, and G. M. Cole. 2005. A diet enriched with the omega-3 fatty acid docosahexaenoic acid reduces amyloid burden in an aged Alzheimer mouse model. J. Neurosci. 25: 3032-3040.
27. Bazan, N. G. 1990. Supply of n-3 polyunsaturated fatty acids and their significance in the central nervous system. In Nutrition and the Brain, Vol. 8. R. J. Wurtman, and J. J. Wurtman, eds. Raven Press, New York. 1-22.
28. Salem, N., Jr., B. Litman, H.-Y. Kim, and K. Gawrisch. 2001. Mechanisms of action of docosahexaenoic acid in the nervous system. Lipids 36: 945-959.
29. Bazan, N. G., D. L. Birkle, and T. S. Reddy. 1984. Docosahexaenoic acid (22:6, n-3) is metabolized to lipoxygenase reaction products in the retina. Biochem. Biophys. Res. Commun. 125: 741-747.
30. Sawazaki, S., N. Salem, Jr., and H.-Y. Kim. 1994. Lipoxygenation of docosahexaenoic acid by the rat pineal body. J. Neurochem. 62: 2437-2447.
31. Bannenberg, G. L., N. Chiang, A. Ariel, M. Arita, E. Tjonahen, K. H. Gotlinger, S. Hong, and C. N. Serhan. 2005. Molecular circuits of resolution: Formation and actions of resolvins and protectins. J. Immunol. 174: 4345-4355.
32. Marcheselli, V. L., S. Hong, W. J. Lukiw, X. Hua Tian, K. Gronert, A. Musto, M. Hardy, J. M. Gimenez, N. Chiang, C. N. Serhan, and N. G. Bazan. 2003. Novel docosanoids inhibit brain ischemia-reperfusion-mediated leukocyte infiltration and pro-inflammatory gene expression. J. Biol. Chem. 278: 43807-43817.
33. Belayev, L., V. L. Marcheselli, L. Khoutorova, E. B. Rodriguez de Turco, R. Busto, M. D. Ginsberg, and N. G. Bazan. 2005. Docosahexaenoic acid complexed to albumin elicits high-grade ischemic neuroprotection. Stroke 36: 118-123.
34. Gronert, K., N. Maheshwari, N. Khan, I. R. Hassan, M. Dunn, and M. L. Schwartzman. 2005. A role for the mouse 12/15-lipoxygenase pathway in promoting epithelial wound healing and host defense. J. Biol. Chem. 280: 15267-15278.
35. Hong, S., E. Tjonahen, E. L. Morgan, L. Yu, C. N. Serhan, and A. F. Rowley. 2005. Rainbow trout (Oncorhynchus mykiss) brain cells biosynthesize novel docosahexaenoic acid-derived resolvins and protectins—mediator lipidomic analysis. Prostaglandins Other Lipid Mediat. in press (Epub Jun. 13, 2005).

36. Lu, Y., S. Hong, E. Tjonahen, and C. N. Serhan. 2005. Mediator-lipidomics: databases and search algorithms for PUFA-derived mediators. J. Lipid Res. 46: 790-802.
37. Serhan, C. N. 2004. Resolvins: biotemplates for novel therapeutic interventions. U.S. Patent Application Publication 2004/0116408 A1, Jun. 17, 2004 (sections 0400-0404). Previously filed on Aug. 12, 2002 as U.S. Provisional Application Ser. No. 60/402,798.
38. Serhan, C. N., and C. B. Clish. 2003. Aspirin-triggered lipid mediators. U.S. Pat. No. 6,670,396 B2, Dec. 30, 2003.
39. Serhan, C. N., K. C. Nicolaou, S. E. Webber, C. A. Veale, S. E. Dahlen, T. J. Puustinen, and B. Samuelsson. 1986. Lipoxin A. Stereochemistry and biosynthesis. J Biol Chem 261: 16340-16345.
40. Gronert, K., C. B. Clish, M. Romano, and C. N. Serhan. 1999. Transcellular regulation of eicosanoid biosynthesis. In Eicosanoid Protocols. E. A. Lianos, ed. Humana Press, Totowa, N.J. 119-144.
41. Serhan, C. N., J. F. Maddox, N. A. Petasis, I. Akritopoulou-Zanze, A. Papayianni, H. R. Brady, S. P. Colgan, and J. L. Madara. 1995. Design of lipoxin A4 stable analogs that block transmigration and adhesion of human neutrophils. Biochemistry 34: 14609-14615.
42. Maas, R. L., J. Turk, J. A. Oates, and A. R. Brash. 1982. Formation of a novel dihydroxy acid from arachidonic acid by lipoxygenase-catalyzed double oxygenation in rat mononuclear cells and human leukocytes. J. Biol. Chem. 257: 7056-7067.
43. Serhan, C. N. 1989. On the relationship between leukotriene and lipoxin production by human neutrophils: evidence for differential metabolism of 15-HETE and 5-HETE. Biochim. Biophys. Acta 1004: 158-168.
44. Serhan, C. N., and B. Samuelsson. 1988. Lipoxins: a new series of eicosanoids (biosynthesis, stereochemistry, and biological activities). Adv. Exp. Med. Biol. 229: 1-14.
45. Arita, M., M. Yoshida, S. Hong, E. Tjonahen, J. N. Glickman, N. A. Petasis, R. S. Blumberg, and C. N. Serhan. 2005. Resolvin E1, a novel endogenous lipid mediator derived from omega-3 eicosapentaenoic acid, protects against TNBS-induced colitis. Proc. Natl. Acad. Sci. USA 102: 7671-7676.
46. Kuhn, H., A. R. Brash, R. Wiesner, and L. Alder. 1988. Lipoxygenase catalyzed oxygenation of hydroxy fatty acids to lipoxins. Adv. Exp. Med. Biol. 229: 39-49.
47. Whelan, J. 1988. Arachidonic acid cascade: the 5-lipoxygenase pathway. Ph.D. thesis, Department of Nutrition, Pennsylvania State University, University Park.
48. Whelan, J., P. Reddanna, V. Nikolaev, G. R. Hildenbrandt, and T. S. Reddy. 1990. The unique characteristics of the purified 5-lipoxygenase from potato tubers and the proposed mechanism of formation of leukotrienes and lipoxins. In Biological Oxidation Systems, Vol. 2. Academic Press. 765-778.
49. Butovich, I. A., M. Hamberg, and O. Rådmark. 2005. Novel oxylipins formed from docosahexaenoic acid by potato lipoxygenase-10(S)-hydroxydocosahexaenoic acid and 10,20-dihydroxydocosahexaenoic acid. Lipids 40: 249-257.
50. Busse, W. W., and R. F. Lemanske, Jr. 2001. Asthma. New England Journal of Medicine 344:350-362.
51. Levy, B. D. 2005. Lipoxins and lipoxin analogs in asthma. Prostaglandins Leukot Essent Fatty Acids 73:231-237.
52. Hong, S., K. Gronert, P. R. Devchand, R. L. Moussignac, and C. N. Serhan. 2003. Novel docosatrienes and 17S-resolvins generated from docosahexaenoic acid in murine brain, human blood, and glial cells. Autacoids in anti-inflammation. Journal of Biological Chemistry. 278: 14677-14687.
53. Lukiw, W. J., J. G. Cui, V. L. Marcheselli, M. Bodker, A. Botkjaer, K. Gotlinger, C. N. Serhan, and N. G. Bazan. 2005. A role for docosahexaenoic acid-derived neuroprotectin D1 in neural cell survival and Alzheimer disease. J Clin Invest. 115:2774-2783.
54. Serhan, C. N., S. Hong, K. Gronert, S. P. Colgan, P. R. Devchand, G. Mirick, and R. L. Moussignac. 2002. Resolvins: a family of bioactive products of omega-3 fatty acid transformation circuits initiated by aspirin treatment that counter proinflammation signals. Journal of Experimental Medicine. 196:1025-1037.
55. Freedman, S. D., P. G. Blanco, M. M. Zaman, J. C. Shea, M. Ollero, I. K. Hopper, D. A. Weed, A. Gelrud, M. M. Regan, M. Laposata, J. G. Alvarez, and B. P. O'Sullivan. 2004. Association of cystic fibrosis with abnormalities in fatty acid metabolism. New England Journal of Medicine. 350:560-569.
56. Peat, J. K., C. M. Salome, and A. J. Woolcock. 1992. Factors associated with bronchial hyperresponsiveness in Australian adults and children. Eur Respir J 5:921-929.
57. Schwartz, J., and S. T. Weiss. 1994. The relationship of dietary fish intake to level of pulmonary function in the first National Health and Nutrition Survey (NHANES I). Eur Respir J 7:1821-1824.
58. Peat, J. K., S. Milirshahi, A. S. Kemp, G. B. Marks, E. R. Tovey, K. Webb, C. M. Mellis, and S. R. Leeder. 2004. Three-year outcomes of dietary fatty acid modification and house dust mite reduction in the Childhood Asthma Prevention Study. J Allergy Clin Immunol 114:807-813.
59. Henson, P. M. 2005. Dampening inflammation. Nature Immunology. 6:1179-1181.
60. Serhan, C. N., and J. Savill. 2005. Resolution of inflammation: the beginning programs the end. Nature Immunology. 6:1199-1205.
61. Mulcherjee, P. K., V. L. Marcheselli, C. N. Serhan, and N. G. Bazan. 2004. Neuroprotectin D1: a docosahexaenoic acid-derived docosatriene protects human retinal pigment epithelial cells from oxidative stress. Proceedings of the National Academy of Sciences of the United States of America 101:8491-8496.
62. Serhan, C. N., K. Gotlinger, S. Hong, Y. Lu, J. Siegelman, T. Baer, R. Yang, S. P. Colgan, and N. A. Petasis. 2006. Anti-inflammatory actions of neuroprotectin D1/protectin D1 and its natural stereoisomers: assignments of dihydroxy-containing docosatrienes. J. Immunol. 176:1848-1859.
63. Wills-Karp, M., J. Luyimbazi, X. Xu, B. Schofield, T. Y. Neben, C. L. Karp, and D. D. Donaldson. 1998. Interleukin-13: central mediator of allergic asthma. Science. 282: 2258-2261.
64. Vachier, I., M. Kumlin, S. E. Dahlen, J. Bousquet, P. Godard, and P. Chanez. 2003. High levels of urinary leukotriene E4 excretion in steroid treated patients with severe asthma. Respiratory Medicine 97:1225-1229.
65. Matsuoka, T., M. Hirata, H. Tanaka, Y. Takahashi, T. Murata, K. Kabashima, Y. Sugimoto, T. Kobayashi, F. Ushikubi, Y. Aze, N. Eguchi, Y. Urade, N. Yoshida, K. Kimura, A. Mizoguchi, Y. Honda, H. Nagai, and S, Narumiya. 2000. Prostaglandin D2 as a mediator of allergic asthma. Science. 287:2013-2017.
66. Marcheselli, V. L., S. Hong, W. J. Lukiw, X. H. Tian, K. Gronert, A. Musto, M. Hardy, J. M. Gimenez, N. Chiang, C. N. Serhan, and N. G. Bazan. 2003. Novel docosanoids inhibit brain ischemia-reperfusion-mediated leukocyte infiltration and pro-inflammatory gene expression. Journal of Biological Chemistry. 278:43807-43817.
67. Ariel, A., P. L. Li, W. Wang, W. X. Tang, G. Fredman, S. Hong, K. H. Gotlinger, and C. N. Serhan. 2005. The docosatriene protectin D1 is produced by TH2 skewing and promotes human T cell apoptosis via lipid raft clustering. J Biol. Chem. 280:43079-43086.
68. Gronert, K., N. Maheshwari, N. Khan, I. R. Hassan, M. Dunn, and M. Laniado Schwartzman. 2005. A role for the mouse 12/15-lipoxygenase pathway in promoting epithelial wound healing and host defense. J Biol. Chem. 280: 15267-15278.
69. Nassar, G. M., J. D. Morrow, L. J. d. Roberts, F. G. Lakkis, and K. F. Badr. 1994. Induction of 15-lipoxygenase by interleukin-13 in human blood monocytes. Journal of Biological Chemistry 269:27631-27634.
70. Pouliot, M., P. P. McDonald, L. Khamzina, P. Borgeat, and S. R. McColl. 1994. Granulocyte-macrophage colony-stimulating factor enhances 5-lipoxygenase levels in human polymorphonuclear leukocytes. Journal of Immunology 152:851-858.
71. Munafo, D. A., K. Shindo, J. R. Baker, and T. D. Bigby. 1994. Leukotriene A4 hydrolase in human bronchoalveolar lavage fluid. Journal of Clinical Investigation. 93:1042-1050.
72. Zaitsu, M., Y. Hamasaki, M. Matsuo, A. Kuldta, K. Tsuji, M. Miyazaki, R. Hayasaki, E. Muro, S. Yamamoto, I. Kobayashi, T. Ichimaru, O. Kohashi, and S. Miyazaki. 2000. New induction of leukotriene A(4) hydrolase by interleukin-4 and interleukin-13 in human polymorphonuclear leukocytes. Blood. 96:601-609.
73. Fahy, J. V., K. W. Kim, J. Liu, and H. A. Boushey. 1995. Prominent neutrophilic inflammation in sputum from subjects with asthma exacerbation. Journal of Allergy & Clinical Immunology. 95:843-852.
74. Wenzel, S. E., S. J. Szefler, D. Y. Leung, S. I. Sloan, M. D. Rex, and R. J. Martin. 1997. Bronchoscopic evaluation of severe asthma. Persistent inflammation associated with high dose glucocorticoids. American Journal of Respiratory & Critical Care Medicine. 156:737-743.
75. Levy, B. D., G. T. De Sanctis, P. R. Devchand, E. Kim, K. Ackerman, B. A. Schmidt, W. Szczeklik, J. M. Drazen, and C. N. Serhan. 2002. Multi-pronged inhibition of airway hyper-responsiveness and inflammation by lipoxin A(4). Nature Medicine. 8:1018-1023.
76. Karp, C. L., L. M. Flick, K. W. Park, S. Softic, T. M. Greer, R. Keledjian, R. Yang, J. Uddin, W. B. Giggino, S. F. Atabani, Y. Belkaid, Y. Xu, J. A. Whitsett, F. J. Accurso, M. Wills-Karp, and N. A. Petasis. 2004. Defective lipoxin-mediated anti-inflammatory activity in the cystic fibrosis airway. Nature Immunology. 5:388-392.
77. Levy, B. D., C. Bonnans, E. S. Silvennan, L. J. Palmer, G. Marigowda, and E. Israel. 2005. Diminished Lipoxin Biosynthesis in Severe Asthma. Am J Respir Crit. Care Med 172: 824-830.
78. Sanak, M., B. D. Levy, C. B. Clish, N. Chiang, K. Gronert, L. Mastalerz, C. N. Serhan, and A. Szczeklik. 2000. Aspirin-tolerant asthmatics generate more lipoxins than aspirin-intolerant asthmatics. European Respiratory Journal. 16:44-49.
79. Woods, R. K., F. C. Thien, and M. J. Abramson. 2002. Dietary marine fatty acids (fish oil) for asthma in adults and children. [update of Cochrane Database Syst Rev. 2000; (4):CD001283; PMID: 11034708]. Cochrane Database of Systematic Reviews.: CD001283.
80. Lee, T. H., J. M. Mencia-Huerta, C. Shih, E. J. Corey, R. A. Lewis, and K. F. Austen. 1984. Effects of exogenous arachidonic, eicosapentaenoic, and docosahexaenoic acids on the generation of 5-lipoxygenase pathway products by ionophore-activated human neutrophils. Journal of Clinical Investigation. 74:1922-1933.
81. Beckles Willson, N., T. M. Elliott, and M. L. Everard. 2002. Omega-3 fatty acids (from fish oils) for cystic fibrosis. Cochrane Database of Systematic Reviews.: CD002201.
82. Gadek, J. E., S. J. DeMichele, M. D. Karlstad, E. R. Pacht, M. Donahoe, T. E. Albertson, C. Van Hoozen, A. K. Wennberg, J. L. Nelson, and M. Noursalehi. 1999. Effect of enteral feeding with eicosapentaenoic acid, gamma-linolenic acid, and antioxidants in patients with acute respiratory distress syndrome. Enteral Nutrition in ARDS Study Group. Critical Care Medicine. 27:1409-1420.
83. Spector, S. L., and M. E. Surette. 2003. Diet and asthma: has the role of dietary lipids been overlooked in the management of asthma? Annals of Allergy, Asthma, & Immunology. 90:371-377.

Although the present invention has been described with reference to preferred embodiments, persons skilled in the art will recognize that changes may be made in form and detail without departing from the spirit and scope of the invention. All references cited throughout the specification, including those in the background, are incorporated herein in their entirety. Those skilled in the art will recognize, or be able to ascertain, using no more than routine experimentation, many equivalents to specific embodiments of the invention described specifically herein. Such equivalents are intended to be encompassed in the scope of the following claim.

We claim:

1. A compound of formula (II):

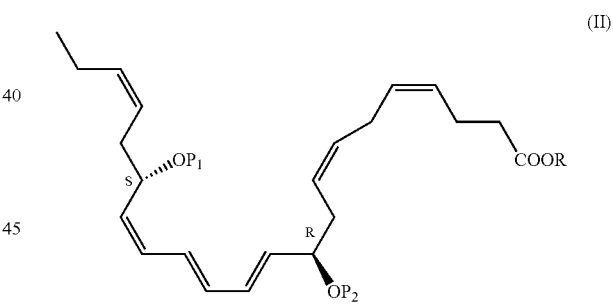

wherein R is a hydrogen atom, an alkyl group, or a pharmaceutically acceptable salt; and $P_1$ and $P_2$ are each, individually, a hydrogen atom or a protecting group, provided when $P_1$ and $P_2$ are both hydrogen atoms, then R is other than a hydrogen atom.

2. The compound of claim 1, wherein the compound is purified.

3. A composition comprising a compound of claim 1 and a pharmaceutically acceptable carrier.

4. The composition of claim 3, wherein the compound is purified.

5. A method to treat airway inflammation comprising administration of a therapeutically acceptable amount of a compound of claim 1.

6. The method of claim 5, wherein said airway inflammation is asthma.

7. A compound of formula (IX):

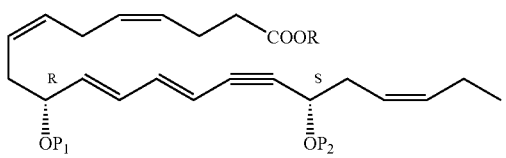

(IX)

wherein R is a hydrogen atom, an alkyl group, or a pharmaceutically acceptable salt; and
P$_1$ and P$_2$ are each, individually, a hydrogen atom or a protecting group.

8. The compound of claim 7, wherein when P$_1$ and P$_2$ are both hydrogen atoms, then R is other than a hydrogen atom.

9. The compound of claim 7, wherein P$_1$ and P$_2$ are each hydrogen atoms and R is a hydrogen atom.

10. A composition comprising a compound of claim 7 and a pharmaceutically acceptable carrier.

11. A method to treat airway inflammation comprising administration of a therapeutically acceptable amount of a compound of claim 7.

12. The method of claim 11, wherein P$_1$ and P$_2$ are each hydrogen atoms and R is a hydrogen atom.

13. The method of claim 11, wherein said airway inflammation is asthma.

14. The method of claim 11, wherein when P$_1$ and P$_2$ are both hydrogen atoms, then R is other than a hydrogen atom.

15. A method to treat airway inflammation comprising administration of a therapeutically acceptable amount of a composition of claim 10.

16. The method of claim 15, wherein P$_1$ and P$_2$ are each hydrogen atoms and R is a hydrogen atom.

17. The method of claim 15, wherein said airway inflammation is asthma.

18. A method to treat airway inflammation comprising administration of a therapeutically acceptable amount of a composition of claim 3.

19. The method of claim 15, wherein P$_1$ and P$_2$ are each hydrogen atoms and R is a hydrogen atom.

20. The method of claim 15, wherein said airway inflammation is asthma.

* * * * *